(12) United States Patent
Delmonico et al.

(10) Patent No.: US 8,177,557 B2
(45) Date of Patent: May 15, 2012

(54) DENTAL DEVICE, SUCH AS BRIDGE OR INSERT

(76) Inventors: Frank E. Delmonico, Wakefield, RI (US); Roy A. Waldheger, Narragansett, RI (US)

(*) Notice: Subject to any disclaimer, the term of this patent is extended or adjusted under 35 U.S.C. 154(b) by 0 days.

(21) Appl. No.: 13/134,342

(22) Filed: Jun. 6, 2011

(65) Prior Publication Data

US 2011/0236858 A1 Sep. 29, 2011

Related U.S. Application Data

(63) Continuation-in-part of application No. 12/164,970, filed on Jun. 30, 2008, now abandoned, which is a continuation-in-part of application No. 10/582,038, filed as application No. PCT/US2004/041981 on Dec. 15, 2004, now abandoned.

(60) Provisional application No. 60/529,475, filed on Dec. 15, 2003.

(51) Int. Cl.
  *A61C 13/12* (2006.01)
(52) U.S. Cl. ............................ 433/180; 433/215; 29/896.1
(58) Field of Classification Search .......... 433/171–173, 433/175–176, 178–182, 190–195; 29/896.1; 264/16–19
  See application file for complete search history.

(56) References Cited

U.S. PATENT DOCUMENTS

| | | | |
|---|---|---|---|
| 2,315,669 A | 4/1943 | Thompson | |
| 2,315,748 A | 4/1943 | Thompson | |
| 2,826,814 A | 11/1952 | Sappey et al. | |
| 3,641,670 A | 2/1972 | Karageorge | |
| 3,660,899 A | 5/1972 | Linkow | |
| 3,977,081 A * | 8/1976 | Zambelli et al. | 433/176 |
| 4,269,595 A | 5/1981 | Nemethy | |
| 4,360,342 A | 11/1982 | Salvo | |
| 4,431,417 A * | 2/1984 | Weissman | 433/182 |
| 4,433,960 A | 2/1984 | Garito et al. | |
| 4,457,714 A * | 7/1984 | Klein | 433/180 |
| 4,459,111 A * | 7/1984 | Valen | 433/176 |
| 4,521,192 A * | 6/1985 | Linkow | 433/173 |
| 4,537,575 A * | 8/1985 | Roberts | 433/176 |
| 4,661,066 A * | 4/1987 | Linkow et al. | 433/176 |
| 4,689,013 A | 8/1987 | Lustig | |
| 4,704,089 A * | 11/1987 | Shoher et al. | 433/183 |

(Continued)

FOREIGN PATENT DOCUMENTS

CA 2265339 3/1999

(Continued)

*Primary Examiner* — Cris L Rodriguez
*Assistant Examiner* — Hao D Mai
(74) *Attorney, Agent, or Firm* — Michael Best & Friedrich LLP

(57) ABSTRACT

A dental bridge and a dental device. The dental device may include a structural portion extending along an axis and connectable to at least one tooth. A truss portion may depend from the structural portion and be operable to support a pontic, the truss portion may define a plurality of slots extending from a peripheral surface. The structural portion may have a first surface oriented toward the occlusal surface and an opposite second surface, the structural portion defining a plurality of openings, the plurality of openings extending transverse to the axis and between the first surface and the second surface. The structural portion may define an angled surface leading into at least one of the plurality of openings. A plurality of projections may be formed on a first surface of the structural portion, each of the projections having a projection surface spaced beyond the first surface toward the occlusal surface.

22 Claims, 62 Drawing Sheets

U.S. PATENT DOCUMENTS

| | | | |
|---|---|---|---|
| 4,713,005 A * | 12/1987 | Marshall et al. | 433/180 |
| 4,735,571 A * | 4/1988 | Salvo | 433/215 |
| 4,758,162 A | 7/1988 | Dobbs | |
| 4,764,116 A * | 8/1988 | Shoher et al. | 433/180 |
| 4,775,320 A * | 10/1988 | Marshall et al. | 433/214 |
| 4,790,754 A * | 12/1988 | Weissman | 433/182 |
| 4,820,157 A | 4/1989 | Salvo | |
| 4,826,436 A * | 5/1989 | Shoher et al. | 433/208 |
| 4,877,400 A * | 10/1989 | Holsclaw | 433/183 |
| 4,894,012 A | 1/1990 | Goldberg et al. | |
| 4,950,162 A * | 8/1990 | Korber et al. | 433/180 |
| 4,957,439 A * | 9/1990 | Shoher et al. | 433/180 |
| 5,000,687 A | 3/1991 | Yarovesky et al. | |
| 5,074,791 A * | 12/1991 | Shoher et al. | 433/180 |
| 5,087,202 A | 2/1992 | Krenkel | |
| 5,194,001 A * | 3/1993 | Salvo | 433/180 |
| D336,683 S * | 6/1993 | Inoue et al. | D24/156 |
| 5,306,149 A * | 4/1994 | Schmid et al. | 433/173 |
| 5,433,607 A * | 7/1995 | Schmid et al. | 433/173 |
| 5,575,651 A * | 11/1996 | Weissman | 433/173 |
| 5,595,484 A | 1/1997 | Orikasa et al. | |
| 5,692,898 A | 12/1997 | Orikasa et al. | |
| 5,695,339 A | 12/1997 | Abere | |
| 5,713,737 A | 2/1998 | Sundstrom et al. | |
| 5,772,438 A * | 6/1998 | Deom | 433/181 |
| 5,788,492 A * | 8/1998 | Weissman | 433/173 |
| 5,803,737 A | 9/1998 | Lyalin | |
| 5,813,852 A | 9/1998 | Kawaguchi | |
| 5,888,068 A * | 3/1999 | Lans et al. | 433/181 |
| 5,934,907 A * | 8/1999 | Marshall | 433/181 |
| 5,975,904 A * | 11/1999 | Spiegel | 433/176 |
| 5,984,682 A | 11/1999 | Carlson | |
| 6,039,569 A | 3/2000 | Prasad et al. | |
| 6,050,820 A * | 4/2000 | Lans et al. | 433/181 |
| 6,116,070 A | 9/2000 | Oshida et al. | |
| 6,186,790 B1 | 2/2001 | Karmaker et al. | |
| 6,200,136 B1 | 3/2001 | Prasad et al. | |
| 6,224,374 B1 * | 5/2001 | Mayo | 433/180 |
| 6,250,925 B1 * | 6/2001 | Marshall | 433/181 |
| 6,299,446 B1 | 10/2001 | Ahlers | |
| 6,299,449 B1 | 10/2001 | Carlson | |
| 6,345,984 B2 | 2/2002 | Karmaker et al. | |
| 6,382,966 B1 | 5/2002 | Aknin | |
| 6,537,067 B1 * | 3/2003 | Wennemann | 433/76 |
| 6,575,740 B2 | 6/2003 | Kyung | |
| 6,599,125 B1 | 7/2003 | Freilich et al. | |
| 6,666,684 B1 * | 12/2003 | Names | 433/173 |
| 2001/0036617 A1 | 11/2001 | Karmaker et al. | |
| 2002/0086266 A1 | 7/2002 | Karmaker et al. | |
| 2002/0142265 A1 * | 10/2002 | Weissman | 433/173 |
| 2003/0064346 A1 | 4/2003 | Wennemann | |
| 2003/0124490 A1 | 7/2003 | Nielsen | |
| 2003/0211444 A1 | 11/2003 | Andrews | |
| 2006/0051723 A1 | 3/2006 | Morris | |

FOREIGN PATENT DOCUMENTS

EP        1023877        8/2000

* cited by examiner

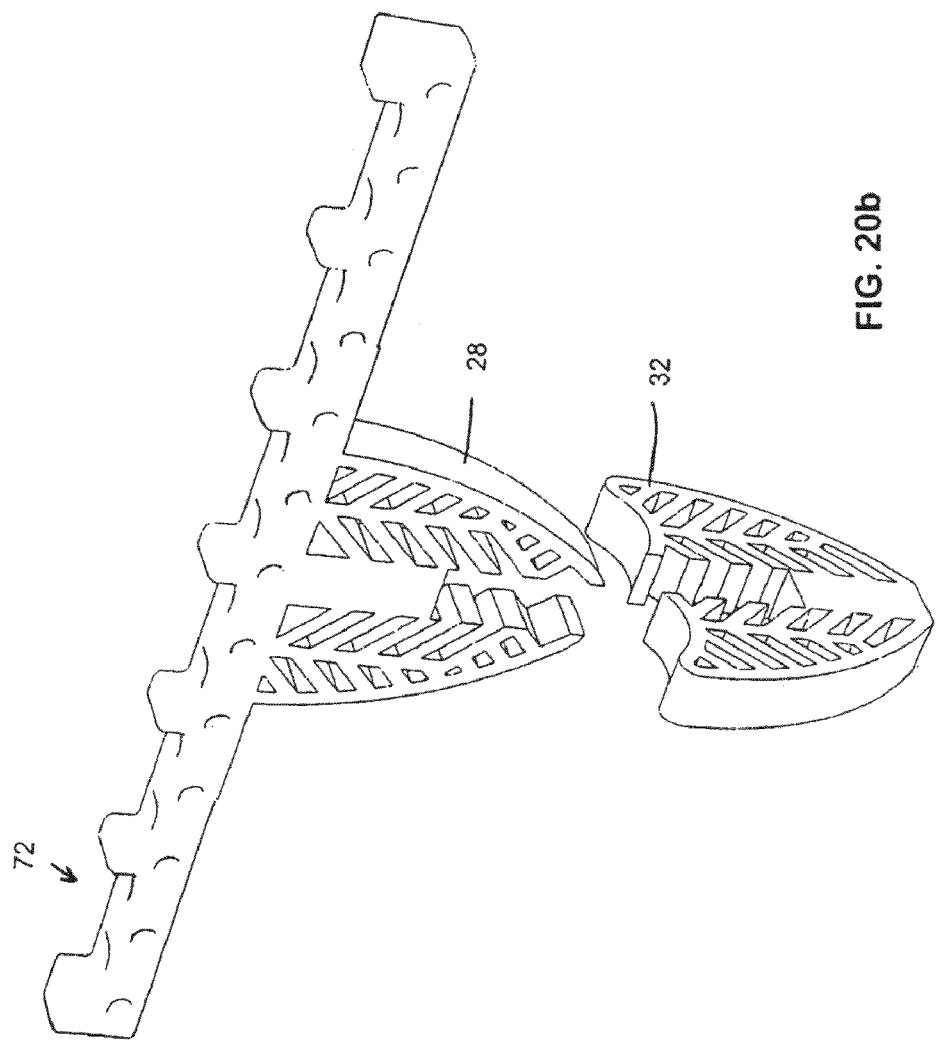

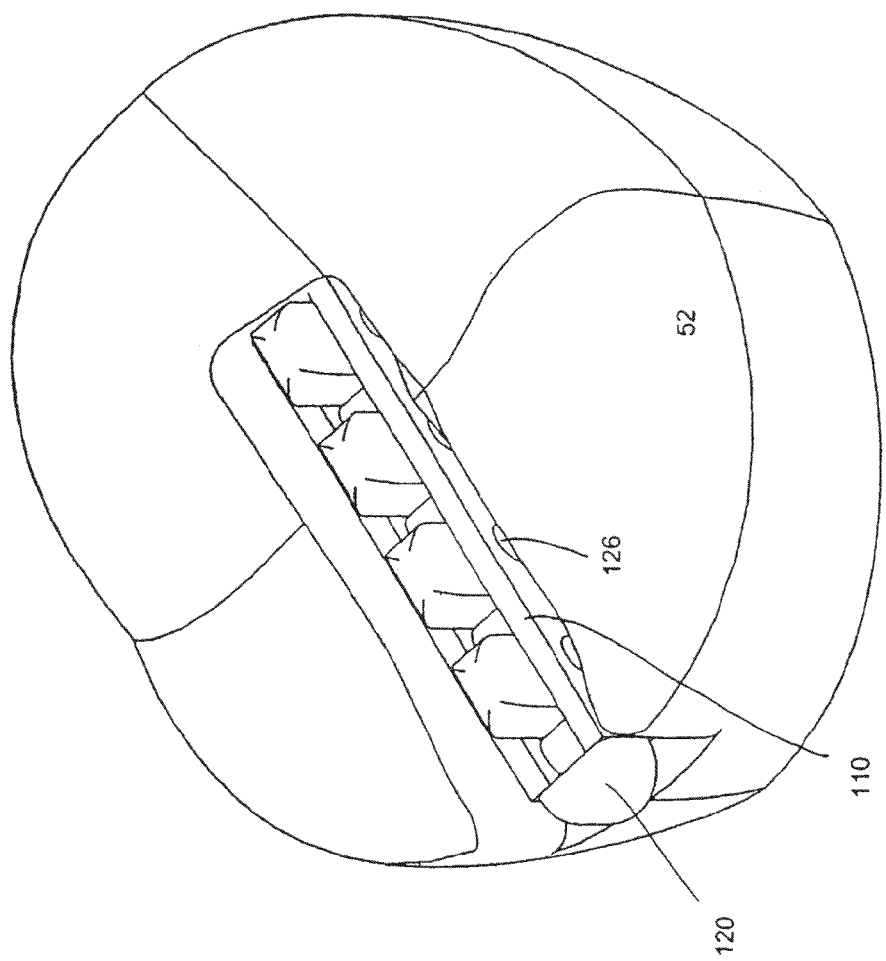

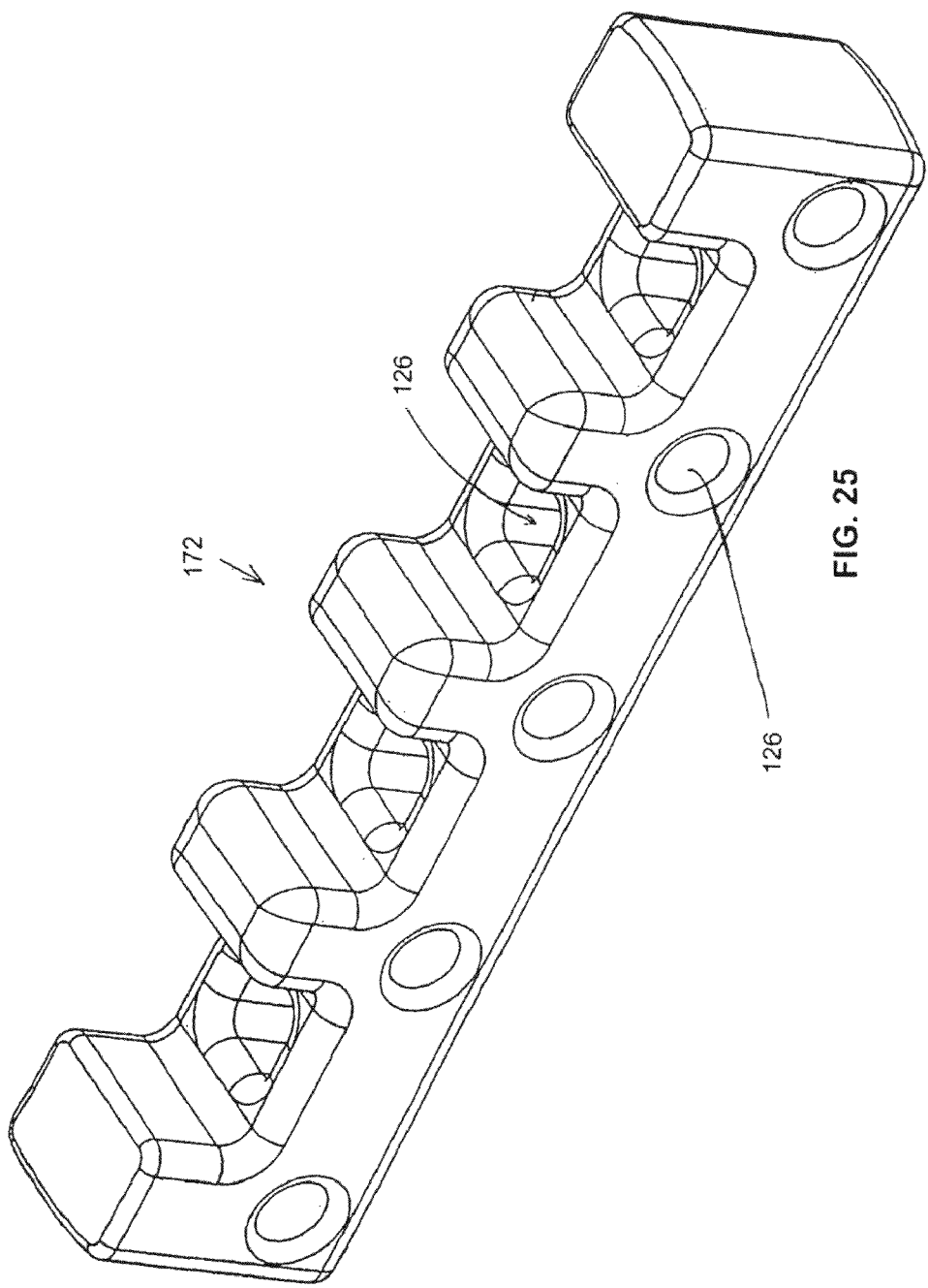

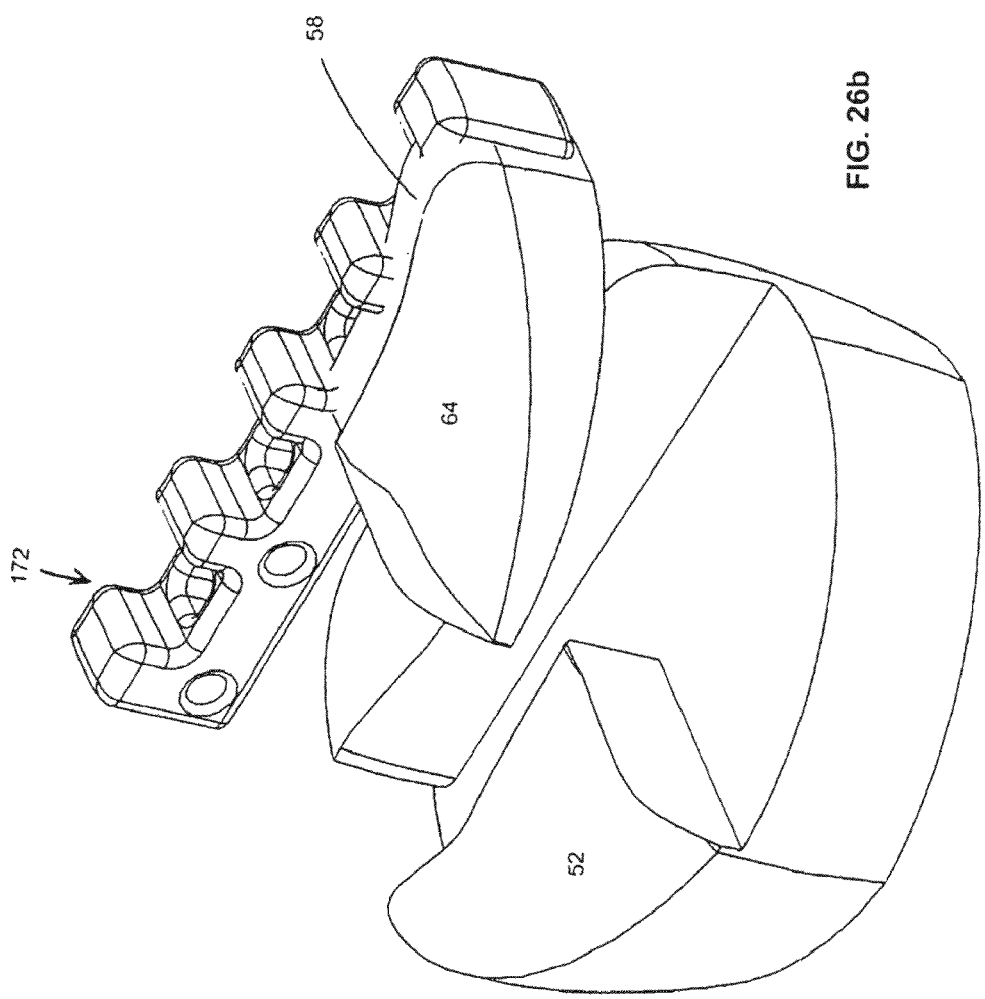

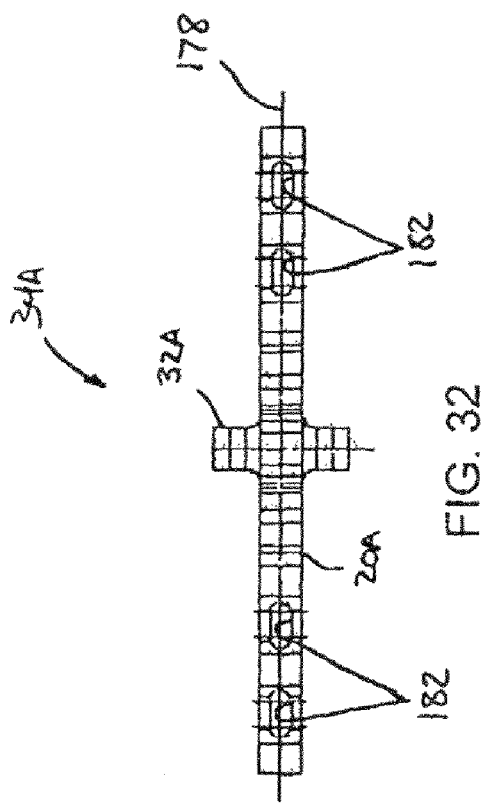
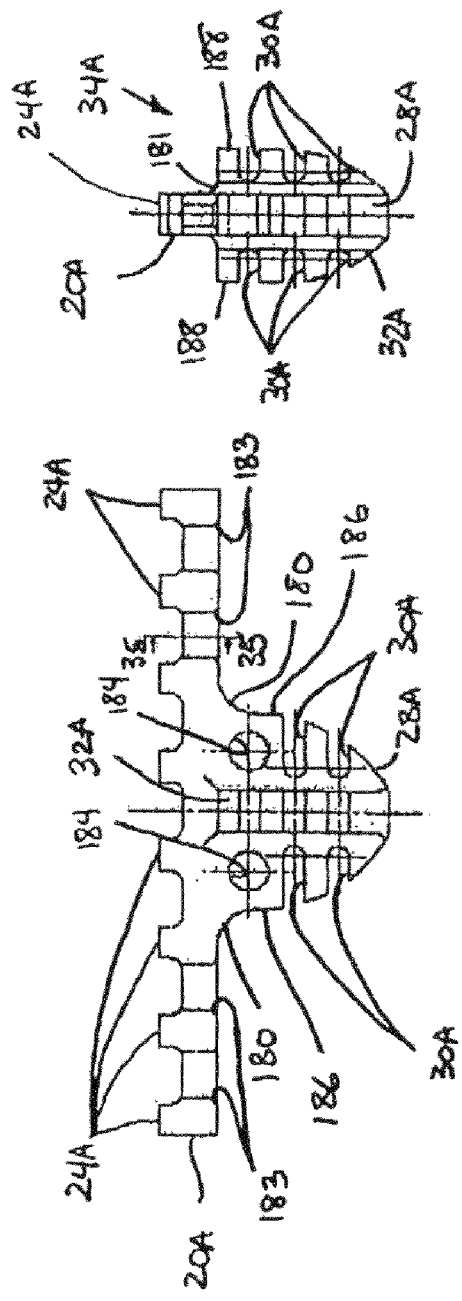
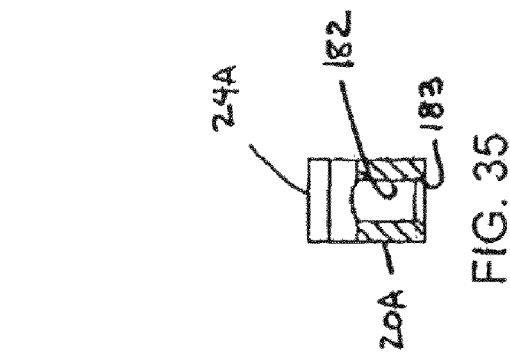

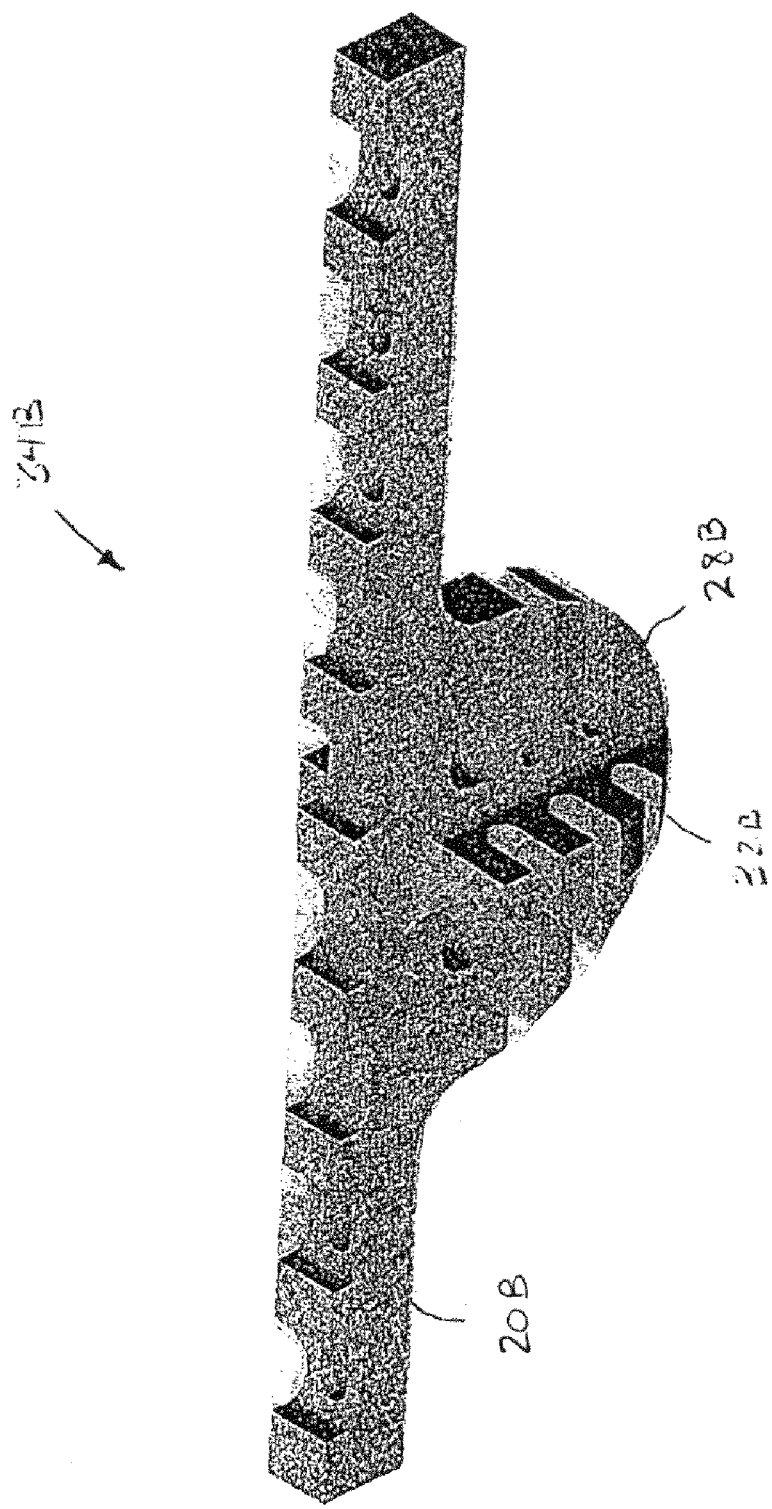

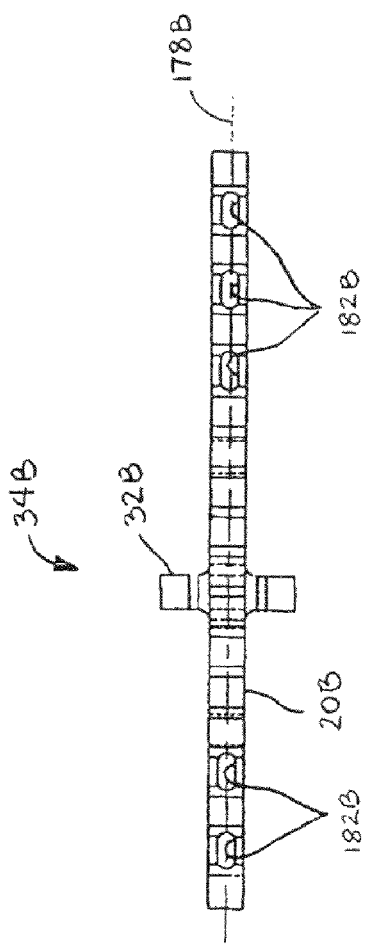
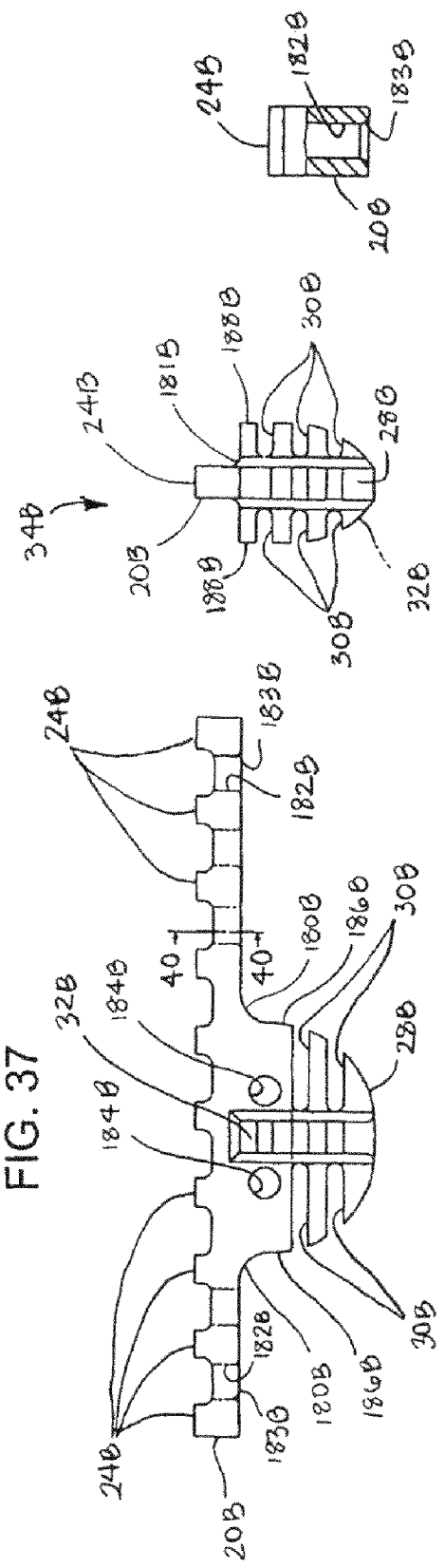
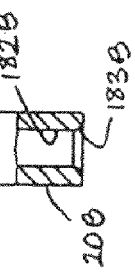
FIG. 40
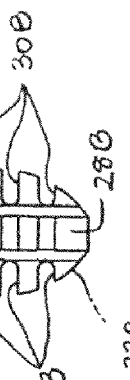
FIG. 39
FIG. 37
FIG. 38

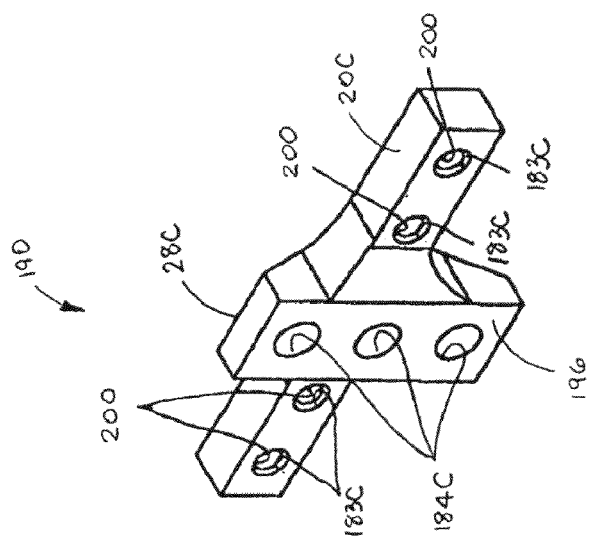

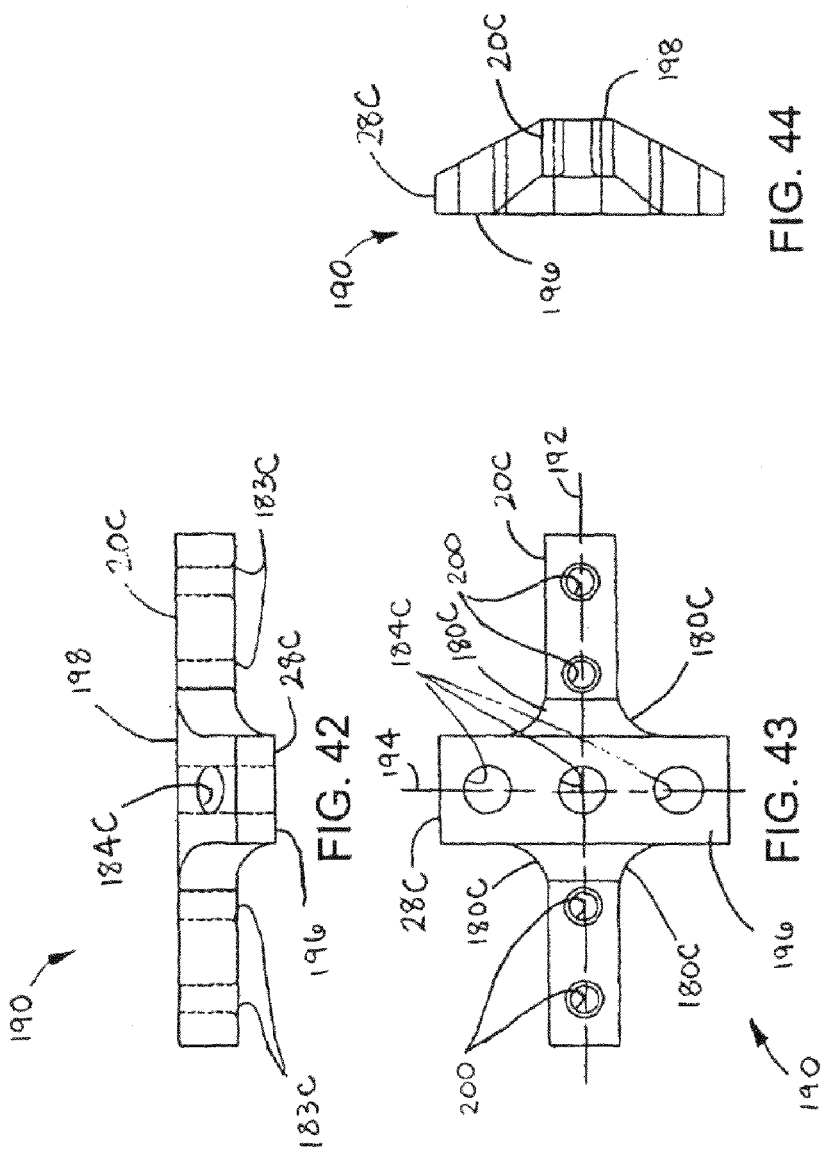

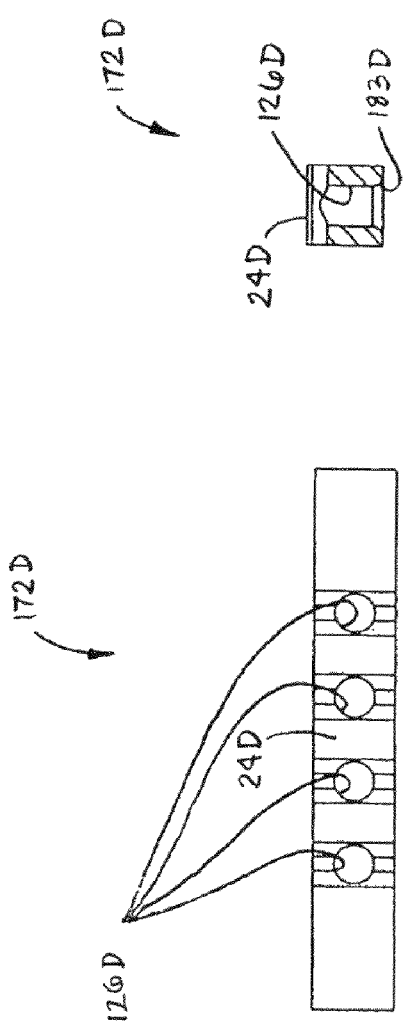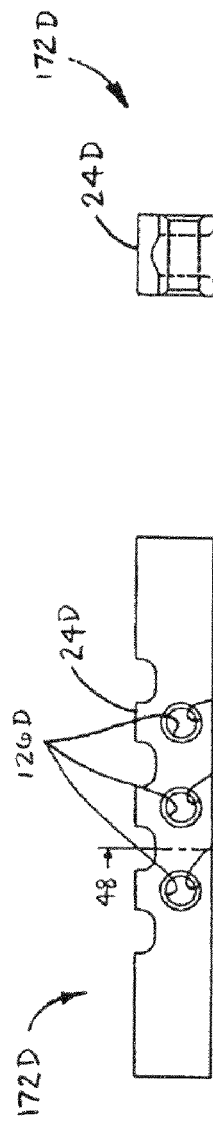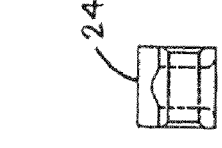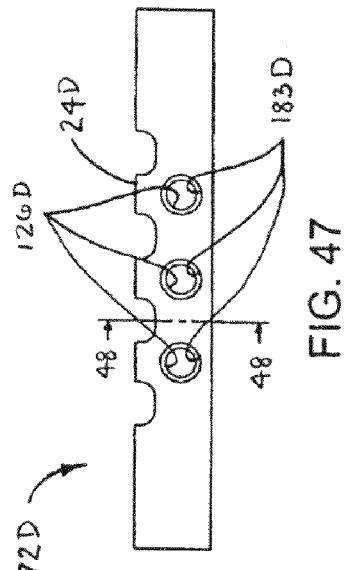

DENTAL DEVICE, SUCH AS BRIDGE OR INSERT

RELATED APPLICATIONS

The present application is a continuation-in-part of pending U.S. patent application Ser. No. 12/164,970, filed Jun. 30, 2008, published as U.S. Patent Application Publication No. US 2008-0318186 A1, on Dec. 25, 2008, which is a continuation-in-part of pending U.S. patent application Ser. No. 10/582,038, filed Apr. 11, 2007, published as U.S. Patent Application Publication No. US 2007-0281282 A1, on Dec. 6, 2007, now abandoned, which is the national application of International Application No. PCT/US2004/041981, filed Dec. 15, 2004, published as PCT Patent Application Publication No. WO 2005/058179 A1, on Jun. 30, 2005, which claims priority to prior-filed provisional patent U.S. Application Ser. No. 60/529,475, filed Dec. 15, 2003, the entire contents of all of which are considered as being part of the present application and are hereby incorporated by reference.

FIELD OF THE INVENTION

This invention relates generally to a dental bridge, insert or other dental device and, more particularly, to framework for use in producing tooth-replacement bridges, reconstructing one or more teeth or splinting one or more unstable teeth.

SUMMARY

In some independent aspects and in some constructions, an adjustable system for bonded composites may generally include a ladder supporting a truss in one of multiple relative positions therewith. The ladder generally includes opposing rails connected by a plurality of rungs. The plurality of rungs are spaced along the rails to define a plurality of openings between adjacent rungs. The truss generally includes a strip, which may be formed of metal or another material, having a plurality of upstanding projections. The projections are correspondingly spaced with the openings defined in the ladder to allow the truss to engage the ladder in a plurality of relative configurations. The combination of the ladder and truss may also provide a torsionally rigid and substantially stiff assembly with which to support one or more pontics and/or unstable teeth.

In some independent aspects and in some constructions, a system for bonded composites may generally include a reinforced substructure for supporting a pontic. The reinforced substructure, which may be formed of metal or another material, may be substantially webbed or generally include a plurality of apertures or perforations therethrough to allow the flow or seepage of resin through and around the substructure for increased bonding strength of the resin between the pontic and the substructure. The substructure also generally includes reinforcing structure or framework in a direction along the ladder and truss, to which the substructure is coupled, and in a direction substantially normal to the ladder and truss.

In some independent aspects and in some constructions, a system for bonded composites may generally include the ladder and truss structure having a sufficient length to extend substantially through one or more teeth and a plurality of apertures or perforations therein to allow the flow or seepage of resin through and around the ladder and truss for increased bonding strength of the resin between the supporting one or more teeth and the ladder and truss.

In some independent aspects and in some constructions, a system for bonded composites may generally include provisions for occlusal stops. One or more projections on the truss may be configured to extend sufficiently far through the ladder such that the one or more projections serve to slow or halt the occlusal wear of the pontic and/or of adjacent teeth.

In some independent aspects and in some constructions, a system for bonded composites may generally include a bendable ladder structure configured to go through a quadrant of teeth, a half-arch of teeth, or a full arch of teeth. The ladder structure may also be configured with an anterior segment for full or partial arch splinting. The anterior segment may include a single rail connecting ladder structures at opposite ends thereof, in addition to a plurality of apertures or perforations therethrough to allow the flow or seepage of resin through and around the ladder and truss for increased bonding strength of the resin between the supporting one or more teeth and the anterior segment. In addition, the bendable ladder structure may support a relatively long span of teeth or other attachments (e.g., arch wires).

In some independent aspects and in some constructions, a system for bonded composites may generally include a ladder and truss structure adaptable by the dentist and/or oral surgeon while sitting chair side with their patients. The adjustability built into the ladder and truss structure allows the dentist and/or oral surgeon to make adjustments to the composite without having to send it off-site to a laboratory.

In some independent aspects and in some constructions, a dental device may include a structural portion extending along an axis and connectable to at least one tooth. A truss portion may depend from the structural portion and be operable to support a pontic, the truss portion having a peripheral surface, the truss portion defining a plurality of slots, each of the slots extending from the peripheral surface. Each of the slots may extend parallel to the axis. The structural portion may have a first surface oriented toward the occlusal surface and an opposite second surface, the structural portion defining a plurality of openings, the plurality of openings extending transverse to the axis and between the first surface and the second surface. The structural portion may define an angled surface leading into at least one of the plurality of openings. A plurality of projections may be formed on a first surface of the structural portion, each of the projections having a projection surface spaced beyond the first surface toward the occlusal surface.

In some constructions, the dental device includes a dental bridge. In some constructions, the dental device includes an insert for one or more teeth.

In some independent aspects and in some constructions, a method of manufacturing a prefabricated dental bridge may be provided. The method may generally include forming a unitary dental bridge framework connectable to at least two abutment teeth, each abutment tooth having a tooth occlusal surface, and forming a pontic on the dental bridge framework.

Forming the unitary dental bridge framework may include forming a structural portion extending along an axis and having a width transverse to the axis and a length along the axis, the length being greater than the width, the structural portion having a first end and an opposite, second end, the first end being connectable to one abutment tooth and the second end being connectable to another abutment tooth, the structural portion having a first surface oriented toward the tooth occlusal surface and an opposite, second surface, and forming a truss portion integrally with the structural portion and depending from the second surface of the structural portion, the truss portion being positioned along the length of the structural portion spaced from the first end and from the second end, a first portion of the length of the structural portion being defined between the truss portion and the first end and a second portion of the length of the structural portion being defined between the truss portion and the second end.

Forming the unitary dental bridge framework may also include forming a first slot in the first portion of the length, the first slot extending along the axis and from the second surface toward the first surface, the first slot having opposite side walls, forming a second slot in the second portion of the length, the second slot extending along the axis and from the second surface toward the first surface, the second slot having opposite side walls, and forming a plurality of openings extending through the structural portion transverse to the axis and from the first surface toward the second surface, the plurality of openings being spaced from the truss portion along the length of the structural portion, at least one of the plurality of openings being formed in the first portion of the length of the structural portion, at least another of the plurality of openings being formed in the second portion of the length of the structural portion.

In some independent aspects and in some constructions, a method of installing a prefabricated dental bridge may be provided. The method may generally include, prior to a dentist examining a patient, manufacturing the prefabricated dental bridge, manufacturing including forming a unitary dental bridge framework including forming a structural portion extending along an axis, and forming a truss portion integrally with the structural portion, the truss portion depending from the structural portion, and forming a tooth-shaped pontic on the dental bridge framework. The method may also include providing the prefabricated dental bridge to the dentist, examining the patient, preparing at least two abutment teeth of the patient, positioning the dental bridge on the abutment teeth, and bonding the dental bridge to the abutment teeth.

In some independent aspects and in some constructions, a prefabricated dental bridge may generally include a unitary dental bridge framework connectable to at least two abutment teeth, the unitary dental bridge framework including a structural portion extending along an axis, and a truss portion integrally formed with the structural portion and depending from the structural portion; and a tooth-shaped pontic formed on the dental bridge framework.

Independent features and independent advantages of the present invention will become apparent to those skilled in the art upon review of the following detailed description, claims and drawings.

BRIEF DESCRIPTION OF THE DRAWINGS

FIG. 20b is an exploded view of another construction of the reinforcing structure, with a substructure coupled to a bridge.

FIG. 24 is a perspective view of the combination shown in FIG. 22 inserted into a single tooth.

FIG. 25 is a perspective view of another construction of an insert for use in individual single composite restorations, with a bridge.

FIG. 26b is a perspective view of the insert bonded to a quarter of a pontic shown in FIG. 26a being inserted into a damaged tooth for bonding thereto.

FIG. 32 is a top view of the truss structure shown in FIG. 30.

FIG. 33 is a front view of the truss structure shown in FIG. 30.

FIG. 34 is a right side view of the truss structure shown in FIG. 30.

FIG. 35 is a partial cross-sectional view of a portion of the truss structure taken generally along line 35-35 in FIG. 33.

FIG. 36A is a top perspective view of another construction of a dental device, such as a truss structure or bridge framework.

FIG. 37 is a top view of the truss structure shown in FIG. 36A.

FIG. 38 is a front view of the truss structure shown in FIG. 36A.

FIG. 39 is a right side view of the truss structure shown in FIG. 36A.

FIG. 40 is a partial cross-sectional view of a portion of the truss structure taken generally along line 40-40 in FIG. 38.

FIG. 41 is a top perspective view of another construction of a dental device, such as a truss structure or bridge framework.

FIG. 42 is a top view of the truss structure shown in FIG. 41.

FIG. 43 is a front view of the truss structure shown in FIG. 41.

FIG. 44 is a right side view of the truss structure shown in FIG. 41.

FIG. 46 is a top view of the insert shown in FIG. 45.

FIG. 47 is a front view of the insert shown in FIG. 45.

FIG. 48 is a partial cross-sectional view of a portion of the insert taken generally along line 48-48 in FIG. 47.

FIG. 49 is a right side view of the insert shown in FIG. 45.

Figures 1A, 1B:
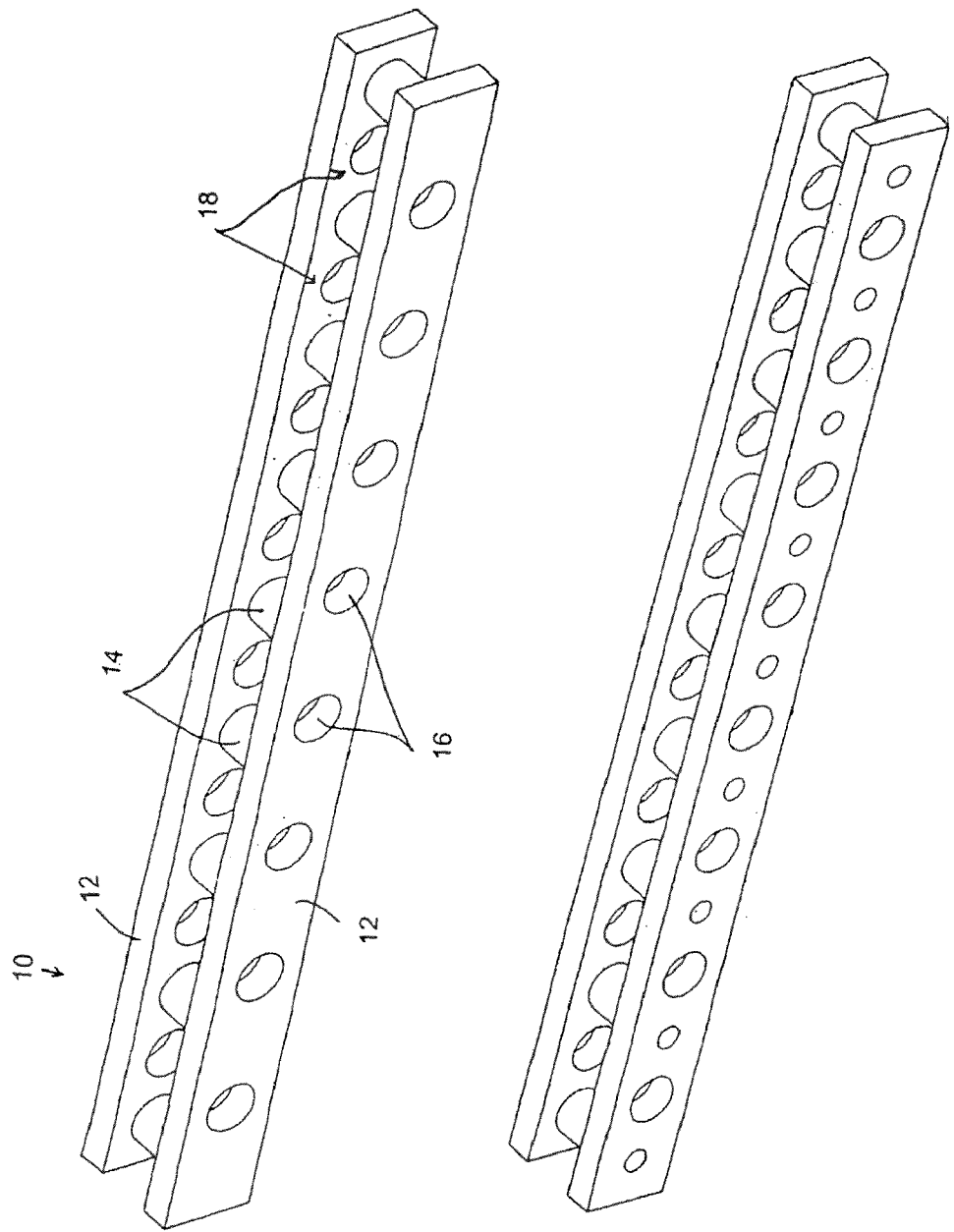
FIG. 1 is a perspective view of a ladder structure.

Before any independent features and at least one construction of the invention are explained in detail, it is to be understood that the invention is not limited in its application to the details of construction and the arrangements of the components set forth in the following description or illustrated in the drawings. The invention is capable of other constructions and of being practiced or being carried out in various ways. Also, it is understood that the phraseology and terminology used herein is for the purpose of description and should not be regarded as limiting. The use of "including", "having" and "comprising" and variations thereof herein is meant to encompass the items listed thereafter and equivalents thereof as well as additional items.

Although references may be made below to directions, such as upper, lower, downward, upward, rearward, bottom, front, rear, etc., in describing the drawings, these references are made relative to the drawings (as normally viewed) for convenience. These directions are not intended to be taken literally or limit the present invention in any form. In addition, terms such as "first" and "second" are used herein for purposes of description and are not intended to indicate or imply relative importance or significance.

DETAILED DESCRIPTION

In some independent aspects and in some constructions, an adjustable system for bonded composite dentistry may be provided. The system for bonded composites generally includes multiple parts that can be altered and used alone or in combination to perform a plurality of operations such as, for example, splinting one or more unstable teeth, reconstructing one or more teeth, supporting pontics, bridging gaps between teeth, preventing additional wear on new or existing teeth, etc.

As described below in more detail, in some constructions, a dental device, such as a prefabricated dental bridge, may generally include an oversized composite resin pontic molded onto a prefabricated (e.g., medical-grade titanium) framework which may feature occlusal stops/projections alternating with occlusal perforations/openings. One or two teeth on either side of an edentulous space are prepared with MOD, MO, or DO preps, and the dental bridge is then shaped to fit the preps and edentulous space. During installation, composite resin flows both around the structural portion and into and through the occlusal perforations. When light cured, the composite resin mechanically and chemically locks the bridge in place.

The dental device may be a prefabricated, mass produced dental bridge which is oversized in both length and pontic size so that it can be reduced in size and installed by a dentist to fit any appropriate patient in one visit. The illustrated dental devices may provide a minimally invasive, structurally sound, low-cost alternative to implants, one-tooth partials, Maryland bridges and other conventional fixed bridgework. The shaping and adapting of the illustrated dental devices can be accomplished chair side (direct method) or in the office lab using a quick set stone or plaster model from an impression of the appropriate quadrant (indirect method).

Figure 13:
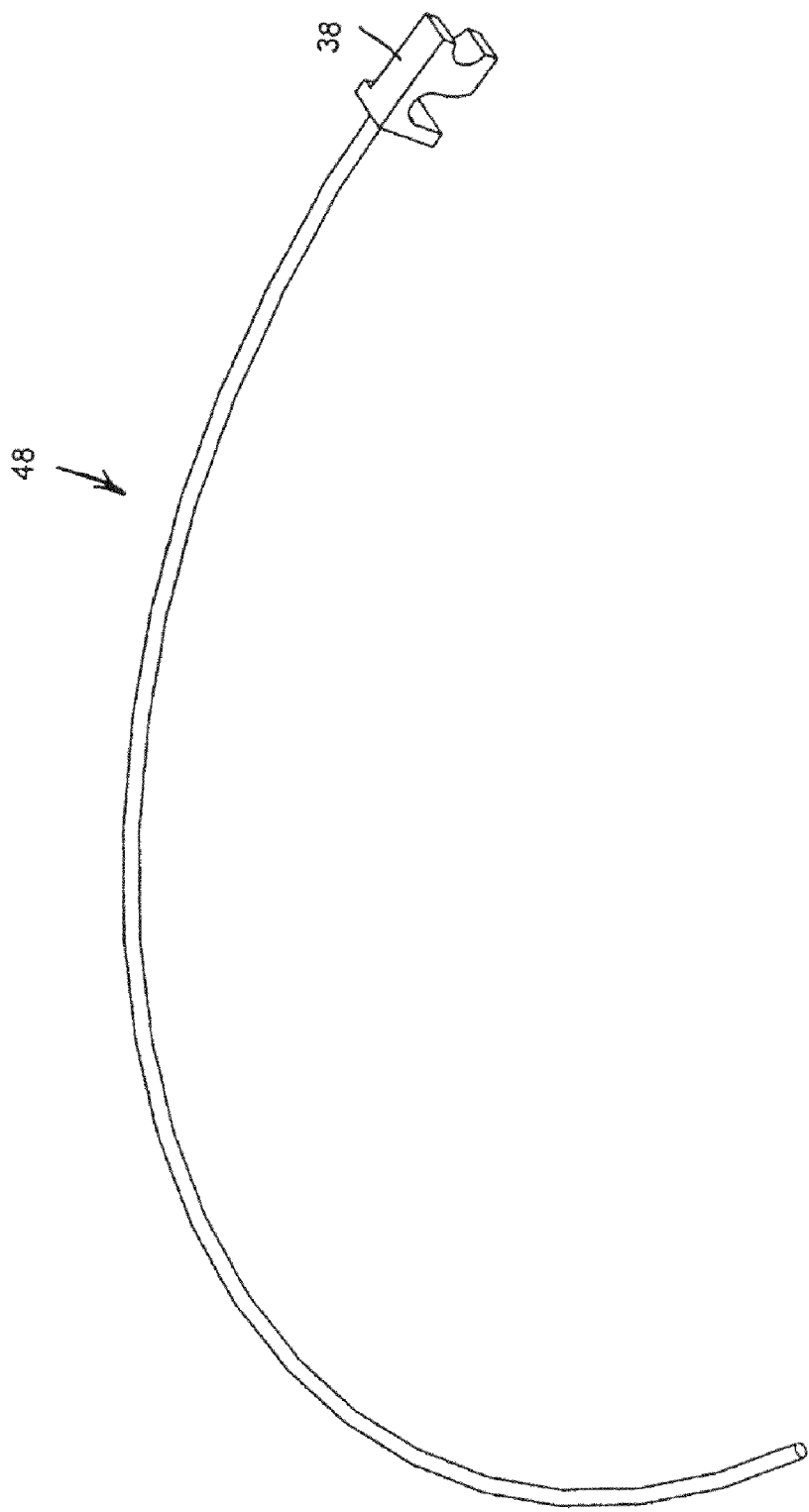
FIG. 13 is a perspective view of an anterior arch wire.
Figures 1, 13A:
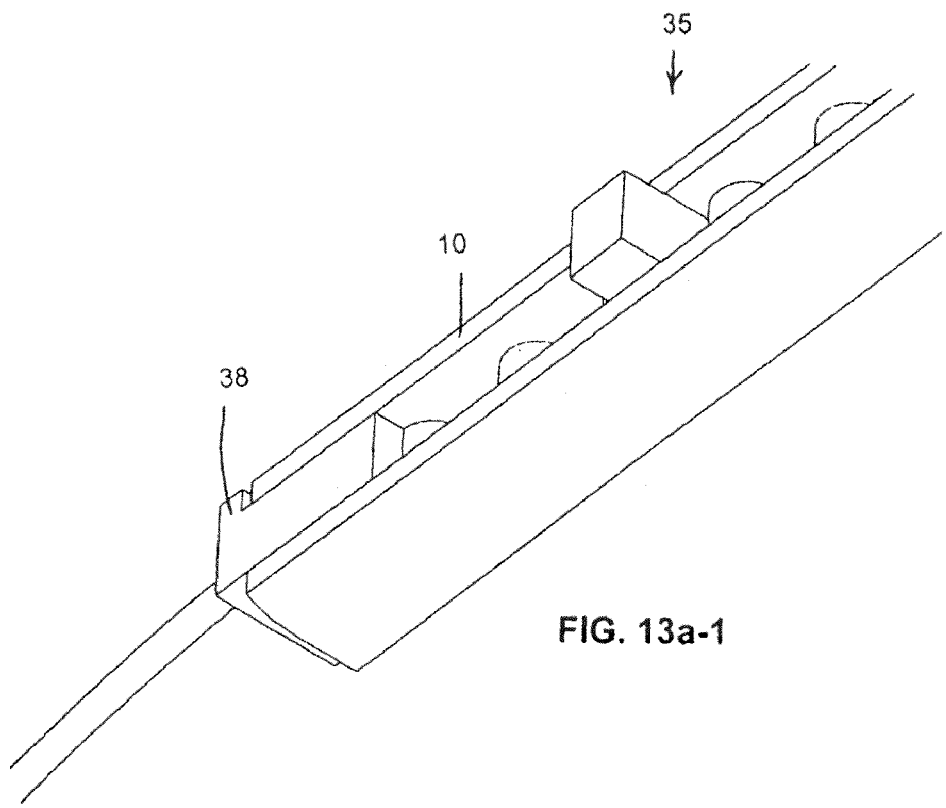
FIG. 13a is an enlarged perspective view illustrating the connection between the anterior arch wire shown in FIG. 13 and the ladder structure shown in FIG. 1.
Figures 2, 13A:
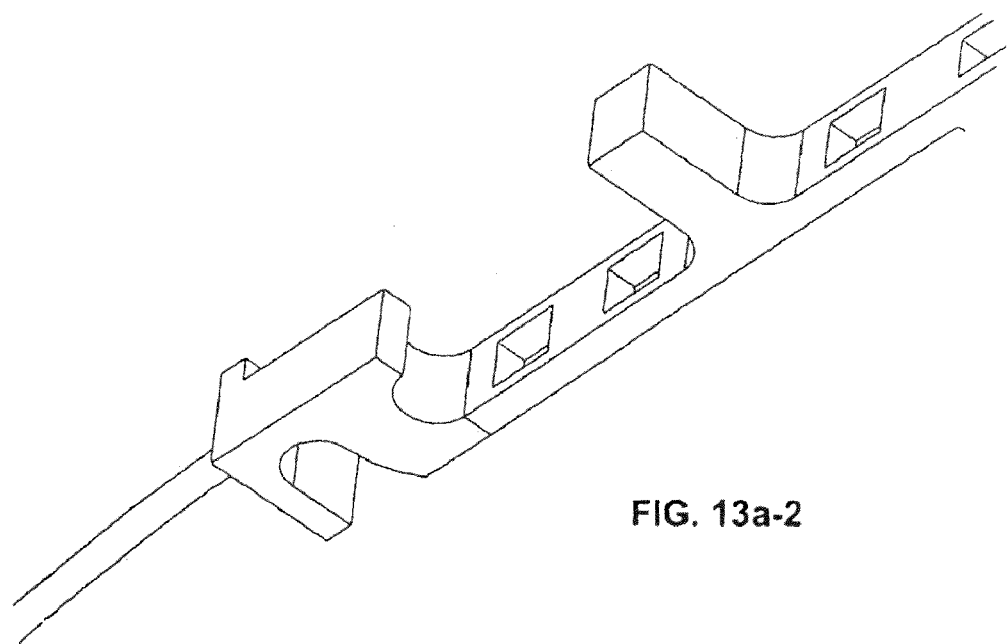

As shown in FIG. 1, a first member, a ladder structure, or a ladder 10, includes opposing rails 12 connected by a plurality of rungs 14. The length of the ladder 10 can be adjusted and may vary greatly. In the illustrated construction and in some aspects, the configuration of the ladder 10 provides the ladder 10 with an increased torsional rigidity and stiffness not found in conventional bridge framework and/or connecting assemblies.

In the illustrated construction, the rails 12 each include a plurality of apertures or perforations 16 therethrough. The apertures 16 can be round and are distributed along the ladder 10 to, for example, allow for the flow of composite resin. In the illustrated construction, the rails 12 are configured such that they are separable from one another so a segment comprising a singular rail may be formed, if desired, as part of the overall framework of the ladder 10.

The plurality of rungs 14 are spaced along the rails 12 to define a plurality of openings 18 between adjacent rungs 14. The rungs 14 may be hollow or solid. The rungs 14 may have various cross-sectional shapes such as, for example, round, oval or square.

Figure 2:
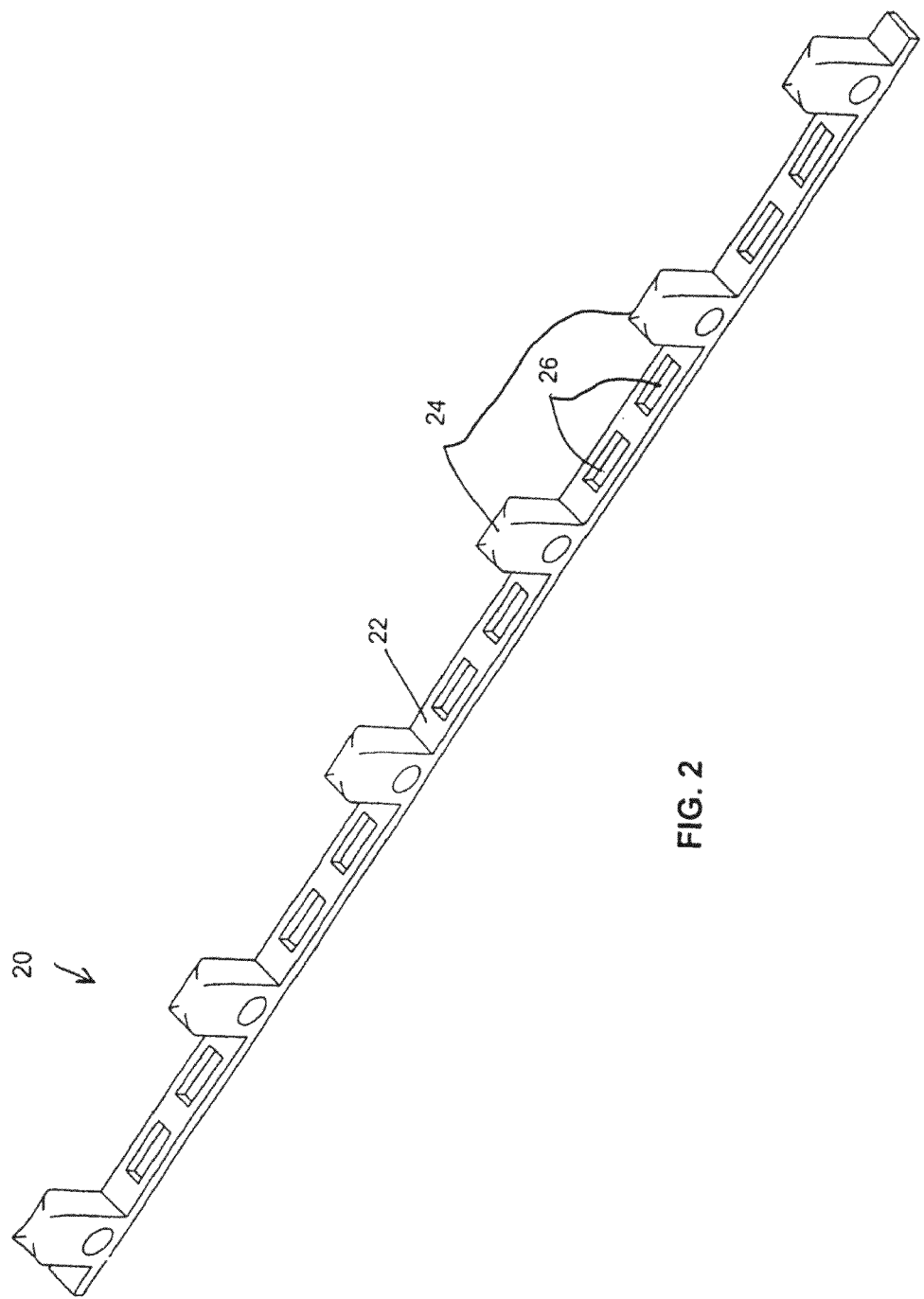
FIG. 2 is a perspective view of a truss structure that is engageable with the ladder structure shown in FIG. 1.
Figure 3:
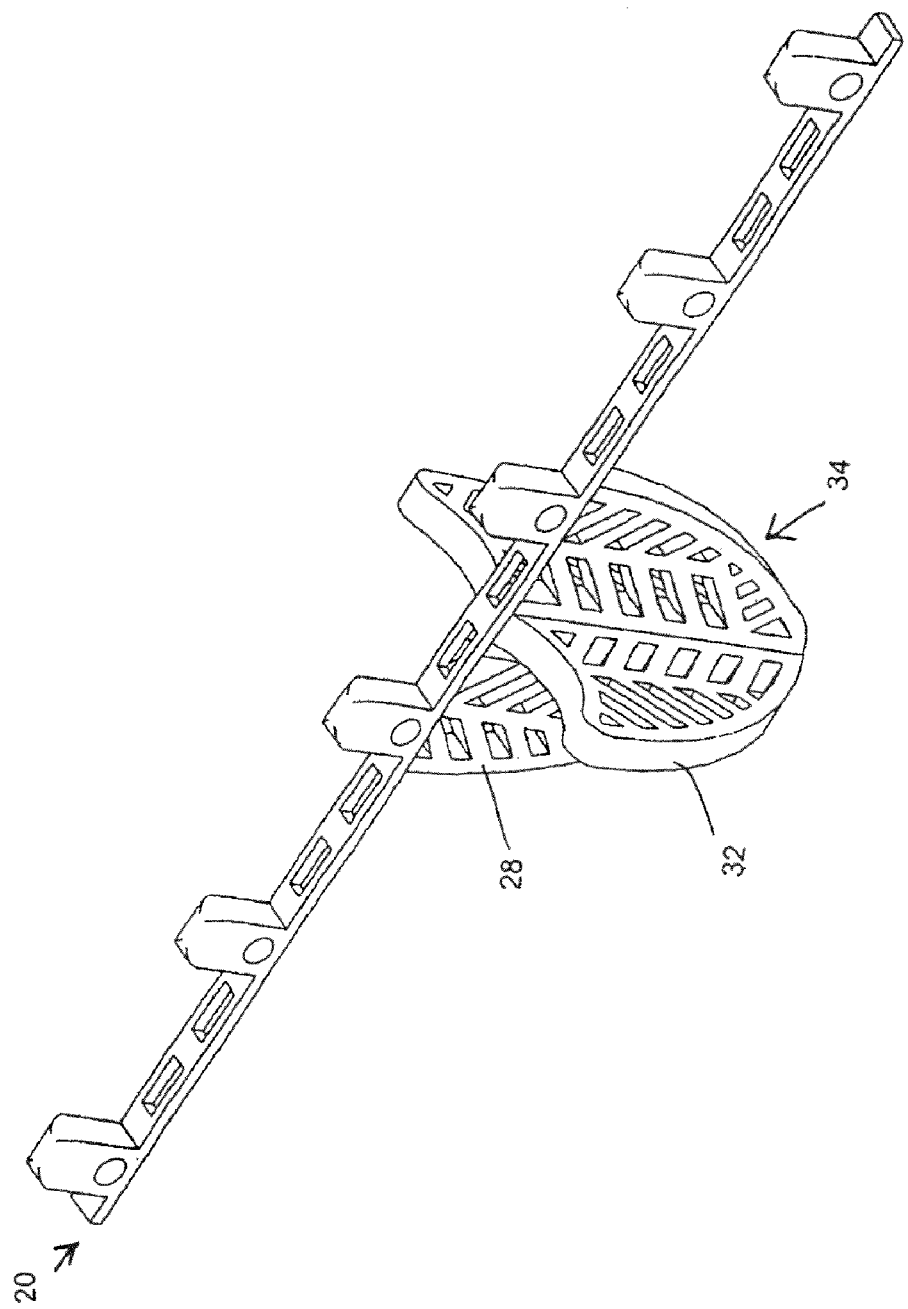
FIG. 3 is a perspective view of the truss structure shown in FIG. 2 with a reinforcing structure for supporting a pontic.

With reference to FIG. 2, a second member, a truss structure, or a truss 20, is shown. In the illustrated construction and in some aspects, the combination of the ladder 10 and truss 20 also provides a torsionally rigid and substantially stiff bridge with which to support one or more pontics and/or unstable teeth.

In the illustrated construction, the truss 20 includes a strip 22 having a plurality of upstanding projections 24. The projections 24 may act as occlusal stops and to protect the biting portion of bonded teeth from the wear that occurs through mastication and contact with the opposite set of teeth. The projections 24 of the truss 20 are correspondingly spaced with the openings 18 defined in the ladder 10 to allow the truss 20 to engage the ladder 10 in a plurality of relative configurations to yield a bridge. One or more apertures 26 may also be formed through the truss 20 in a location between the projections 24.

The projections 24 may be arranged on the truss 20 to engage in the opening 18 between every, every other, every third or every fourth rung 14 in the ladder 10. As a result, the truss 20 may fit precisely between the two rails 12, and the projections 24 may fit precisely in the opening 18 between every, every other, every third, or every fourth rung 14 in the ladder 10 to interlock the truss 20 and ladder 10. In addition, the projections 24 may act as occlusal stops by extending above the ladder 10 (e.g., ending 1-1.5 mm above the height of the top portion of the rails 12 and rungs 14). The truss 20, after interlocking with the ladder 10, reinforces and/or bridges the openings or open span between the rungs 14 on the ladder 10.

Figure 4:
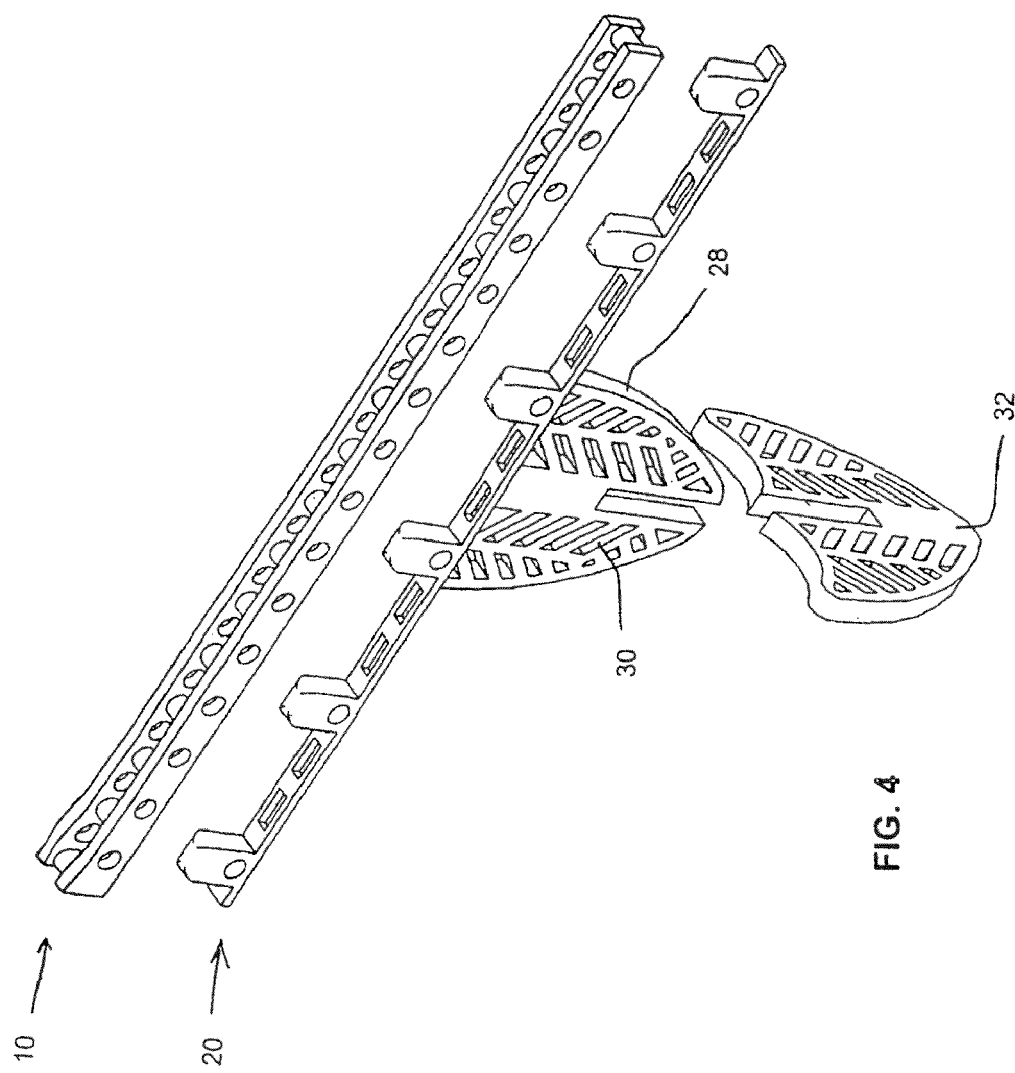
FIG. 4 is an exploded view of the ladder structure shown in FIG. 1 and the truss structure shown in FIG. 2 and the reinforcing structure shown in FIG. 3.

FIG. 4 shows the ladder 10, truss 20, and a reinforced substructure 28 coupled to the truss 20. In the illustrated construction, the substructure 28 is substantially webbed, and includes a plurality of apertures or perforations 30 therethrough to, for example, allow the flow or seepage of resin through and around the substructure 28 for increased bonding strength of the resin between a pontic and the substructure 28. The apertures or perforations 30 through the substructure 28 provide an increased surface area on which the resin is to bond.

The substructure 28 can be connected to a cross truss 32, as shown in FIG. 4. With the substructure 28 positioned along the truss 20, the reinforcing structure 32 can be positioned in a direction substantially normal to the truss 20, creating a reinforcing structure 34. A pontic formed around the reinforcing structure 34 may have an increased torsional rigidity as a result of the resin bonding with the reinforcing structure 34.

One or more portions of the truss 20 (e.g., the strip 22, the projections 24, the substructure 28, the cross truss 32, etc.) may be formed of metal. In the illustrated construction, the structures of the truss 20 are formed of metal. In other constructions, one or more of the structures of the truss 20 may be formed of another material, such as, for example, a composite material.

Figure 5:
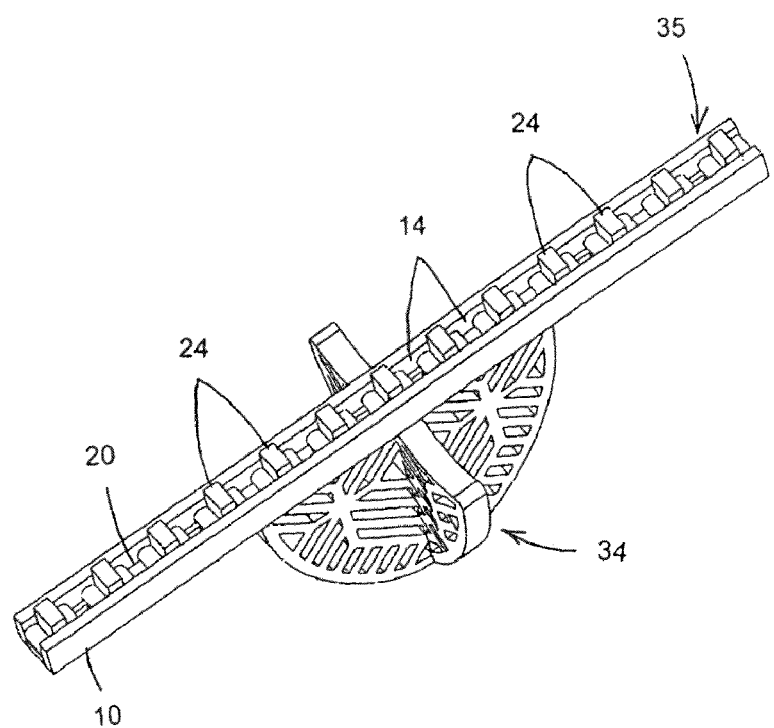
FIG. 5 is a top perspective view of the ladder structure shown in FIG. 1, and the truss structure shown in FIG. 2, connected to form a bridge, with the reinforcing structure shown in FIG. 3 coupled to the bridge for supporting a pontic in preparation for bonding to prepared teeth.
Figure 29:
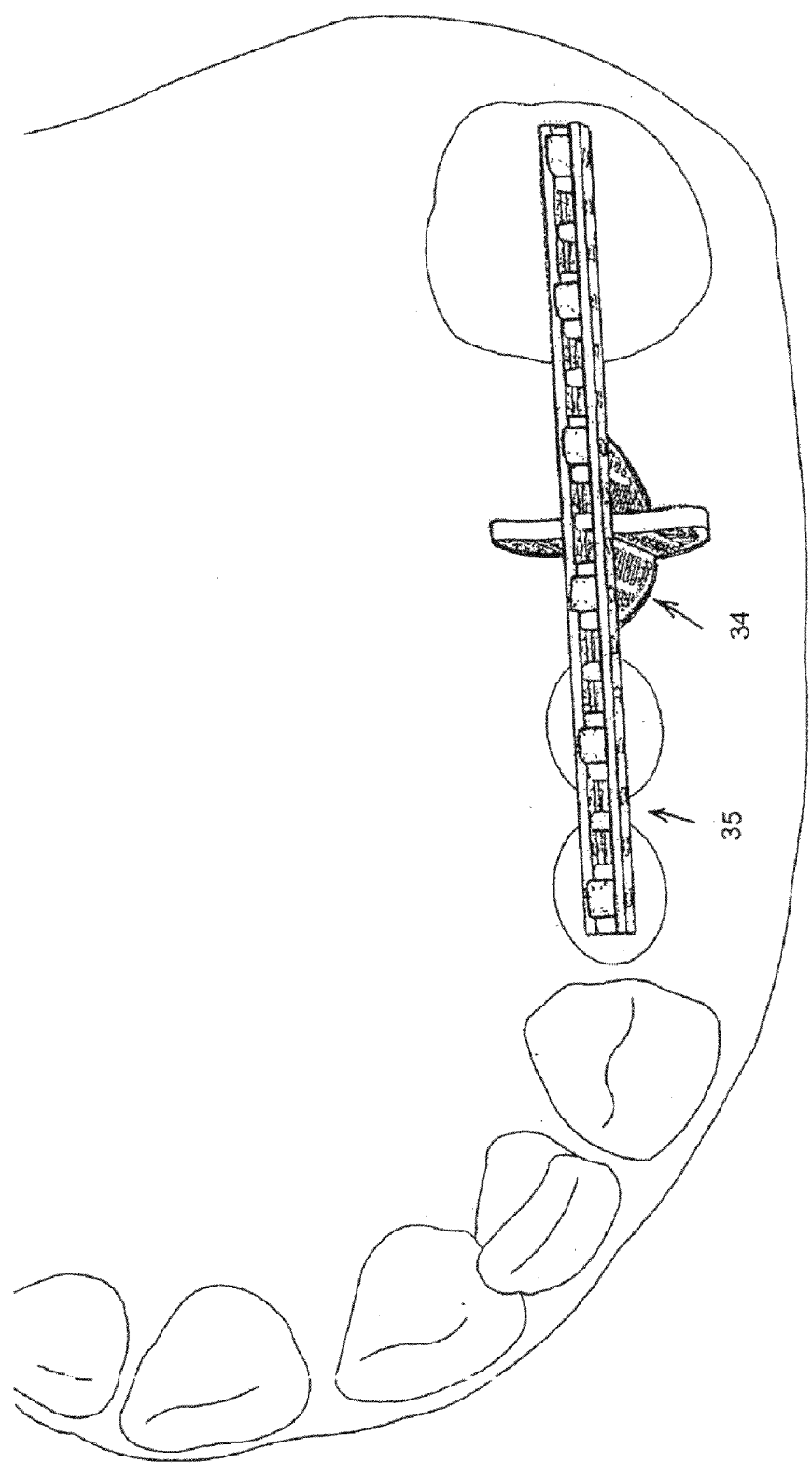
FIGS. 29 and 29a are views of a bridge with a reinforcing structure of FIG. 5 inserted into the lower set of teeth, with the reinforcing structure fitting into an edentulous space.
Figure 29A:
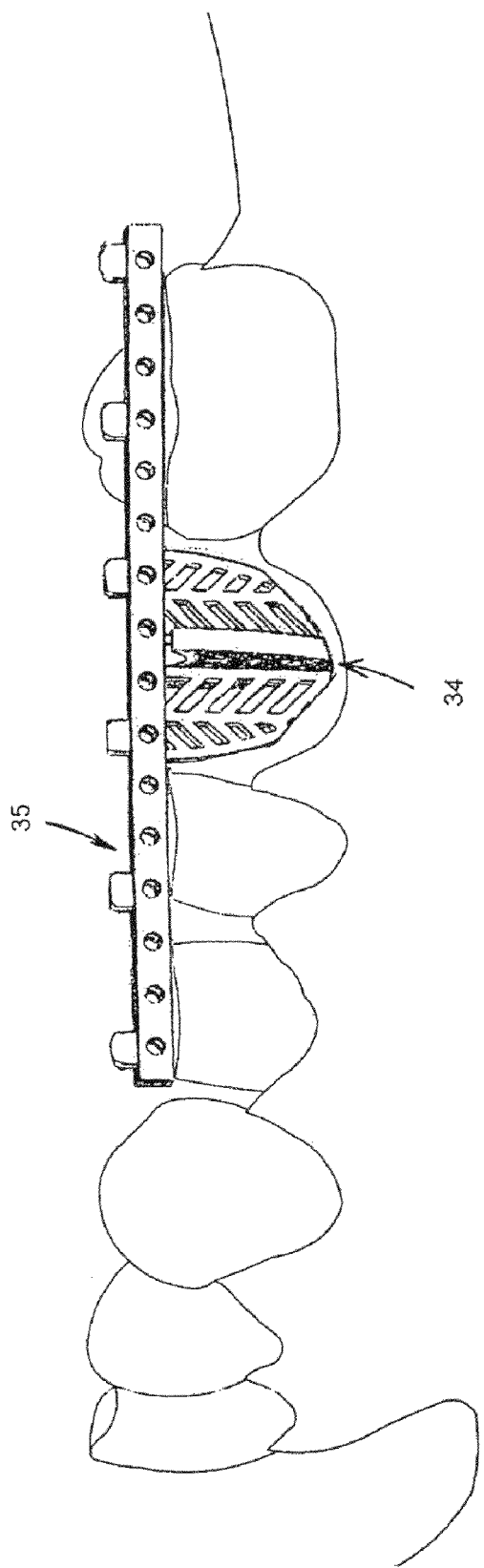

FIG. 5 shows a joined ladder 10 and truss 20, hereinafter referred to (with a pontic (not shown in FIG. 5)) as a bridge 35. The projections 24 of the truss 20 are shown engaging every other rung 14 of the ladder 10. The rungs 14 of the ladder 10 are shown as being square in this construction. FIGS. 29 and 29*a* are views of a bridge 35 with a reinforcing structure 34 inserted into the lower set of teeth, with the reinforcing structure 34 fitting into an edentulous space.

Figure 6:
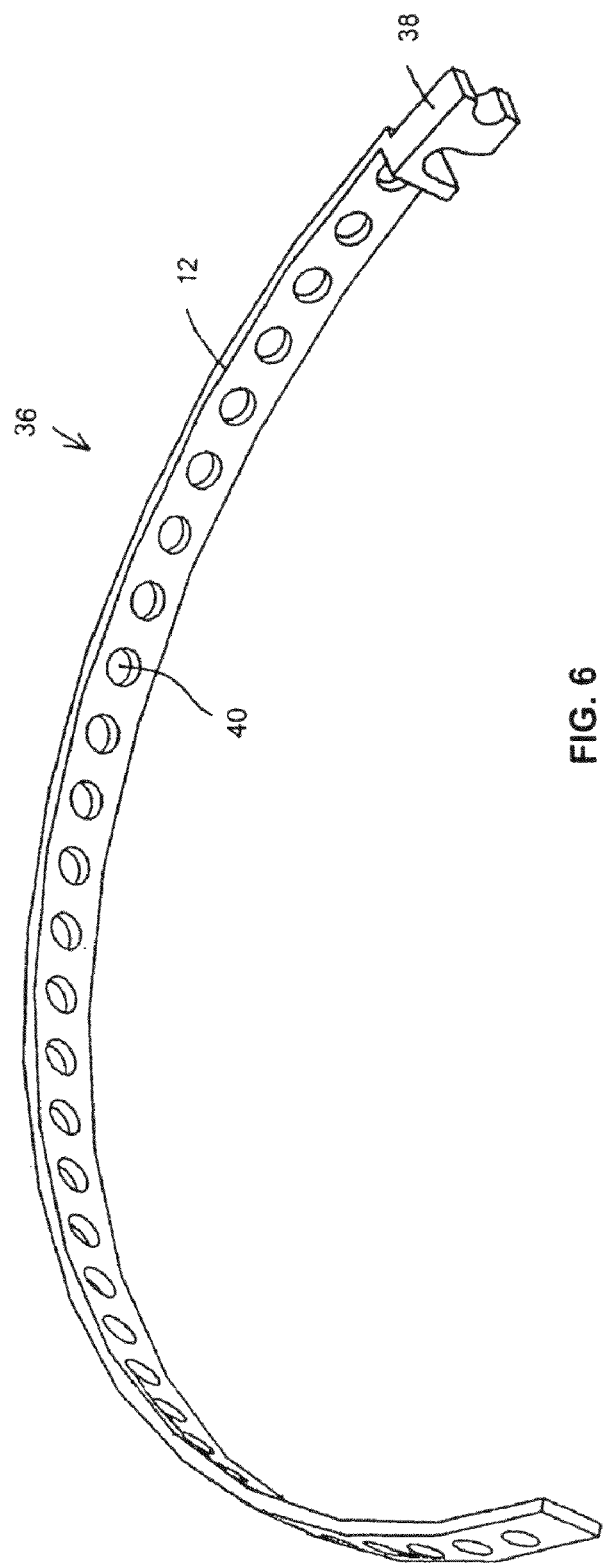
FIG. 6 is a perspective view of an anterior perforated segment.

With reference to FIG. 6, an anterior perforated segment 36 is shown. The segment 36 can be formed independently or by removing the rungs 14 and one rail 12 of the ladder 10 used on the sides of the mouth. The segment 36 has a connection portion or piece 38 that can be coupled to the ladder 10 used on the side of the mouth to form a single component. The piece 38 includes a first recess or slot which extends transverse to the axis and a second recess which extends along the axis. The segment 36 includes a plurality of perforations 40 that, for example, allows resin bonding material to seep through.

Figure 7:
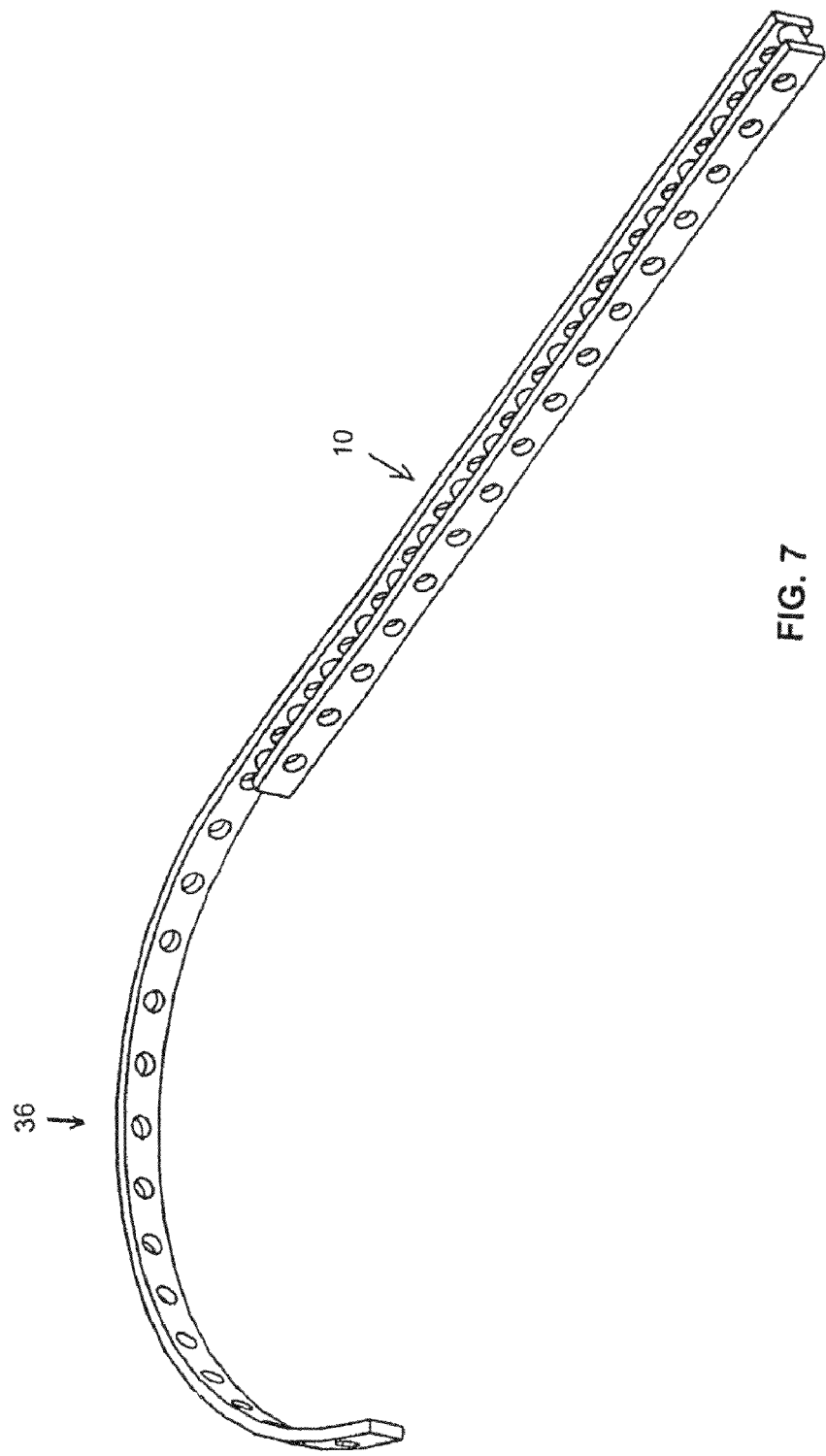
FIG. 7 is a perspective view of the ladder structure shown in FIG. 1 connected to the anterior perforated segment shown in FIG. 6.
Figure 8:
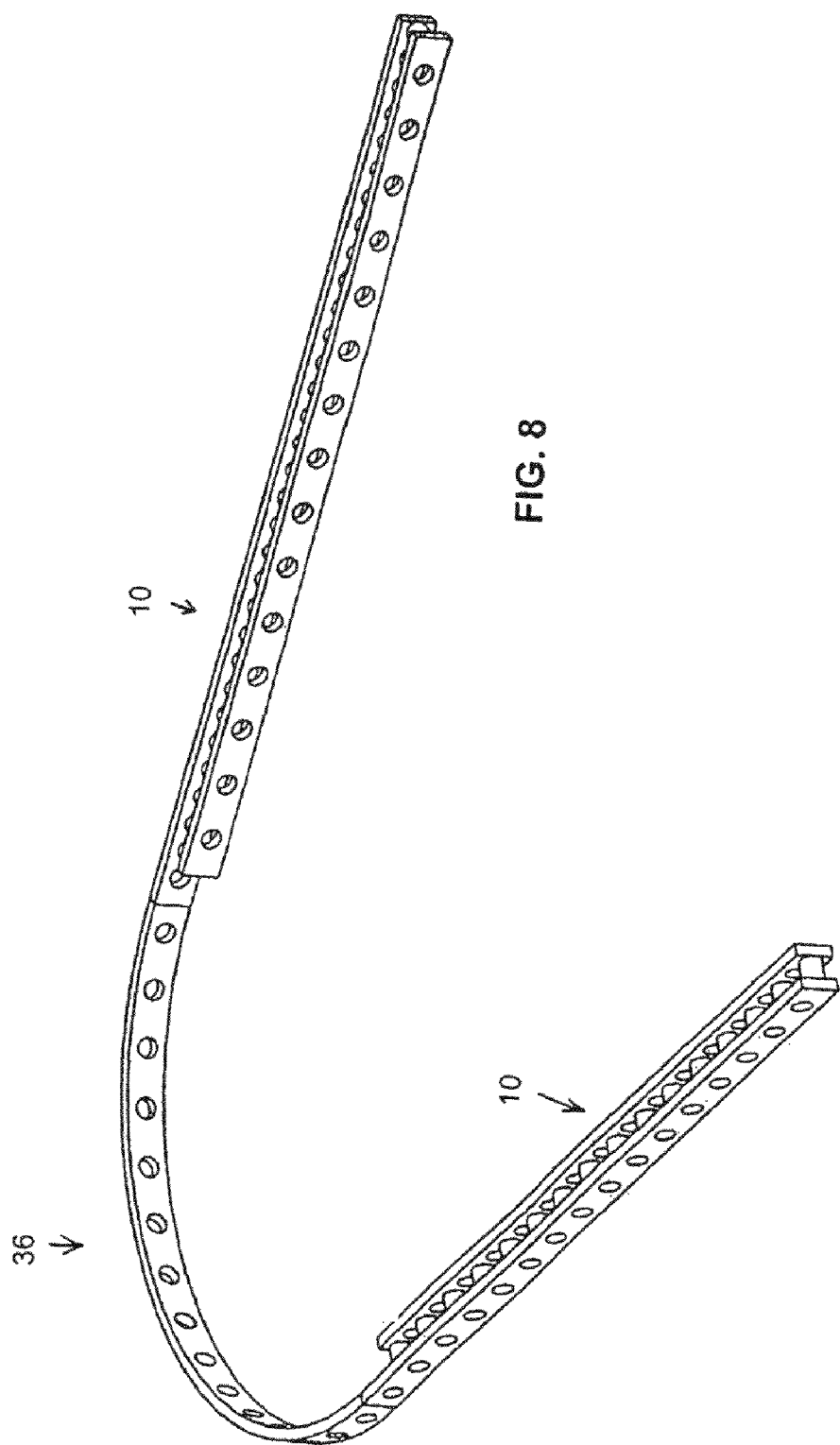
FIG. 8 is a perspective view of two ladder structures shown in FIG. 1 connected to the anterior perforated segment shown in FIG. 6.

As illustrated in FIG. 7 and FIG. 8, the segment 36 can be locked to a ladder 10 on both sides. Connecting the segment 36 on both sides to two individual ladders 10 would require two connection pieces 38 rather than a single connection piece 38 as shown in FIG. 6. The segment 36, bridge 35, and reinforcing structure 34 can be used in combination for supporting a pontic and stabilizing loose teeth, as illustrated in FIG. 9.

Figure 10:
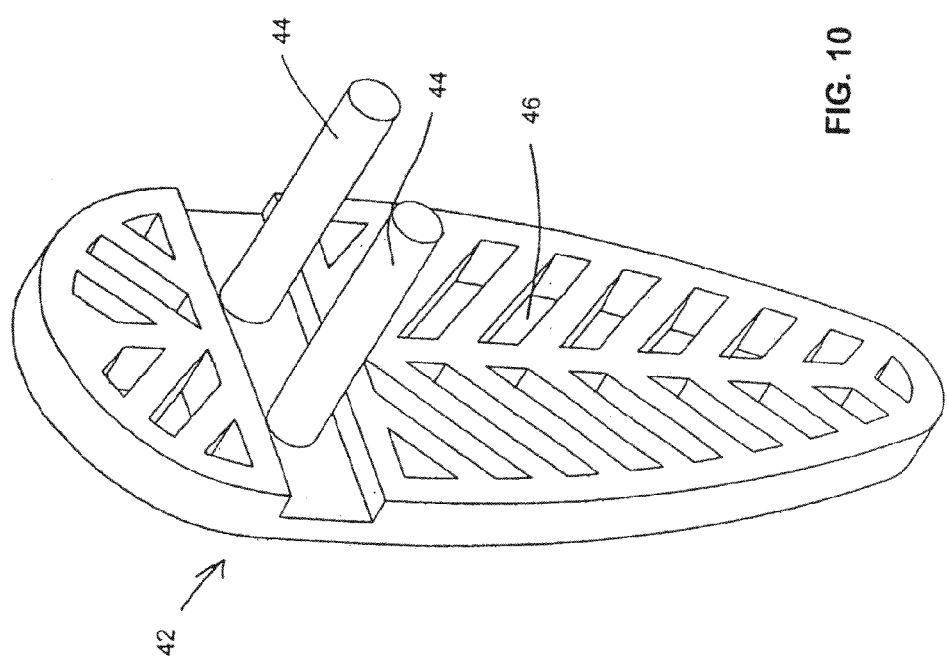
FIG. 10 is a rear perspective view of a shield for supporting an anterior pontic.
Figure 11:
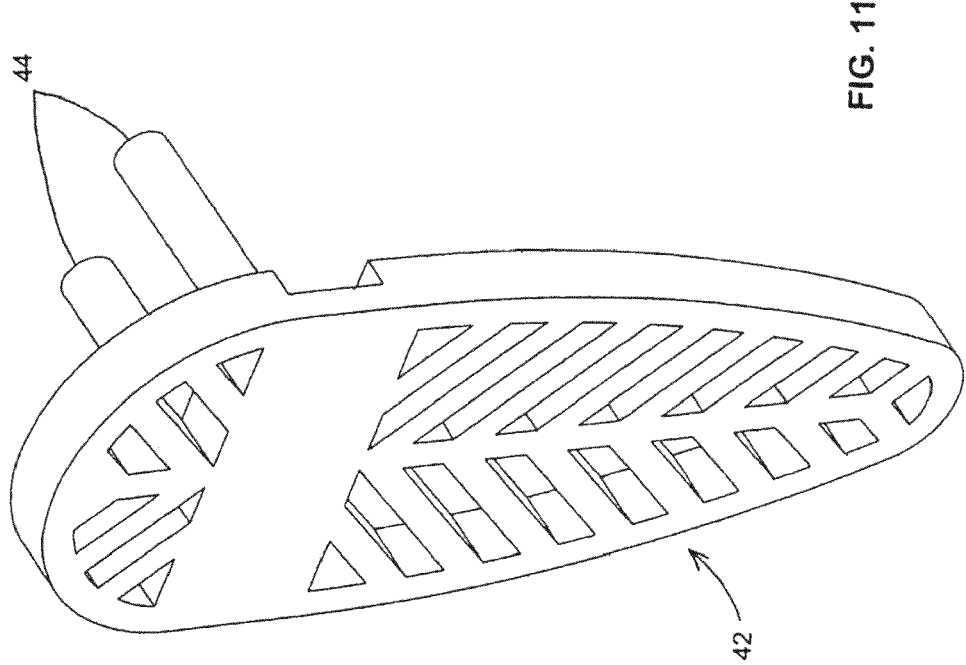
FIG. 11 is another perspective view of the shield in FIG. 10 for supporting an anterior pontic.

With reference to FIG. 10 and FIG. 11, alternate sides of a shield 42 are shown. The shield 42 has projections 44 positioned to engage the perforations 40 of the anterior perforated segment 36. In the illustrated construction, the shield 42 is also substantially webbed and includes a plurality of apertures or perforations 46 therethrough to, for example, allow the flow or seepage of resin through and around the segment 36 for increased bonding strength of the resin between an anterior pontic and the segment 36. In the illustrated construction, the shield 42 and the projections 44 are formed of metal but, in other constructions, may be formed of another material.

Figure 9:
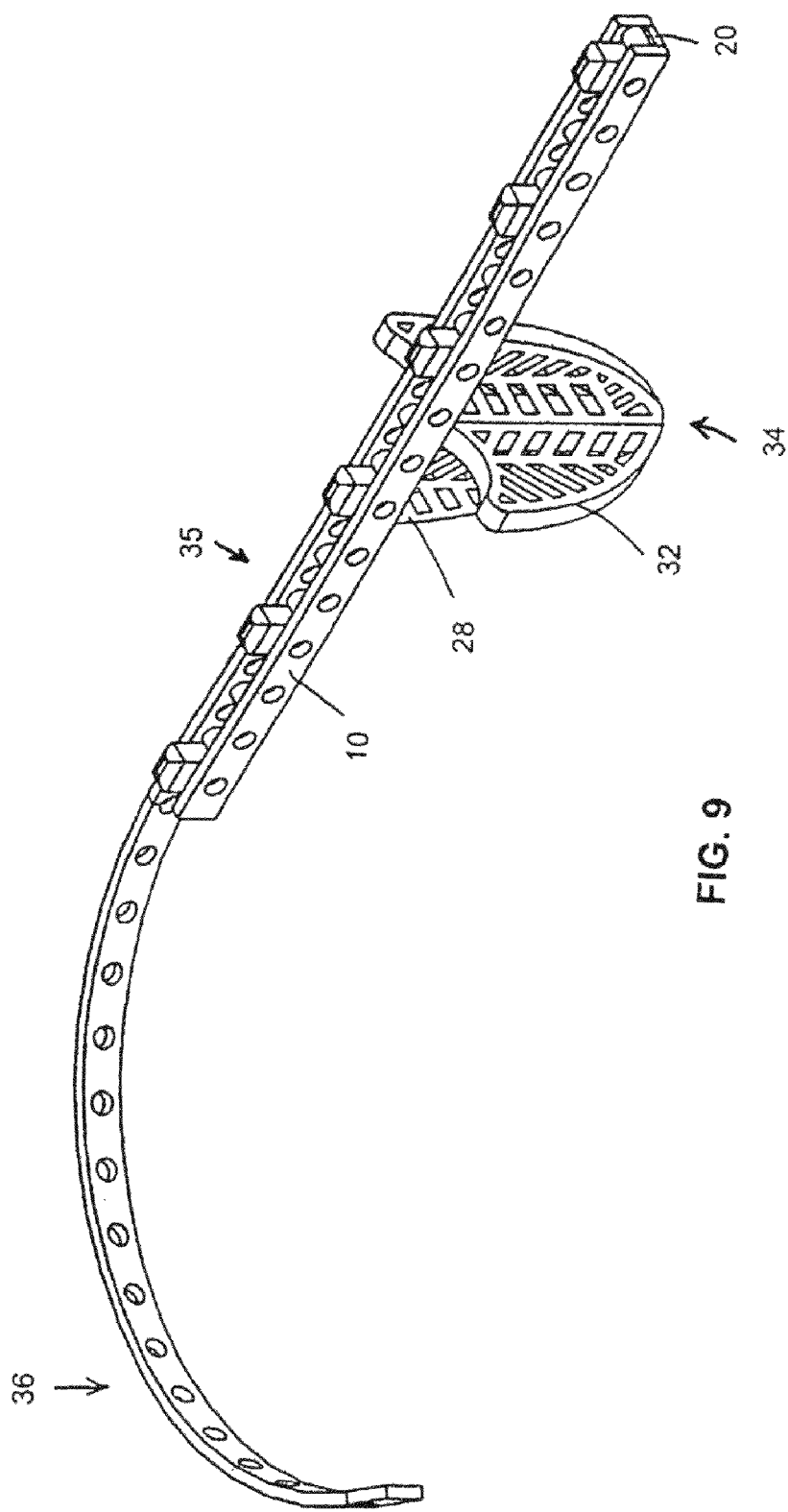
FIG. 9 is a perspective view of a combination of the bridge and reinforcing structure shown in FIG. 5, coupled to the anterior perforated segment shown in FIG. 6.
Figure 12:
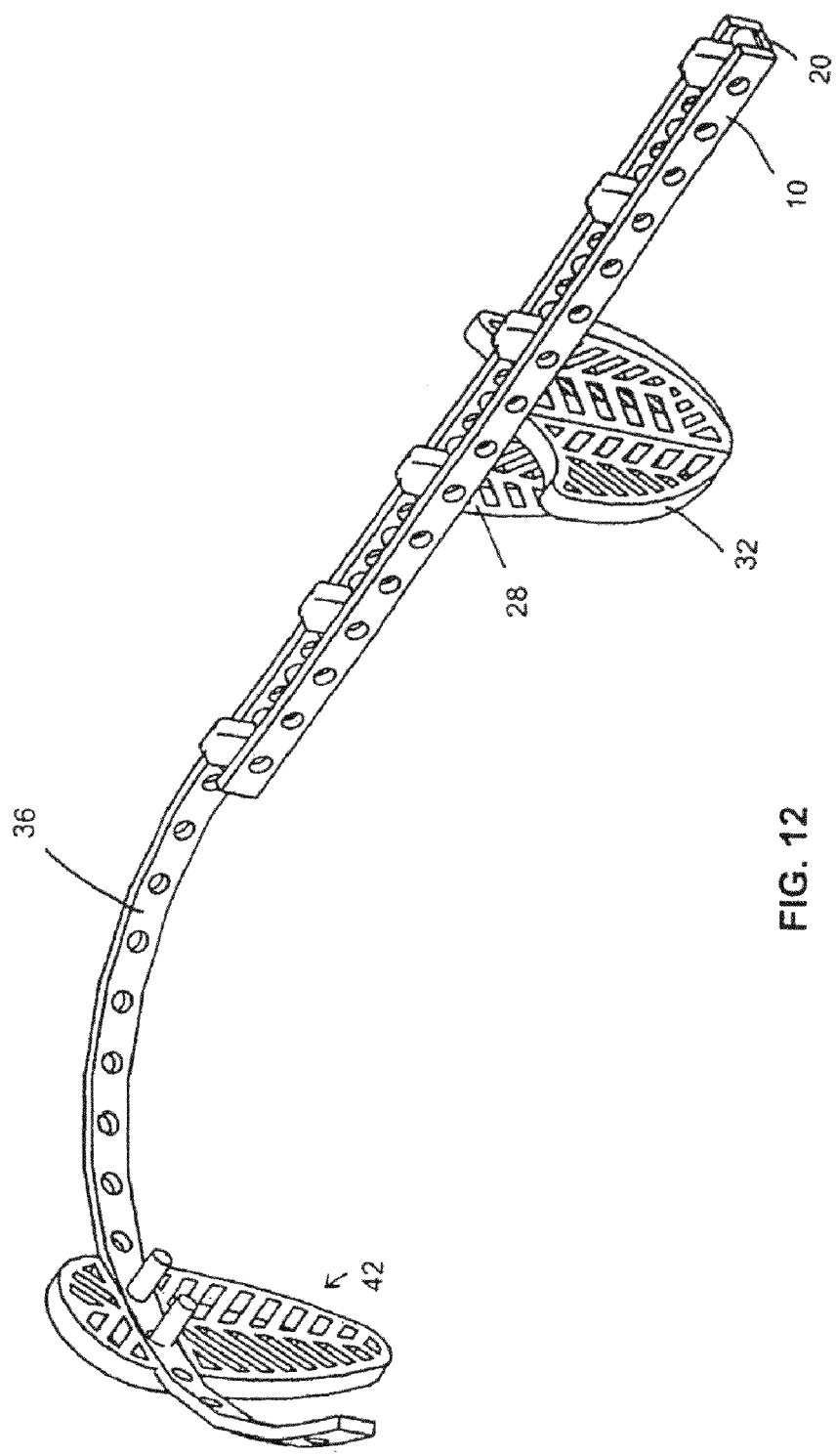
FIG. 12 is a perspective view of the bridge and reinforcing structure of FIG. 5 for supporting a pontic connected to the anterior perforated segment of FIG. 6 with the shield of FIG. 10 connected to the anterior perforated segment for supporting an anterior pontic.

Adding a shield 42 to the combination of the segment 36, bridge 35, and reinforcing structure 34 of FIG. 9, FIG. 12 shows the framework for supporting an anterior pontic. The shield 42 is connected to the segment 36 in a manner similar to the reinforcing structure 34 being connected to the bridge 35 for supporting respective pontics. This arrangement of FIG. 12 allows for the bonding of an anterior pontic in the anterior portion of the mouth and the bonding of an additional pontic on a first side of the mouth.

Figure 13B:
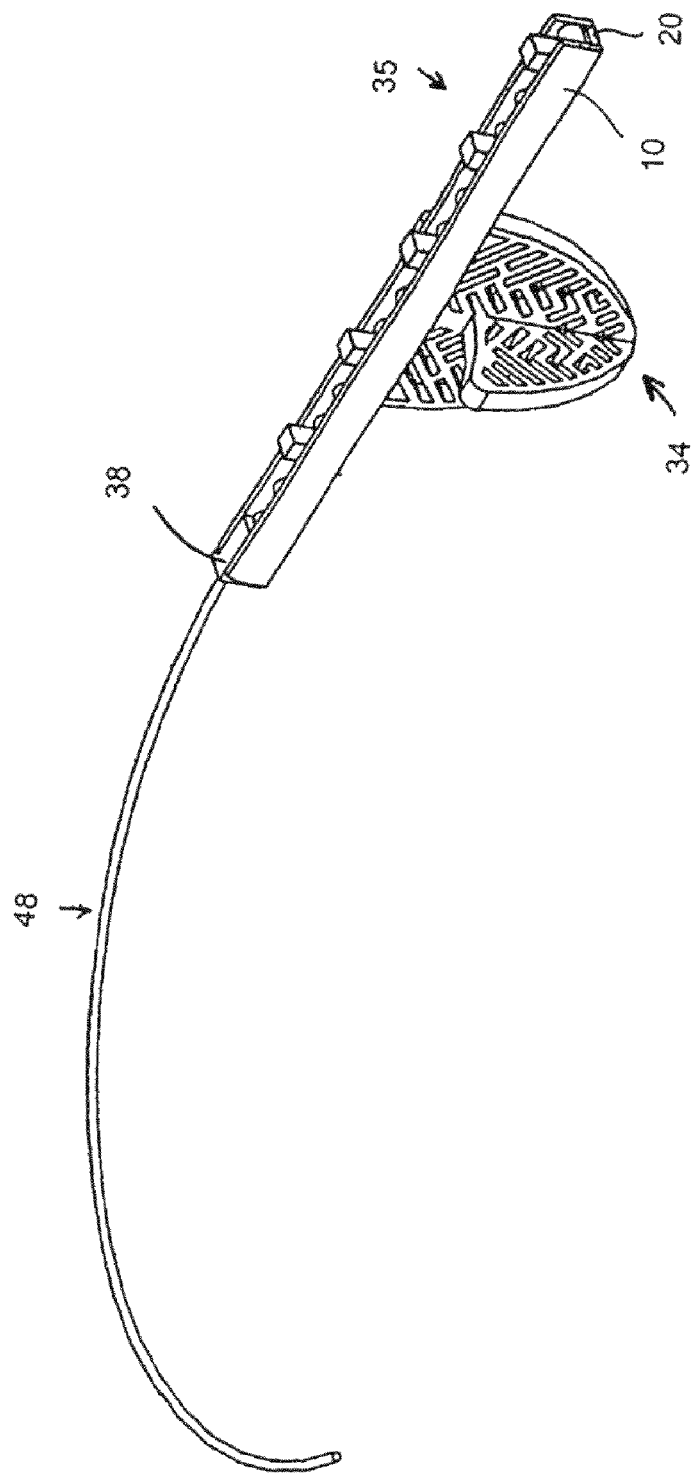
FIG. 13b is a perspective view of the combination of the anterior arch wire shown in FIG. 13 connected to the bridge and reinforcing structure shown in FIG. 5.

FIG. 13 shows an anterior arch wire 48 to be connected or locked into the bridge 35, and FIG. 13b shows the arch wire 48 locked into the bridge 35. The arch wire 48 is an alternate to the segment 36 for anterior support used alone or in combination with the side ladders 10. FIG. 13a shows the detail of the arch wire 48 locking into the ladder 10. The anterior arch wire 48 is connectable to the bridge 35 in the same manner as the segment 36 by using connection piece 38. The slot of the connection piece 38 receives a first rung 14 in a direction transverse to the axis, and the second recess receives a second rung 14 in a direction parallel to the axis. Also, a portion of the connection piece 38 may engage an end portion of the truss 20.

In the illustrated construction, the arch wire 48 is a solid wire as opposed to the segment 36 with perforations 40. The arch wire 48 can have a variety of applications including, for example, supporting anterior teeth that may be loose or maintaining alignment of anterior teeth. The arch wire 48 can be bonded to the back of a row of teeth, as understood in the art.

Figure 14:
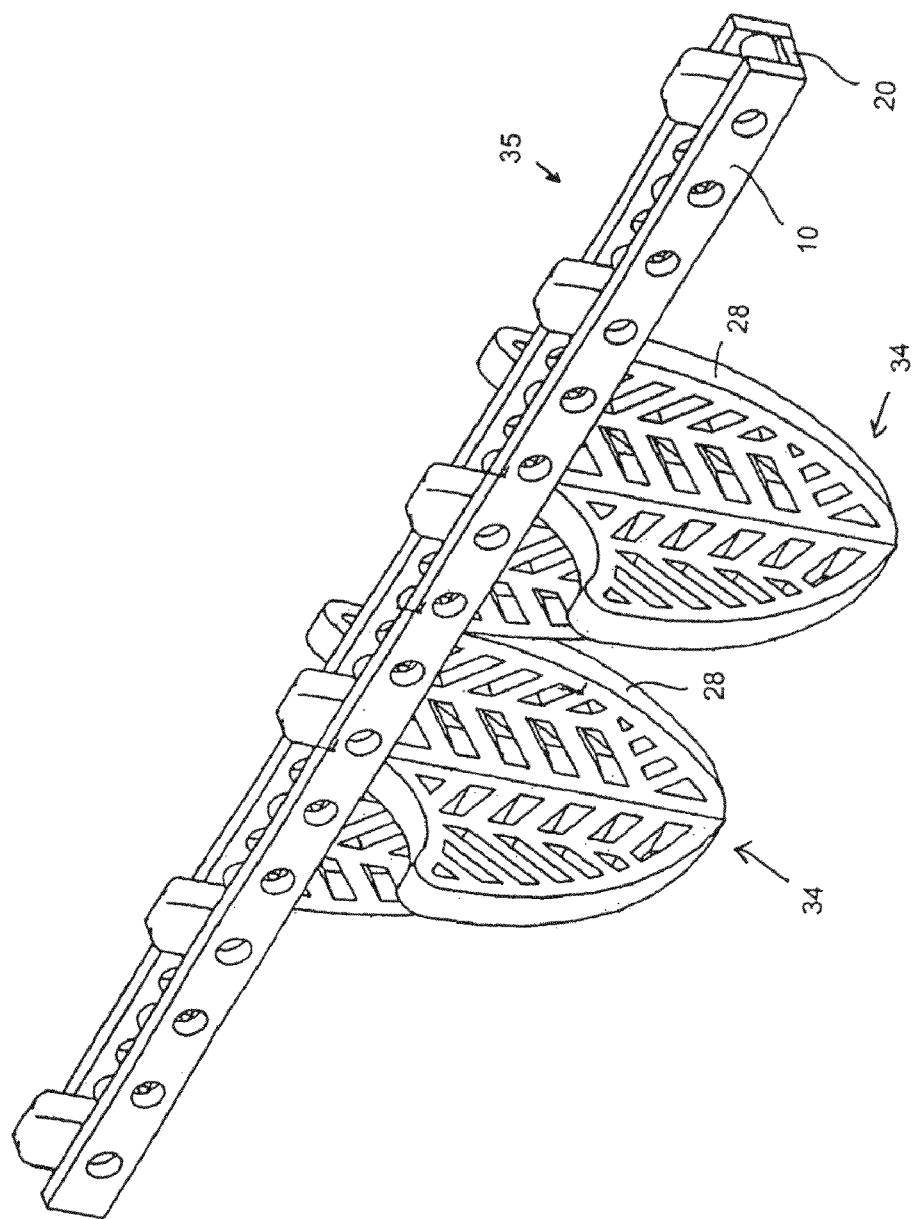
FIG. 14 is a perspective view of two reinforcing structures supported by the bridge shown in FIG. 5.
Figure 14A:
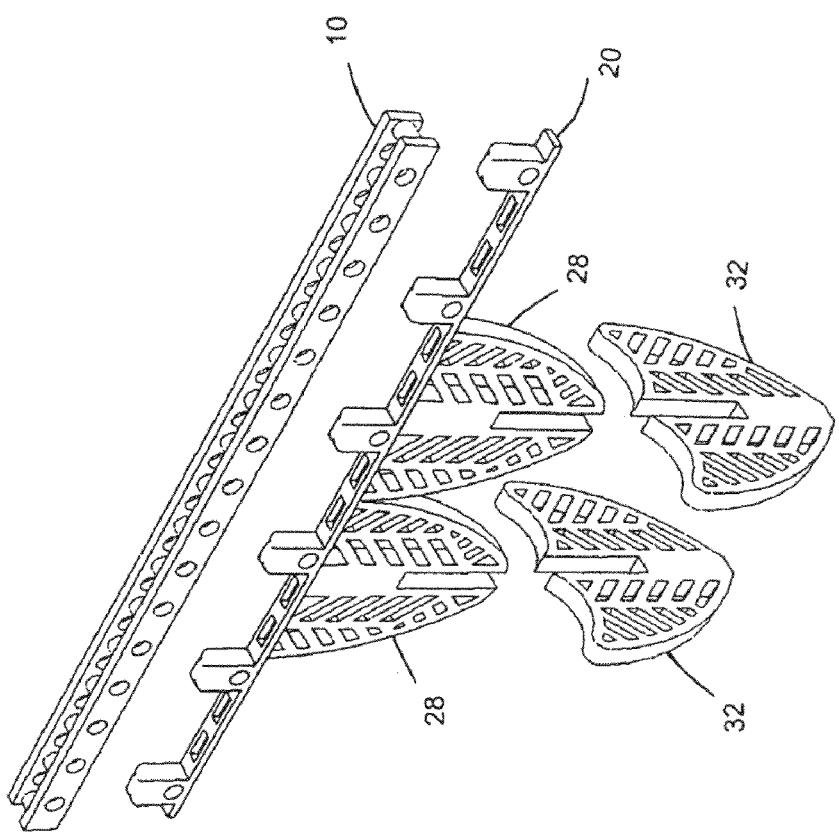
FIG. 14a is an exploded view of the assembly shown in FIG. 14.
Figure 14B:
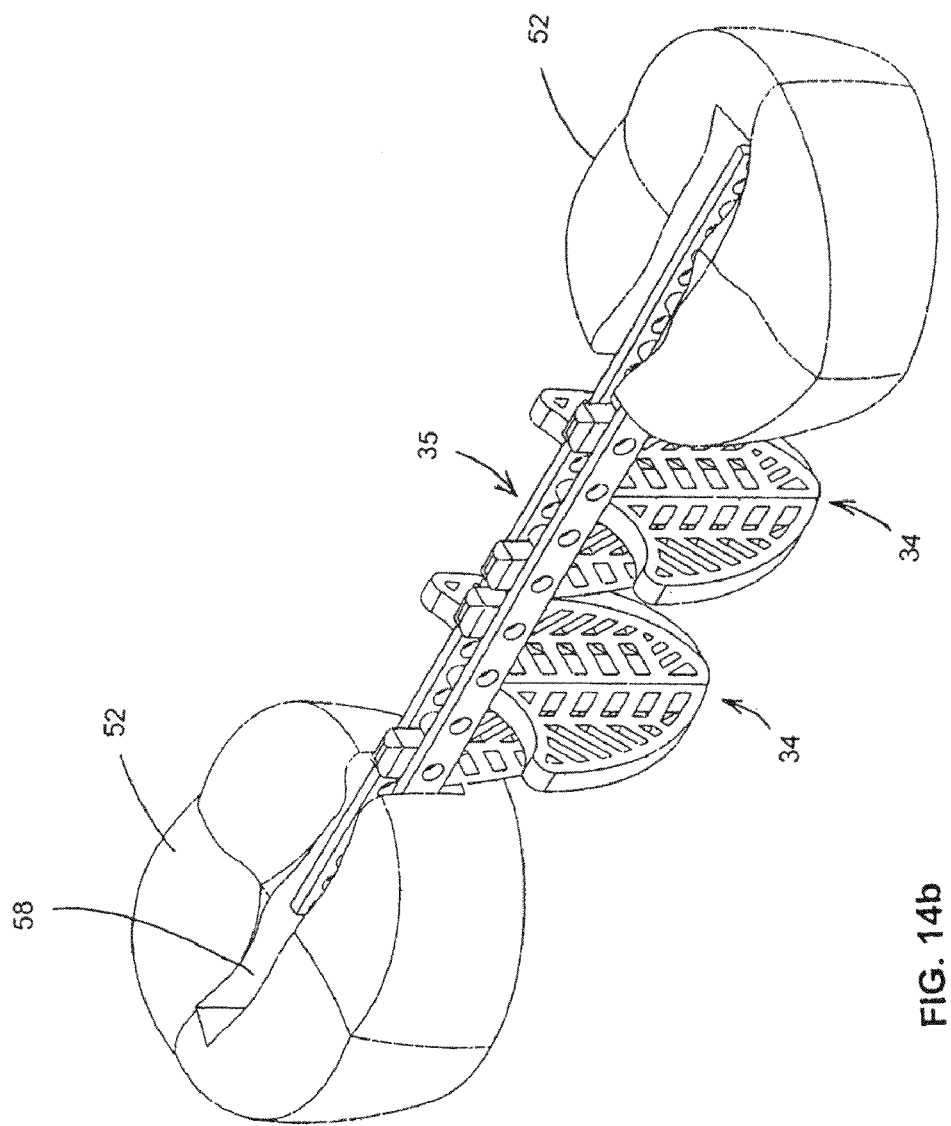
FIG. 14b is a perspective view of the assembly of FIG. 14 attached to two surrounding teeth.

FIGS. 14, 14a and 14b show two reinforcing structures 34 supported by bridge 35. Two or more reinforcing structures 34 (arranged side by side or otherwise) may be used in this system because of the reinforcing nature of the bridge 35 provided by the truss 20 interlocking with the ladder 10. In the illustrated construction and in some aspects, this combination increases the compressive strength and resistance to torquing of the pontic provided by the substructure 28, which may be formed of metal or another material. The strength of the bridge 35 may also be increased by splinting as many teeth as possible to stabilize the pontic. In other words, the more abutments incorporated on either side of the reinforcing structure 34, the stronger the bridge 35.

Figure 15:
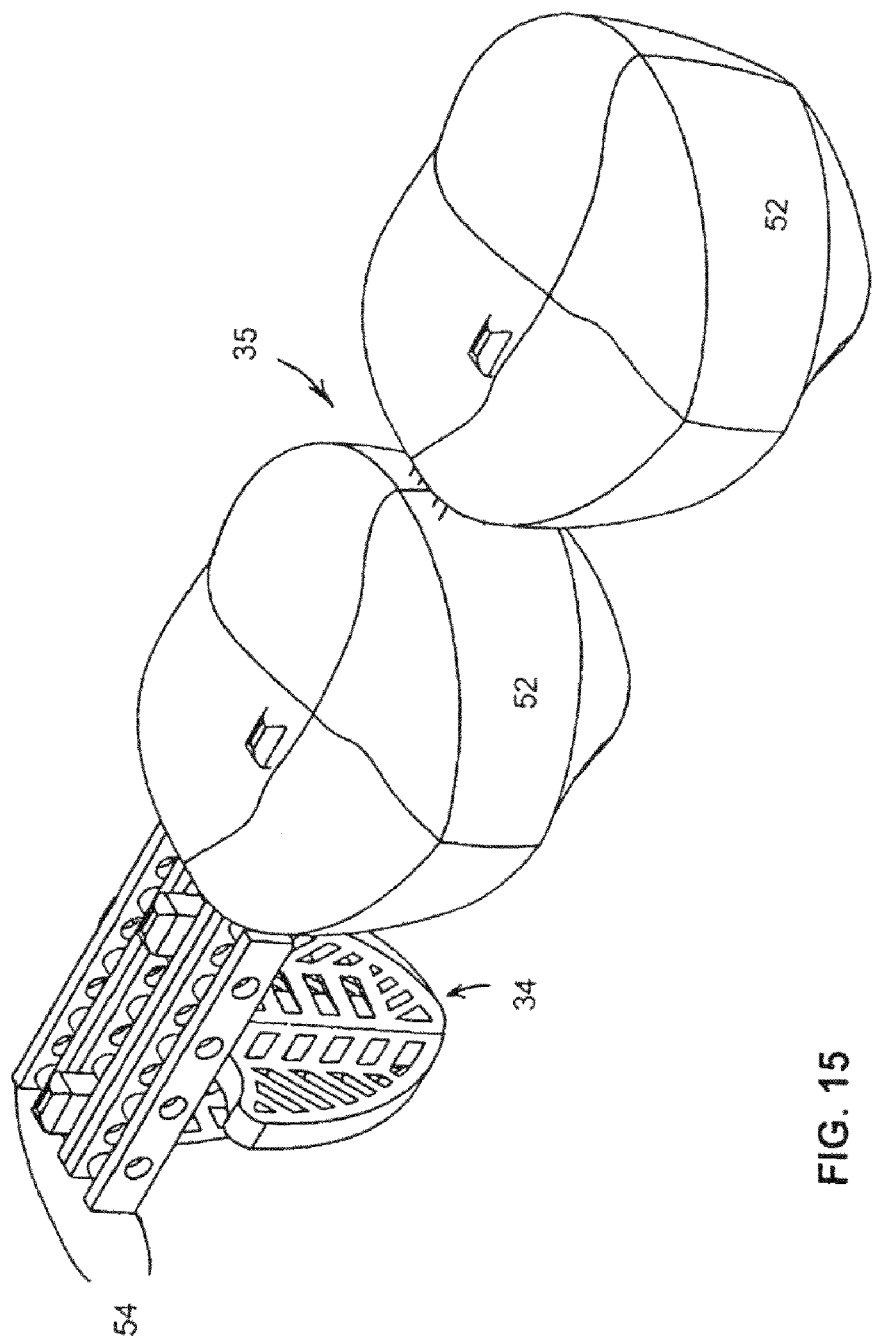
FIG. 15 is a perspective view of another construction of the bridge shown in FIG. 5 with one reinforcing structure for supporting a pontic with the bridge inserted into an adjacent tooth and an internal view of the bridge inserted into a tooth on the right.
Figure 15A:
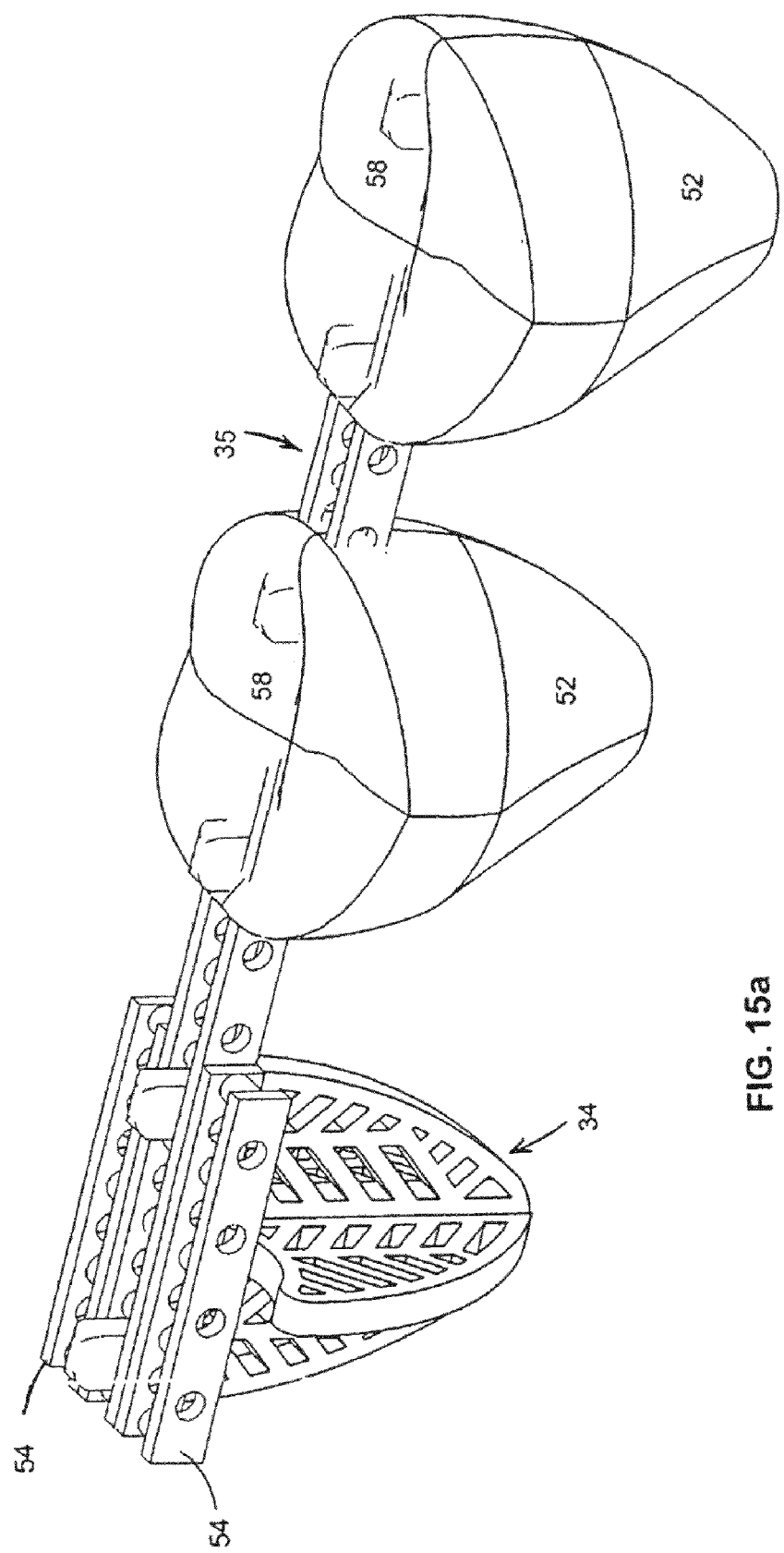
FIG. 15a is a perspective view of the assembly shown in FIG. 15 with the external view of the bridge inserted into the tooth on the right.
Figure 15B:
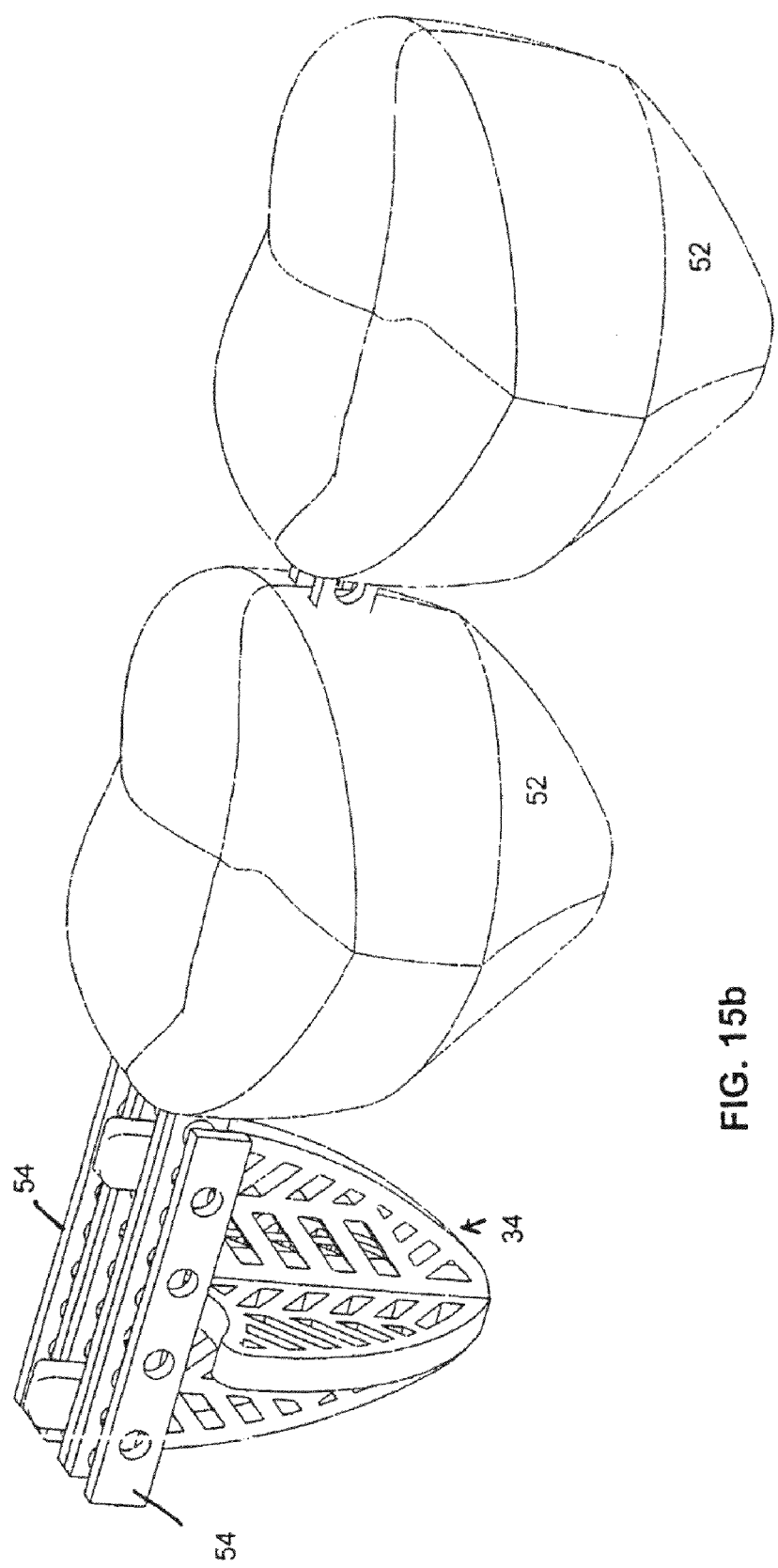
FIG. 15b is a perspective view of the assembly shown in FIG. 15 with the middle and right teeth filled with composite resin to enclose the bridge.

FIGS. 15, 15a and 15b illustrate the bridge 35 with one reinforcing structure 34a for supporting a pontic with the bridge 35 inserted into an adjacent tooth 52 and an internal view of the bridge 35 inserted into a tooth 52 on the right. Referring to the tooth 52 in the middle, composite resin has been partially added near the bridge 35 with a goal of bonding the bridge 35 to the middle tooth 52. This is, in effect, a prefabricated, performed composite bridge 52, which can be manufactured and supplied to dentists before a patient actually needs this bridge 35. In other words, this preformed bridge 35 could be kept in storage until the appropriate time. This preformed bridge 35 could be bonded wherever a bicuspid or molar is missing. With reference to the reinforcing structure 34 on the left side, additional ladder inserts 54 with perforations 16 are shown running parallel to the ladder 10 to provide, for example, increased bonding surface area, increased strength, etc.

Figure 16:
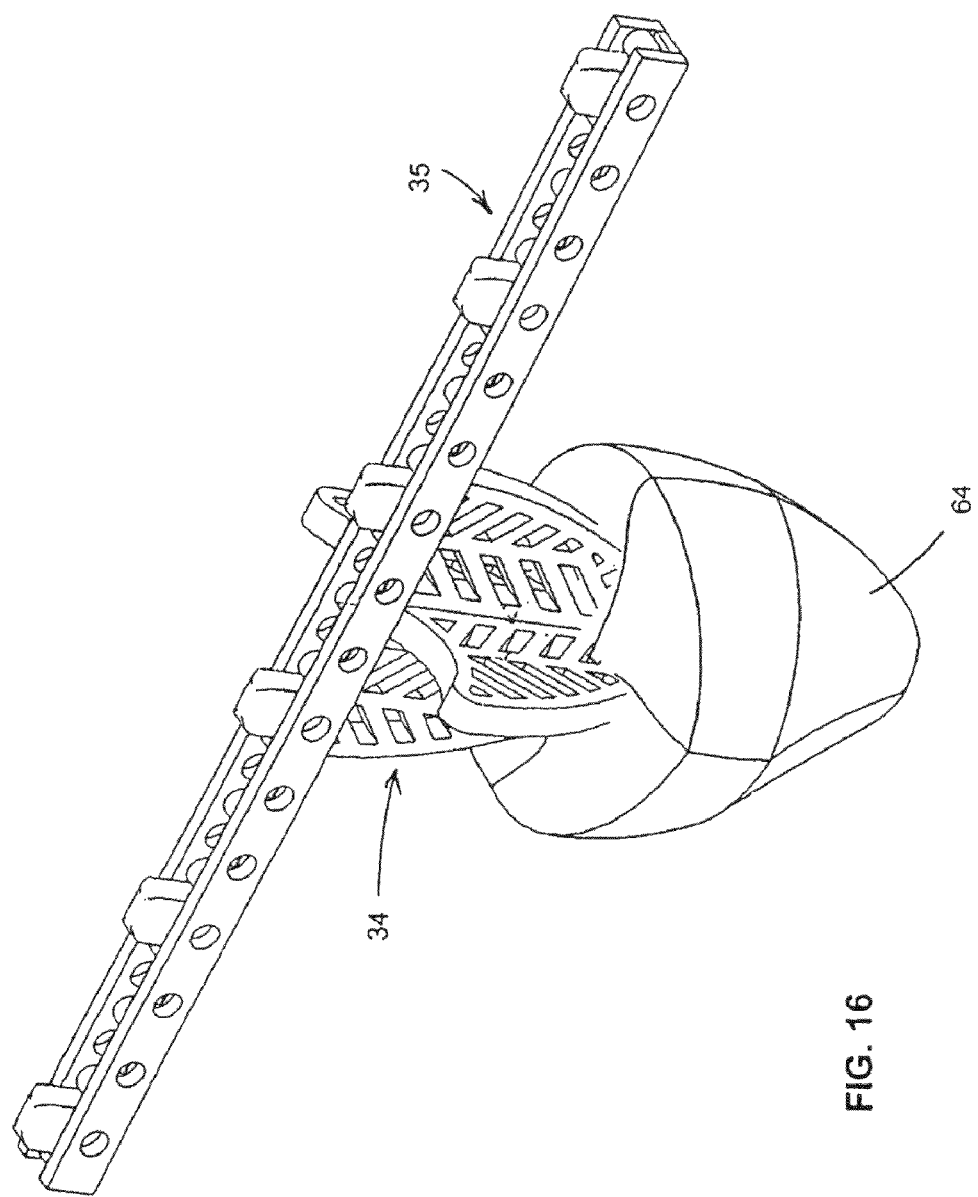
FIG. 16 is a perspective view of an assembled bridge and reinforcing structure shown in FIG. 5 during the process of inserting a pontic onto the reinforcing structure.
Figure 16A:
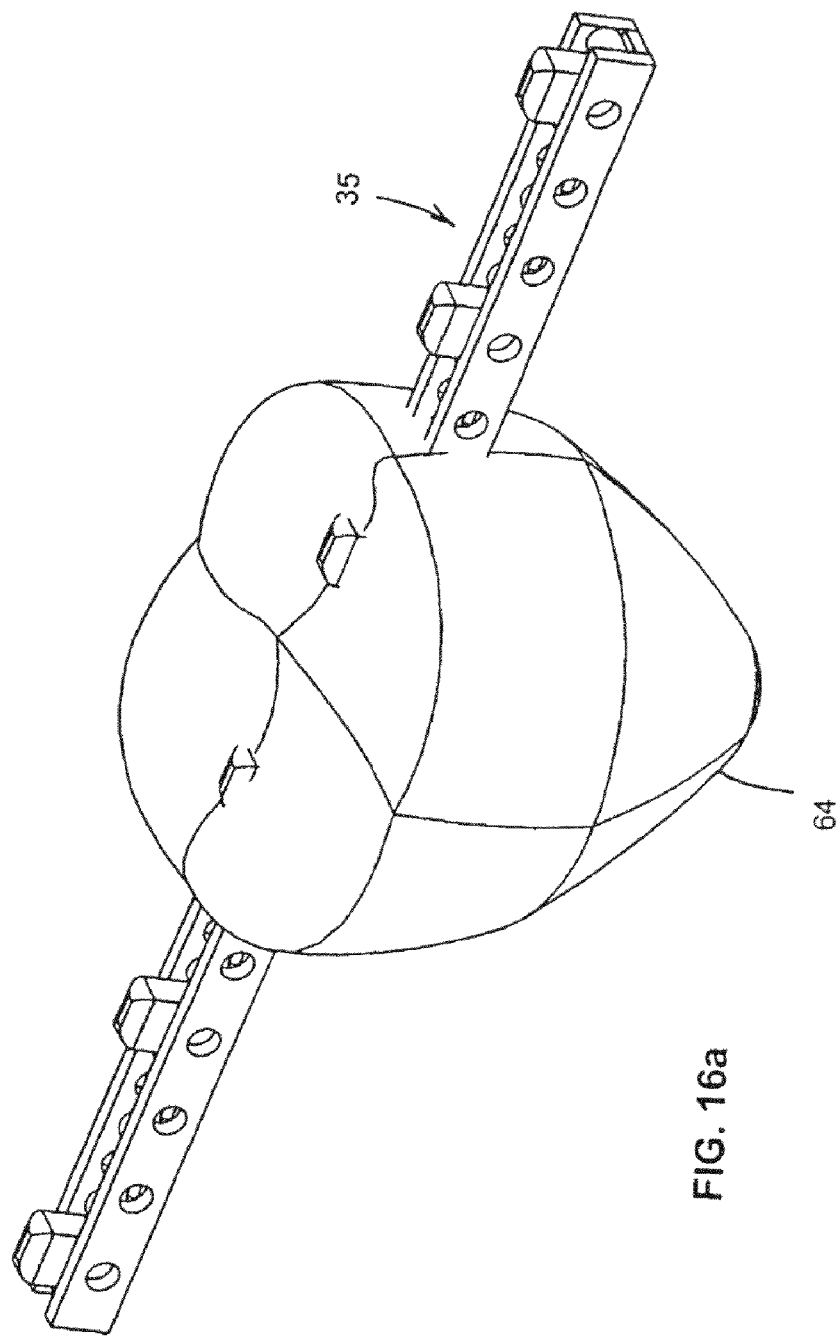
FIG. 16a is a perspective view of the assembly shown in FIG. 16 with the pontic completely inserted onto the reinforcing structure.
Figure 17:
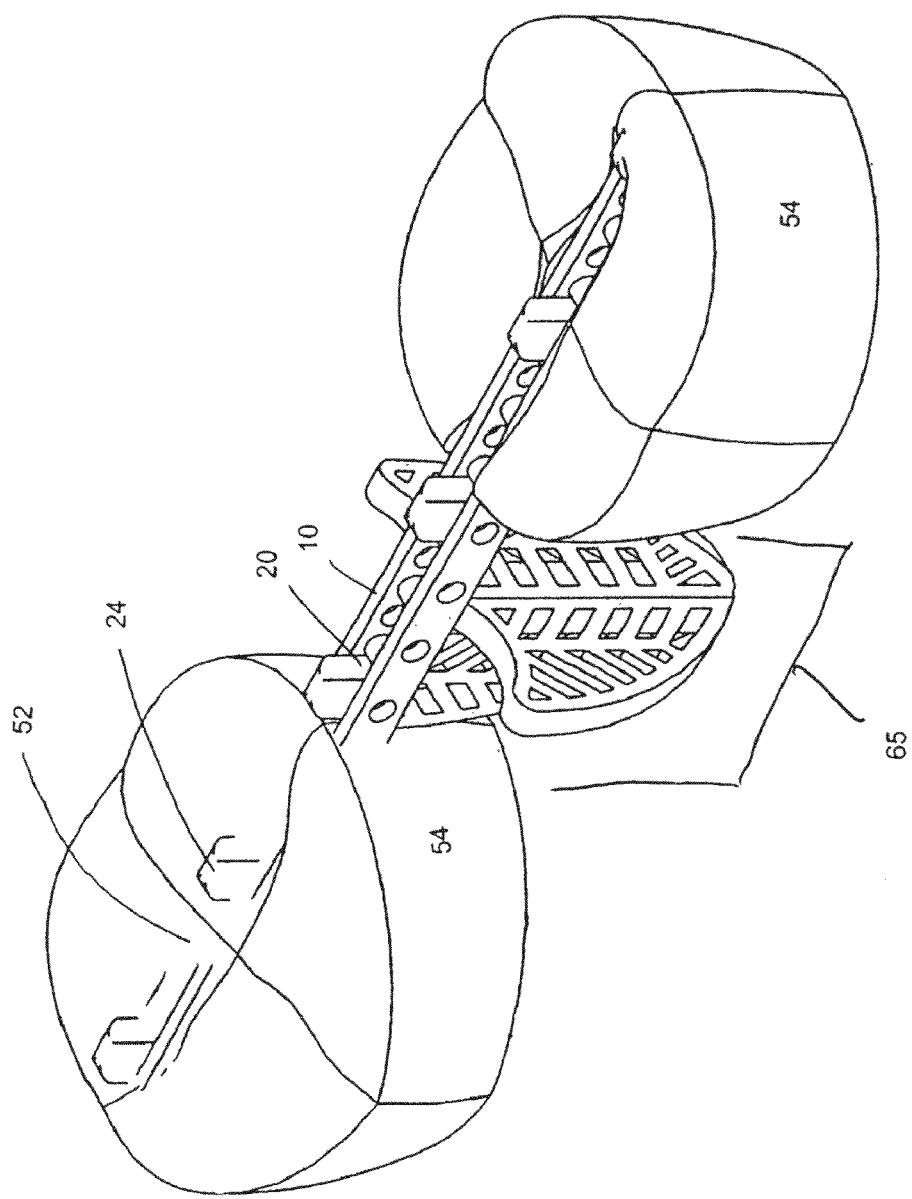
FIG. 17 is a perspective view of another arrangement of a bridge and reinforcing structure inserted in an edentulous space between two teeth with the tooth on the left filled with composite resin.
Figure 17A:
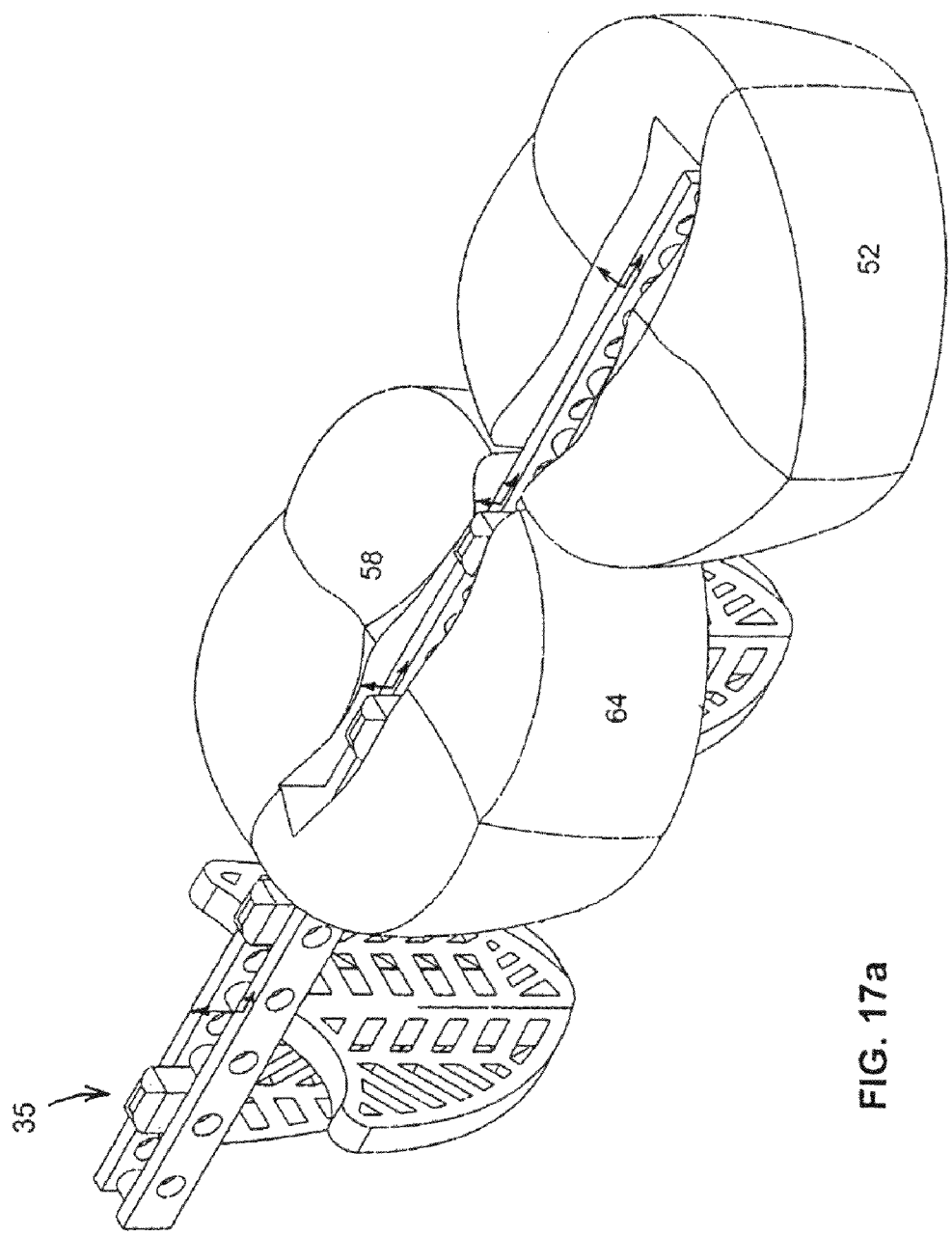
FIG. 17a is a perspective view of another arrangement of a bridge with two reinforcing structures adjacent to one another, the middle reinforcing structure coupled to a pontic partially filled with composite resin and adjacent to a tooth.

FIGS. 16 and 16a show the bridge 35 and the reinforcing structure 34 during the process of inserting a pontic 64 onto the reinforcing structure 34. Pontics 64 used with the illustrated constructions of the bridge 35 can have various sizes. The pontic 64 illustrated in FIG. 16 is of an average size. FIG. 17 shows the bridge 35 and the reinforcing structure 34 inserted in an edentulous space 65 between two teeth 52 with the tooth 52 on the left filled with composite resin 58. FIG. 17 also shows, on the tooth 52 on the left, projections 24 showing through the composite resin 58. The projections 24 may be formed of metal or another material.

Figure 18:
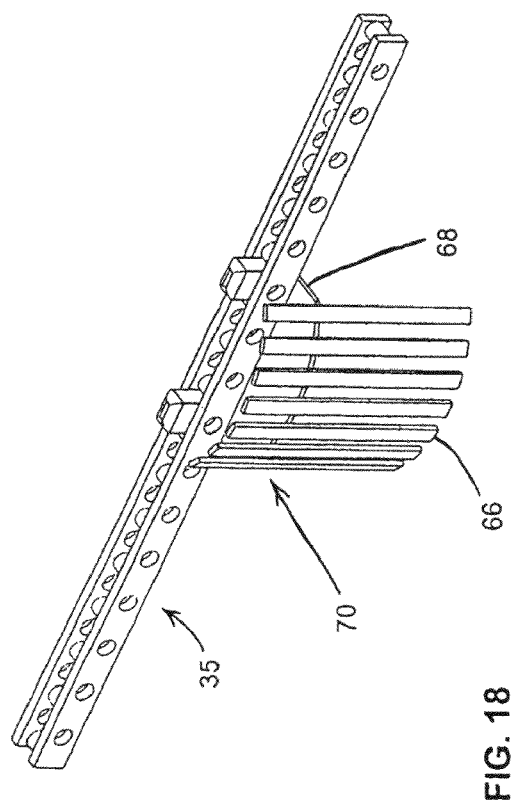
FIG. 18 is a perspective view of a temporary or permanent bridge abutment lingual finger reinforcement.
Figure 19:
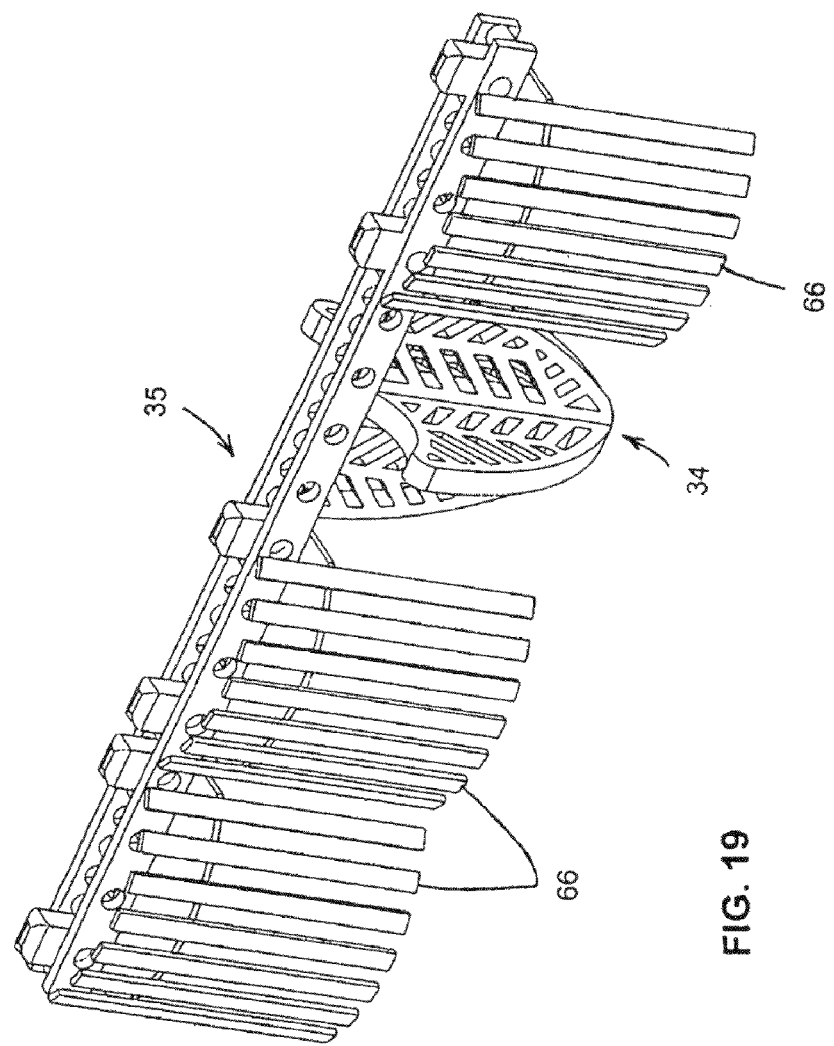
FIG. 19 is a perspective view of multiple permanent bridge abutment lingual finger reinforcements adjacent to a reinforcing structure coupled to the bridge as shown in FIG. 5.
Figure 20:
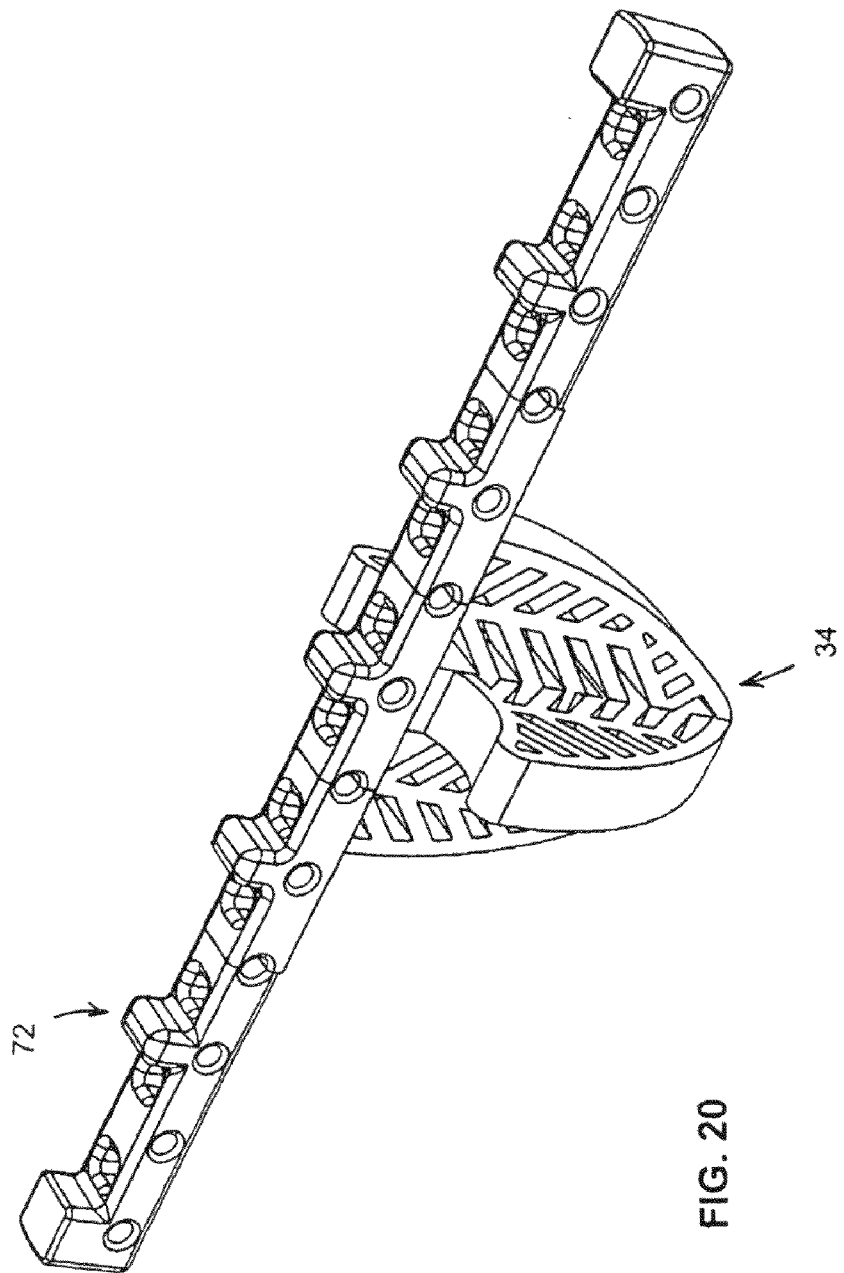
FIG. 20 is a perspective view of a bridge with a reinforcing structure as shown in FIG. 5.
Figure 20A:
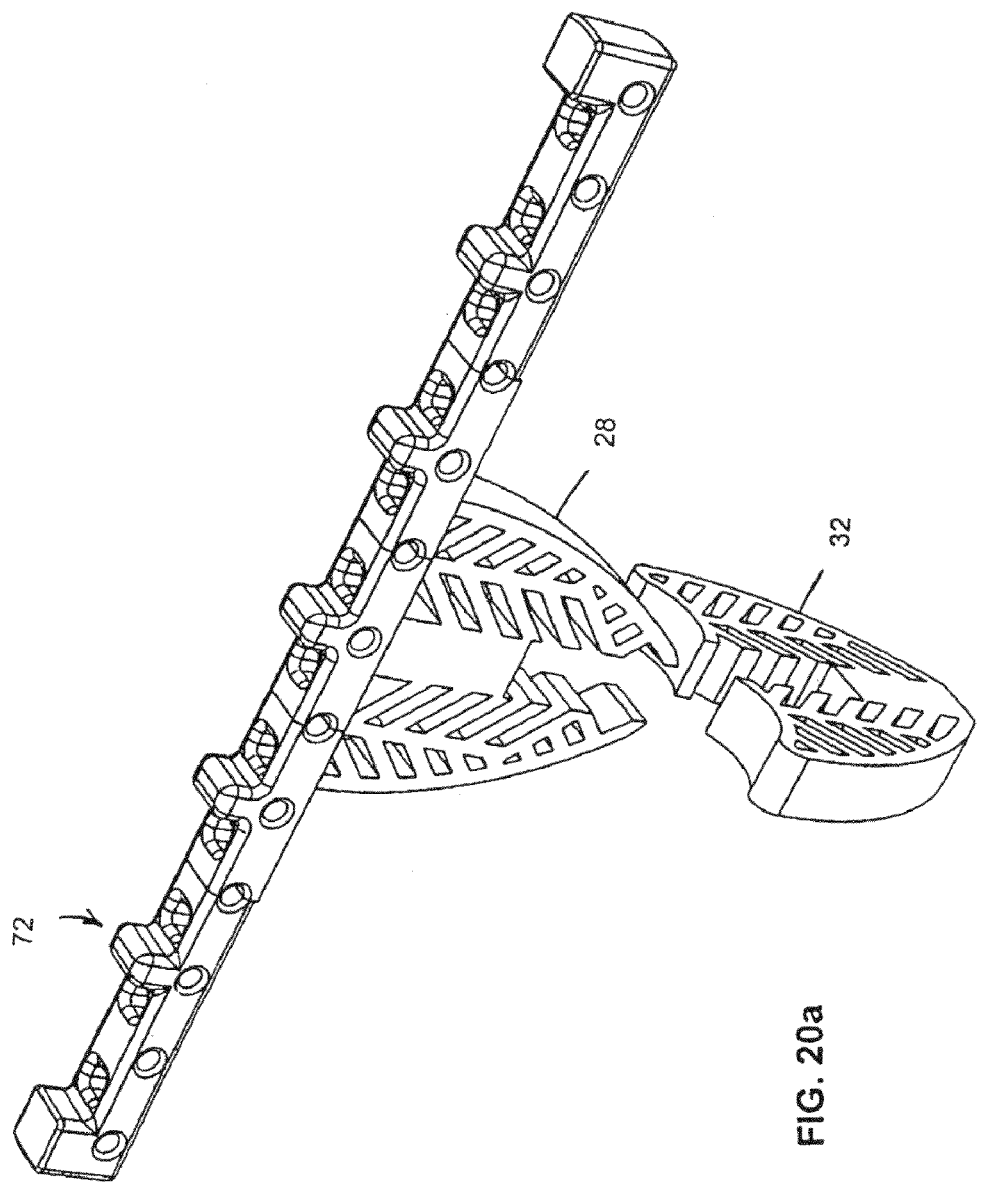
FIG. 20a is an exploded view of the assembly shown in FIG. 20.
Figure 20C:
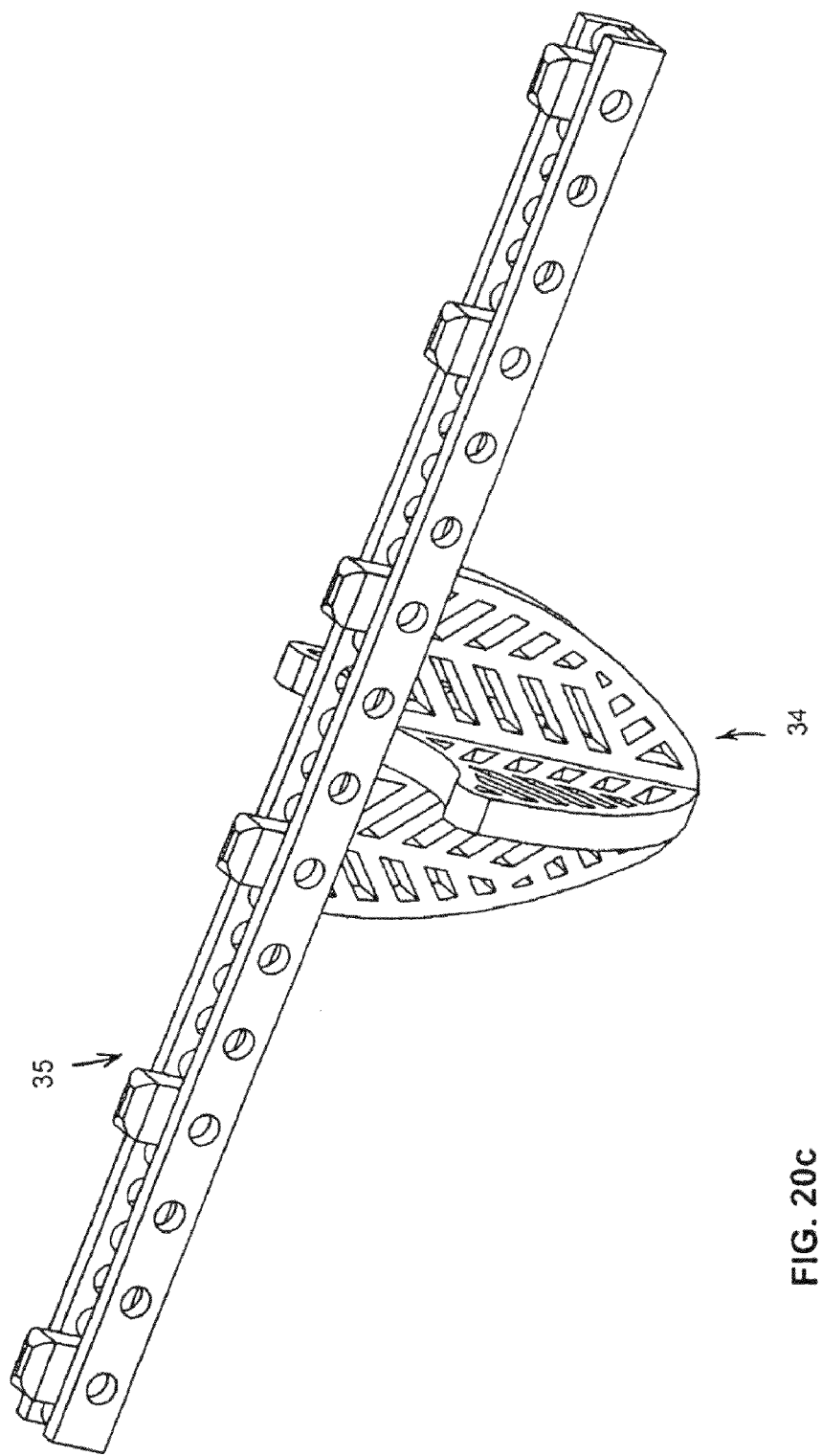
FIG. 20c is an assembled view of the construction shown in FIG. 20b before the bridge has been formed, for example, by casting.
Figure 20D:
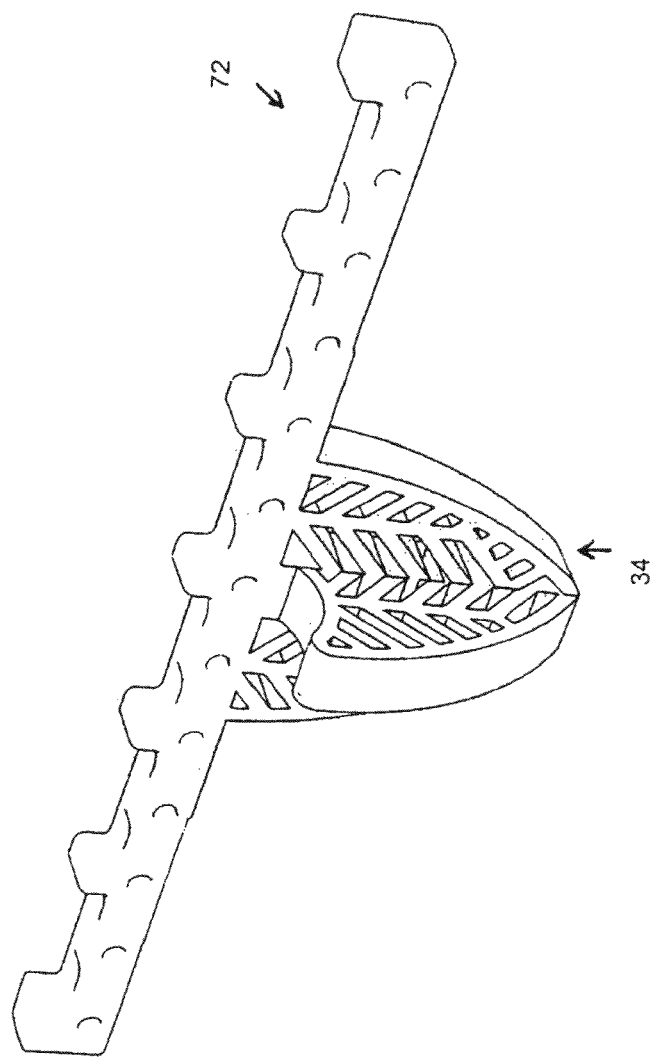
FIG. 20d is an assembled view of the construction shown in FIG. 20b of the bridge and reinforcing structure.

With reference to FIG. 18, lingual fingers 66, such as those illustrated, can be adapted to bridge 35. The lingual fingers 66 are attached to a plate 68 to form a lingual finger reinforcement 70, the combination adapted to be coupled to the bridge 35. As shown, the reinforcement 70 slides into the side apertures or perforations 16 in the rails 12. However, many alternate methods of attaching the reinforcements 70 to the bridge 35 are possible. The reinforcements 70 sit lingual to the prepared teeth (e.g., molar, bicuspid, cuspid, lateral, and central). FIG. 19 shows lingual fingers 66 that can be adapted around three teeth. Lingual fingers 66 can be used in a variety of situations, including but not limited to, adjacent to a reinforcing structure 34, adjacent teeth 52, adjacent to two reinforcing structures 34, etc.

FIGS. 20 and 20a-20d show a bridge 72 with reinforcing structure 34. The ladder 10 and truss 20 are merged into a one piece flat plane bridge 72. The bridge 72 may be made, for example, by casting or another method, of an appropriate material, such as, for example, gold, titanium, laboratory processed composite, etc. The bridge 72 is imbedded into unpolymerized composite resin, and then the resin is tamped over and light-polymerized or cured. Thus, the bridge 72 will form the contact points, the marginal ridges, and the occlusal stops of a bonded, composite restoration.

Figure 21:
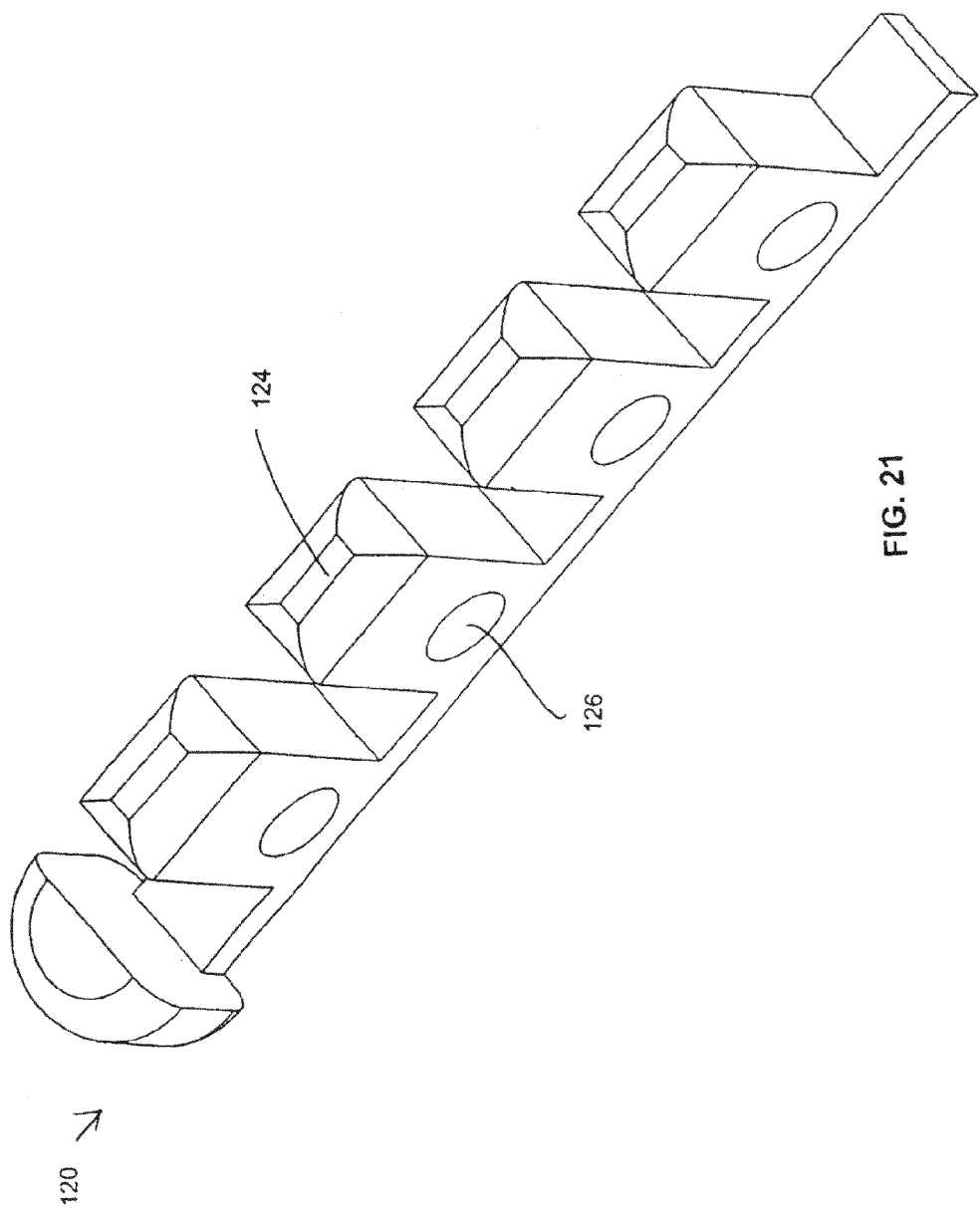
FIG. 21 is a perspective view of a truss for an insert for use in individual single composite restorations.

FIGS. 21-25 are an adaptation of one or more features of the present invention for use with individual single composite restorations. FIG. 21 illustrates a truss structure 120 similar to the truss structure 20 in FIGS. 1-20 for insertion into a single tooth. The truss structure 120 has a plurality of apertures 126 or perforations therethrough. The apertures 126 in the truss 120 can be round and are distributed to, for example, allow for the flow of composite resin. The truss 120 also has projections 124 to, for example, act as occlusal stops.

Figure 23:
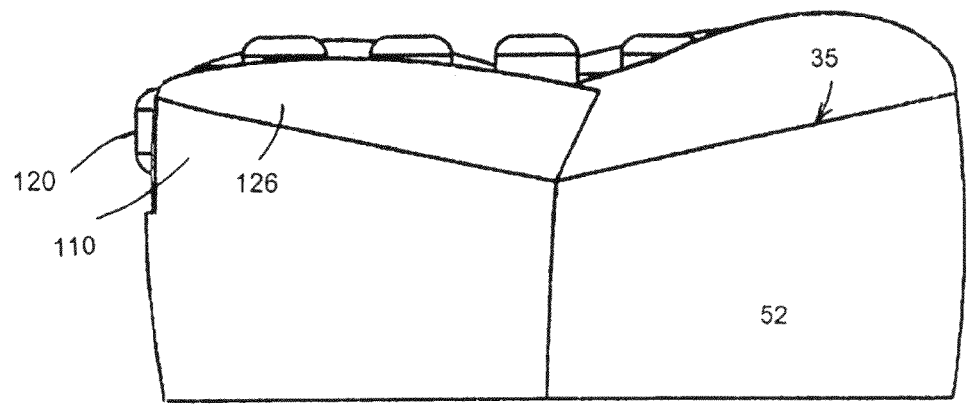
FIG. 23 is a side view of the combination shown in FIG. 22 inserted into a single tooth.
Figure 22:
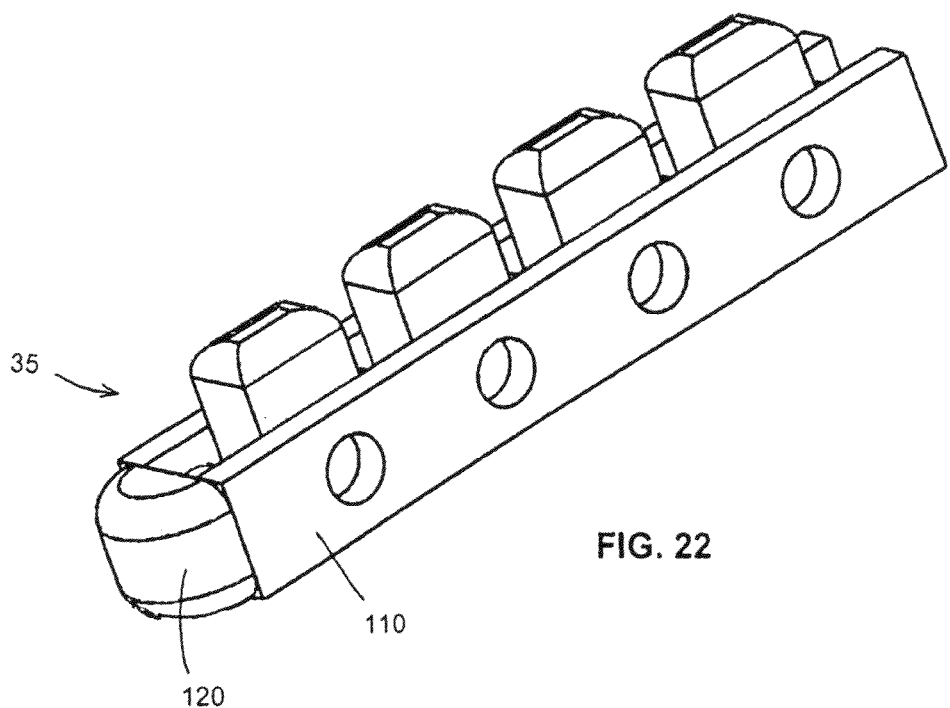
FIG. 22 is a perspective view of the truss shown in FIG. 21 connected to a ladder to form a bridge for an insert for use in individual single composite restorations.

As shown in FIG. 22, the projections 124 on the truss 120 may also be used for engagement through rungs 114 of a ladder 110. The ladder 110 is similar to the ladder 10 in FIGS. 1-20. In the illustrated construction, the projections 124 of the truss 120 in FIG. 22 fit through every rung 114 of the ladder 110, which is a preferred construction for a single insert composite restoration 108. However, depending on the size of the tooth and the size of the ladder 110, the projections 124 of the truss 120 may engage the ladder 110 between every rung, every other rung, or every third rung 114. The combination of ladder 110 and truss 120 forms a bridge 135, similar to the bridge 35 shown in the constructions of FIGS. 1-20. FIG. 23 shows the bridge 135 placed in into a single tooth. From an alternate view in FIG. 24, composite resin 58 will be allowed to flow around the entire system as well as into the apertures 126 of the truss 120 and ladder 110 insert as to bond with a tooth 52.

Figure 25A:
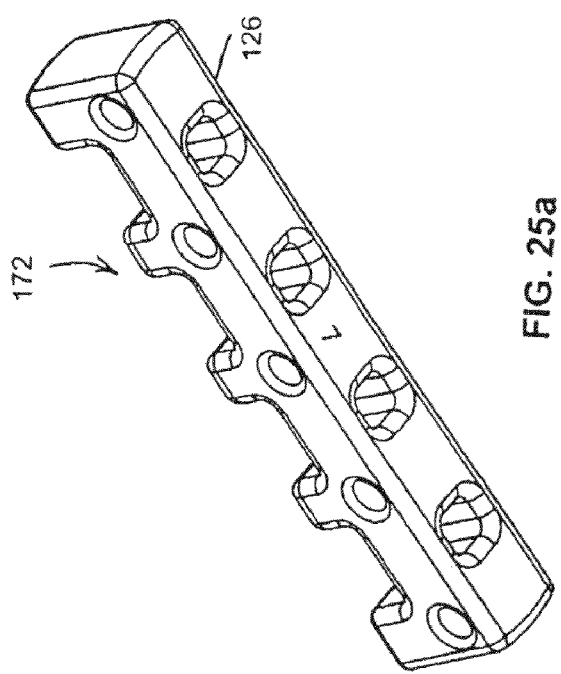
FIGS. 25a-25c are views of the insert shown in FIG. 25 for use in individual single composite restorations.
Figure 25B:
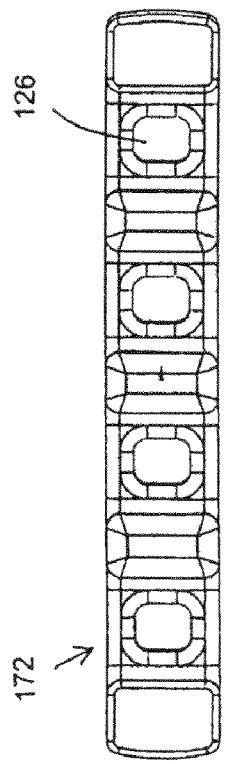
Figure 25C:
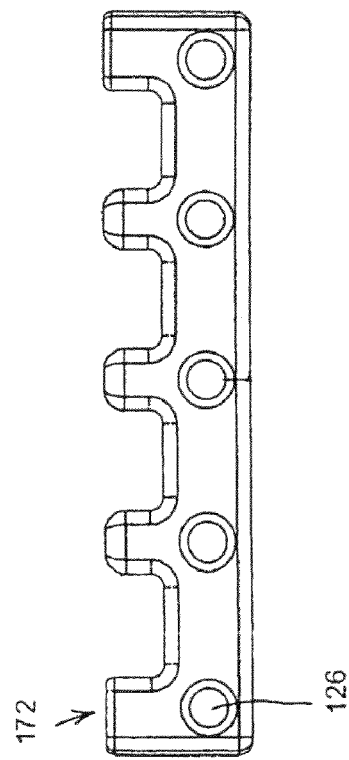
Figure 26:
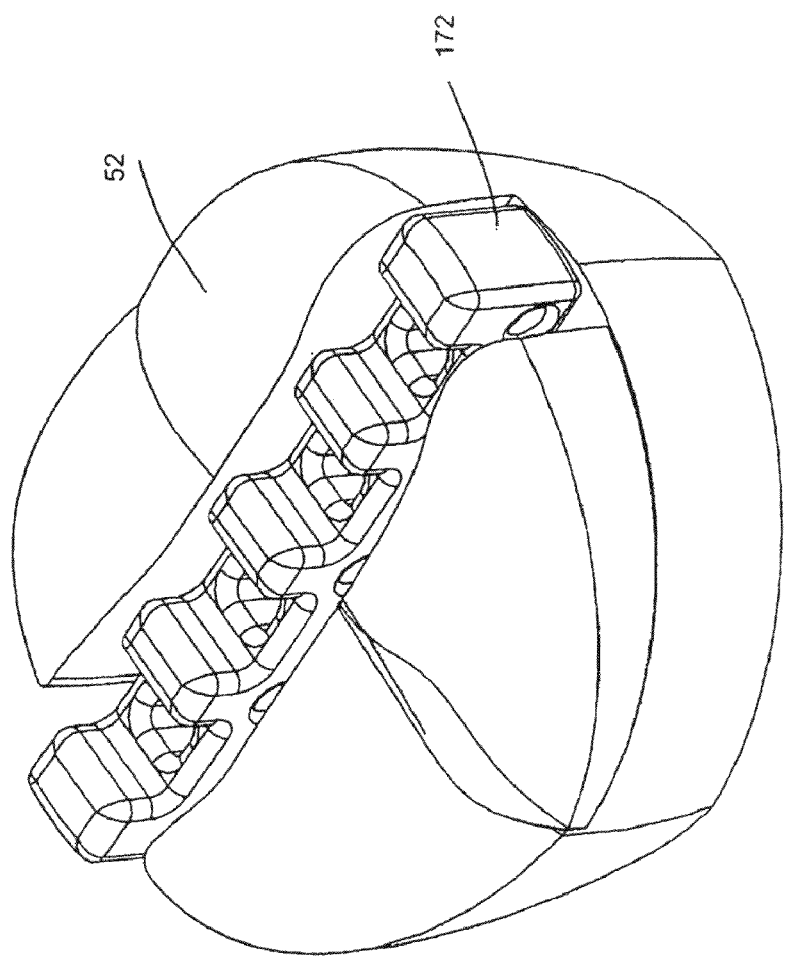
FIG. 26 is a perspective view of the insert shown in FIG. 25 inserted into a tooth that to which composite resin has been added for bonding to the tooth.
Figure 26A:
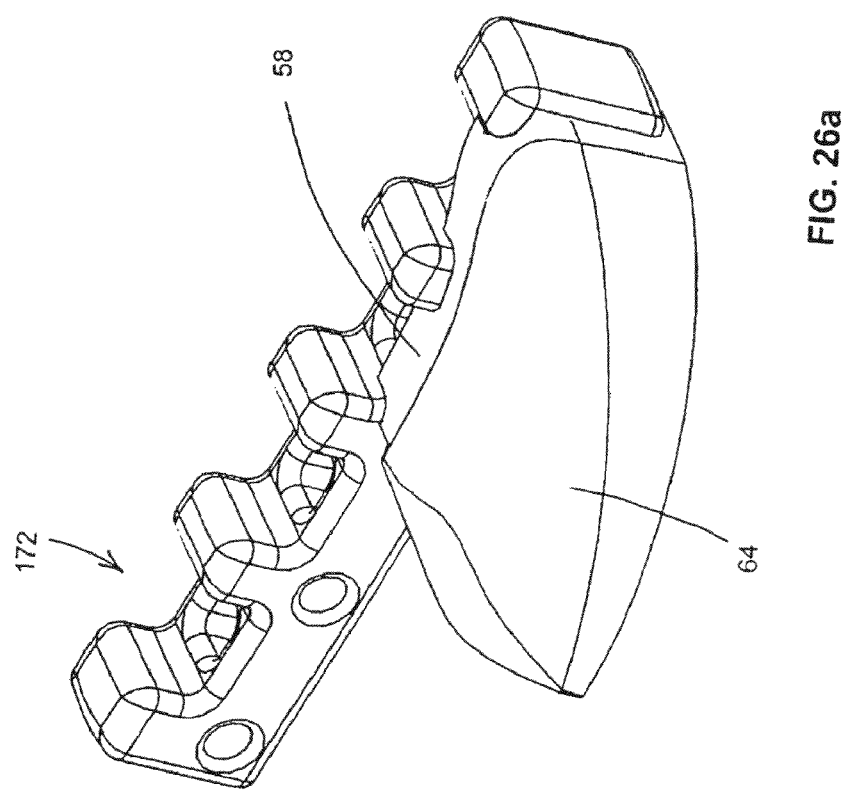
FIG. 26a is a perspective view of the insert shown in FIG. 25 with composite resin bonding a quarter of a pontic to the insert.
Figure 26C:
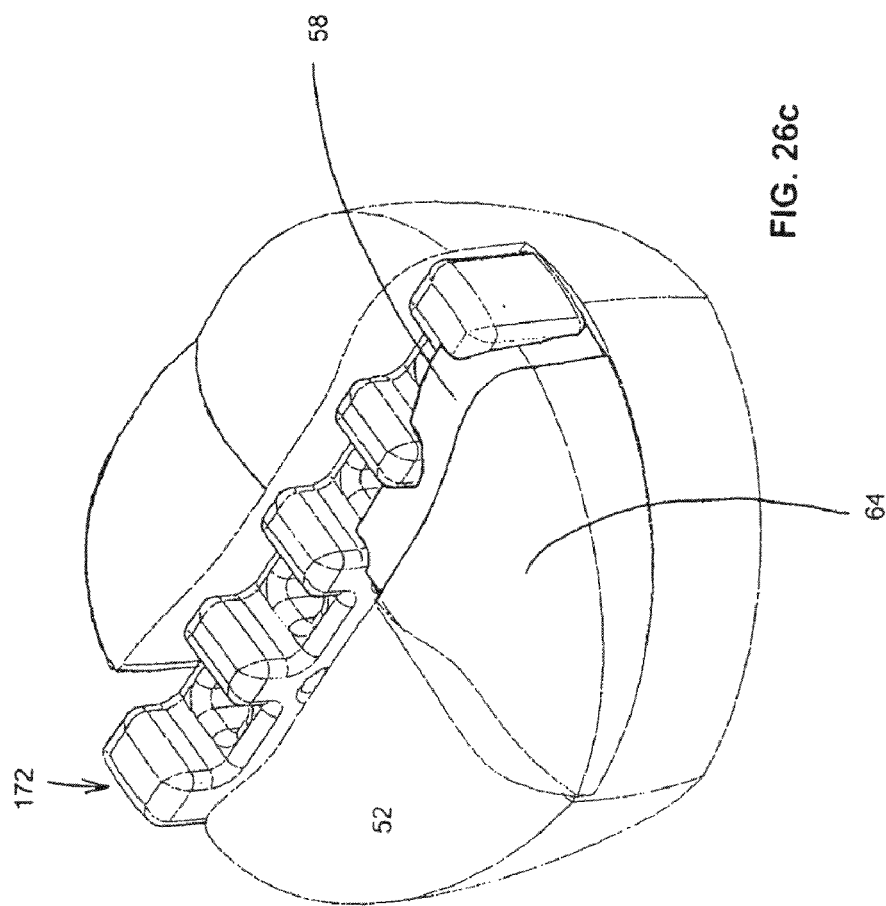
FIG. 26c is a perspective view of the insert bonded to a quarter of a pontic shown in FIG. 26a inserted into a damaged for bonding thereto.

FIG. 25 illustrates a finished version of an insert 172 for use in individual single composite restorations. The ladder 110 and truss 120 are merged into the one piece flat plane cast insert 172. The insert 172 can be made of an appropriate material, such as, for example, gold, titanium, laboratory processed composite, etc. The insert 172 is imbedded into unpolymerized composite resin and then the resin is tamped over and light-polymerized or cured. Thus, the insert 172 will form the contact points, the marginal ridges, and the occlusal stops of a bonded, composite restoration. The insert 172 includes multiple apertures 126 to, for example, allow resin to flow through and around the insert 172 in creating the composite restoration. FIGS. 25a-25c are multiple views of the insert 172 to illustrate the location of the apertures 126. The location of the apertures 126 is not limited to the locations shown. More or fewer apertures 126 can be incorporated into the insert 172 at nearly any location on the insert 172. FIGS. 26a-26c illustrate the insert 172 with composite resin bonding a quarter of a pontic to the insert 172.

Figure 27:
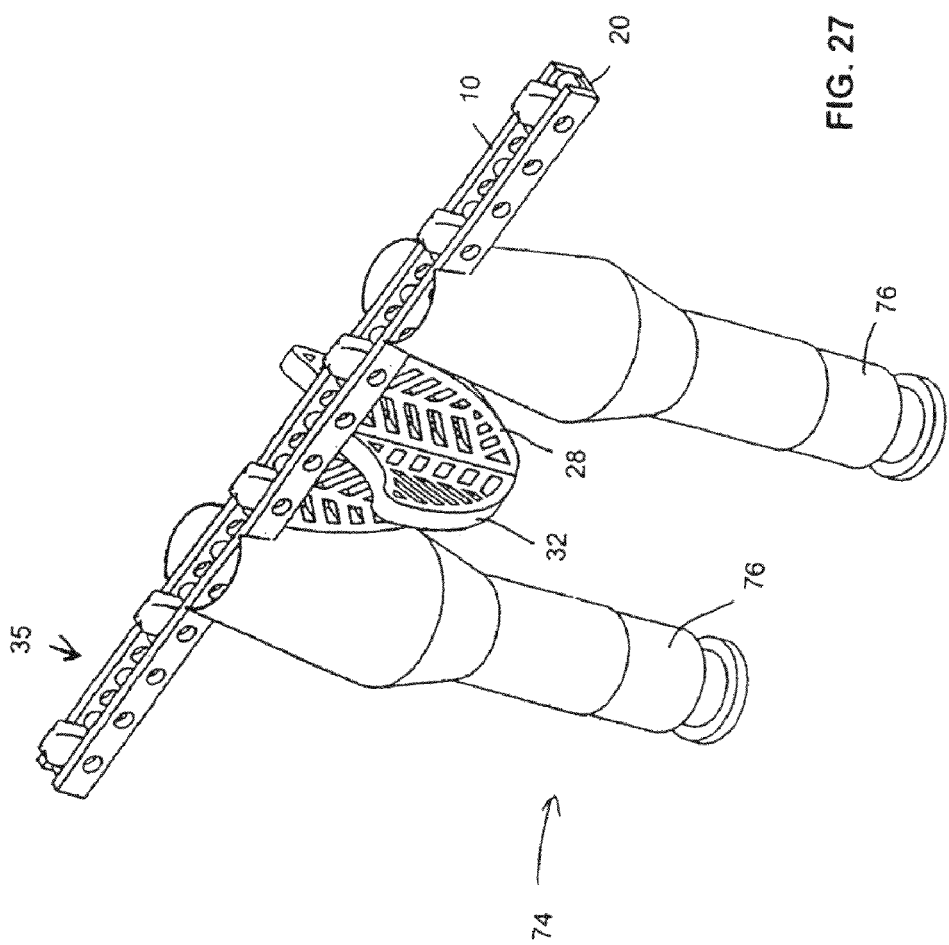
FIG. 27 is a perspective view of a bridge and reinforcing structure of FIG. 5 with connections for fitting into the jaw.
Figure 28:
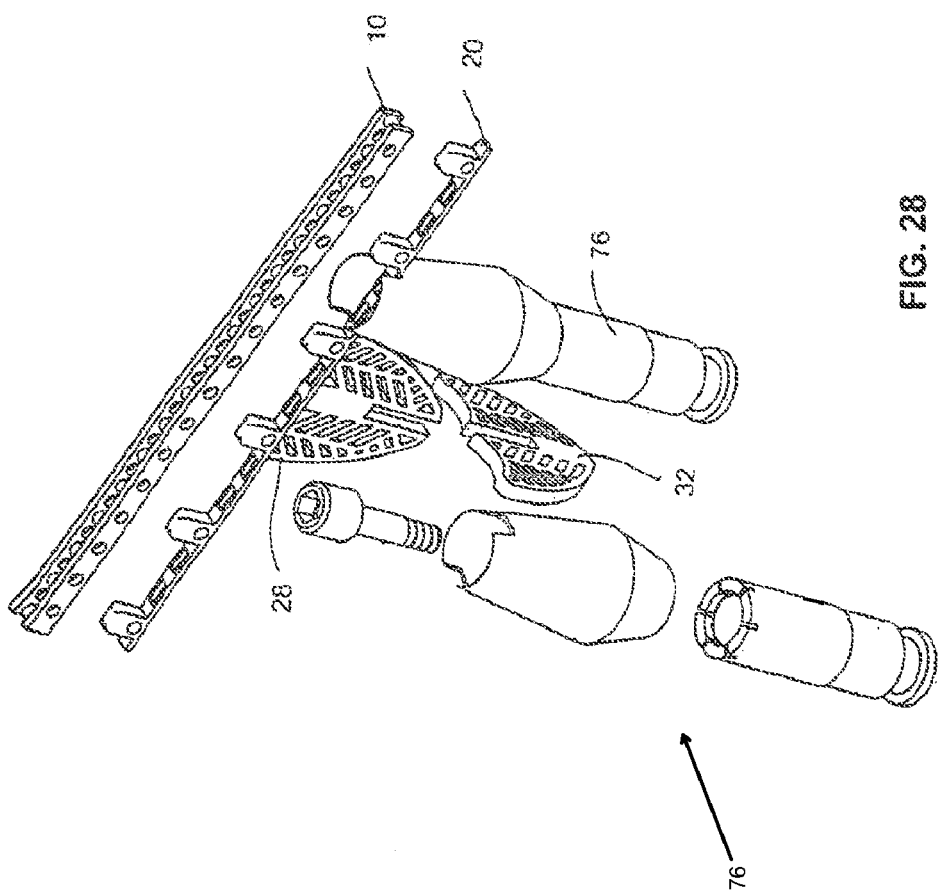
FIG. 28 is an exploded view of the assembly of FIG. 27.

FIG. 27 and FIG. 28 illustrate the bridge 35 adapted for an implant bridge 74 with implant legs 76. The implant legs 76 are adapted to be inserted into the jaw of a patient. The implant legs 76 fit around the outside of the ladder 10 and can be secured thereto. The implant legs 76 can be positioned at a variety of different locations along the length of the ladder 10. One or more reinforcing structures 34 can inserted between the legs 76 of the implant bridge 74.

In some independent aspects, a system for making and installing a temporary bridge, in which the dentist makes the temporary bridge chair side, is provided. The dentist first selects the appropriate length of the ladder 10 and snaps in a section of the truss 20 with one, two, three, or more reinforcing structures 34 depending on how many teeth are missing.

The dentist can select a reinforcement 70 that slides into the side apertures or perforations 16 in the rails 12. The fingers 66 sit lingual to the prepared teeth (e.g., molar, bicuspid, cuspid, lateral, and central), and the dentist sets a small amount of unpolymerized light-cured composite on the occlusal surface of the prepared teeth.

The dentist places the ladder 10, truss 20, and one or more reinforcing structures 34 into the unpolymerized light-cured composite. The dentist partially light-cures the resin without bonding the resin to the tooth. The dentist takes a vacuum-formed clear stent and fills it with acrylic or composite, then sets it over the ladder 10 and truss 20 on the prepared teeth, so that when the temporary bridge is removed, the ladder 10, truss 20, and pontic(s) are picked up because they are internally incorporated in the temporary bridge. The projections 24 on the truss 20 act as occlusal stops to prevent the wearing of the bridge. The temporary bridge is both reinforced and slow to wear occlusally to provide a long-term temporary bridge.

In contrast, in conventional dental bridges, the laboratory fashions the temporary bridge in a different manner. After receiving the study models and bite from the dentist, the laboratory prepares the designated teeth for crown preps. The laboratory selects the appropriate length and pontic size for the bridge and appropriate lingual reinforcement systems. The laboratory constructs the reinforced temporary bridge for placement by the dentist into the patient's mouth.

In some aspects, the system may eliminate any casting to be done because the individual components (e.g., the ladder 10, truss 20, substructure 28, etc.) can be a part of an extensive kit available to the dentist. For the reinforced single, double, or more pontic bridge, all the dentist has to do is send the laboratory a set of unprepared study models, a bite, and a shade. The laboratory can groove the MO, DO, MOD preps in the adjacent teeth and fabricate a trim coping for the dentist to follow. The laboratory can then fabricate the bridge. When the dentist receives the bridge, the dentist only needs to put the trim coping in the patient's mouth, groove the teeth, apply the bonding resin, put the composite into the grooves, press the ladder 10 and truss 20 into the composite, tamp it over, light-cure the ladder 10 and truss 20 into the composite, and finally adjust the occlusion.

The ladder 10 and truss 20 can be used in a variety of different applications. In one exemplary application, the ladder 10 and truss 20 can be used to stabilize mobile teeth up to and including an entire arch using just the ladder 10, or the ladder 10 in combination with the truss 20 or the truss 20 with the substructure 26 for anchoring the pontic. This is accomplished by embedding the ladder 10 and truss 20 into MO, DO, or MOD preparations in the teeth to be stabilized, in which unpolymerized composite resin has been placed. After seating the ladder 10 and truss 20, the resin oozes through the apertures or perforations 16 in the ladder 10 and the apertures 26 in the truss 20. After the resin is sufficiently set, it is tamped down and molded. The composite resin is then light cured or polymerized to create a permanent reinforced bridge.

As shown in FIG. 17, in an exemplary application in which two bicuspids are missing, the bridge 35 could be fabricated by splinting three molars together in the posterior. In another situation in which two anterior teeth are missing, two, three, or more teeth in the anterior (e.g., cuspid, lateral, etc.) could be splinted around the anterior arch if necessary. For the anterior portion of the mouth, if a tooth is missing, an anterior pontic could be fabricated out of composite and attached to the shield 42 with projections 44. The shield 42 and/or the projections 44 may be formed of metal or another material.

In another exemplary application, the interlocking ladder 10 and truss 20 with substructure(s) 28 and pontic(s) can be used to replace a missing tooth or teeth at any location over the arch. An artificial tooth or teeth can be formed around the substructure 28 by the dentist chair-side either free-hand or with celluloid pontic halves made from composite resin (light-cured or light-polymerized). The artificial tooth or teeth can also be fabricated in a dental laboratory by a dental laboratory technician. The resulting bridge is then bonded in two or more teeth after preparation of those teeth by the dentist and inserting the ladder 10 and truss 20 as previously discussed.

In yet another exemplary application, the interlocking ladder 10 and truss 20 with or without substructure(s) or pontic (s) may be used by a dentist or laboratory technician to construct a reinforced temporary bridge with occlusal stops, eliminating the conventional use of custom castings. The ladder 10 and truss 20 with or without substructure(s) 28 or pontic(s) are incorporated chair-side by the dentist using acrylic or composite resin in conjunction with a vacuum-formed clear celluloid bridge form, or by the laboratory using heat processed acrylic.

In another exemplary application, the ladder 10 and truss 20 as designed without the substructure(s) 28 or pontic(s) can also be formed as one piece, for example, by casting or another method. The formed piece can be made from an appropriate material, such as, for example, titanium, dental hard-gold alloy, crown and bridge non-precious metal, stainless steel, cast ceramic such as Empress, among other materials. The formed piece can fit within an MO, DO, or MOD restoration to act as a reinforcement, contact point or former, occlusal and marginal ridge stops for the MO, DO, or MOD light-cured composite restoration into which they are embedded to enhance the strength, longevity and durability of a light-cured or light-polymerized resin restoration. The formed piece can also be used to reinforce a single temporary crown as previously discussed. The ladder 10 and truss 20 can provide a long lasting temporary crown, which is substantially resistant to occlusal wear.

In yet another exemplary application, the ladder 10 and truss 20, with or without substructure(s) or pontic(s), may also be used by a laboratory to fabricate an all-composite (such as BELLE GLASS) permanent bridges. After the dentist supplies an impression of conventionally prepared teeth, the laboratory can incorporate the ladder 10 and truss 20 with pontic(s) into a composite bridge to reinforce spans of missing teeth. Such structure can substantially resist torquing and provide occlusal stops and mesial and distal marginal ridge stops. Additionally, all of the previously-discussed applications may all be accomplished at the same time in the same arch.

FIGS. 30-35 illustrate another construction of a dental device, such as a dental bridge. An element which is common to an element described above and/or shown in any of FIGS. 1-29 has the same reference number followed by the letter "A".

A reinforcing structure 34A extends along an axis 178 (shown in FIG. 32) and generally includes (see FIGS. 30-31) a structural portion 20A, upstanding projections 24A, and a substructure 28A. In the illustrated construction, the reinforcing structure 34A includes a cross truss 32A transverse to the axis 178. In some constructions (not shown), the cross-truss 32A may not be provided, and the substructure 28A may be adapted for supporting an anterior pontic, in a manner similar to that described in a previous construction and illustrated in FIG. 10.

The reinforcing structure 34A is similar to the reinforcing structure 34 shown in FIG. 5. In the illustrated construction, the reinforcing structure 34A is constructed as a single piece and is strong. In the illustrated construction, the reinforcing structure 34A rests solidly on the centerline of the adjacent teeth, sitting squarely in easy-to-prepare grooves in the adjacent teeth, as described in previous constructions above. The grooves in the adjacent teeth may be generally square or may have another shape or combination of shapes. For example, the groove may be rounded or have a radius in a portion, such as the bottom of the groove, or to provide no sharp corners. In another example, the grooves may have a trapezoidal shape, such as a dove-tail shape.

Figure 30:
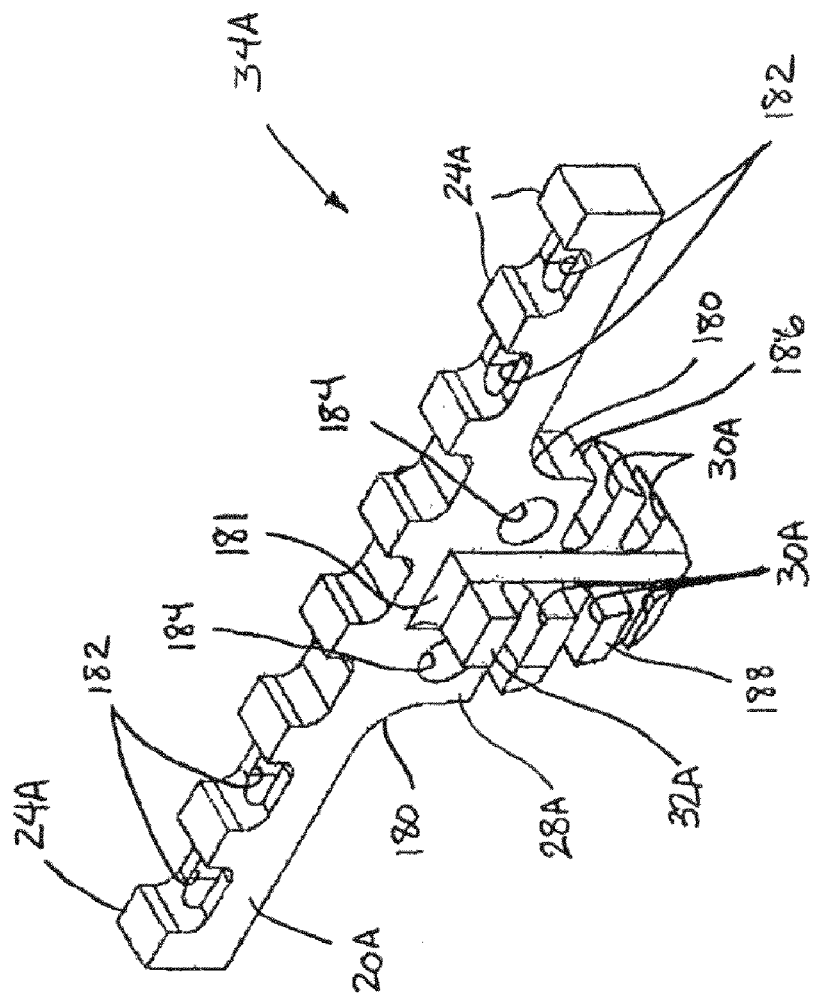
FIG. 30 is a top perspective view of another construction of a dental device, such as a truss structure or bridge framework.
Figure 31:
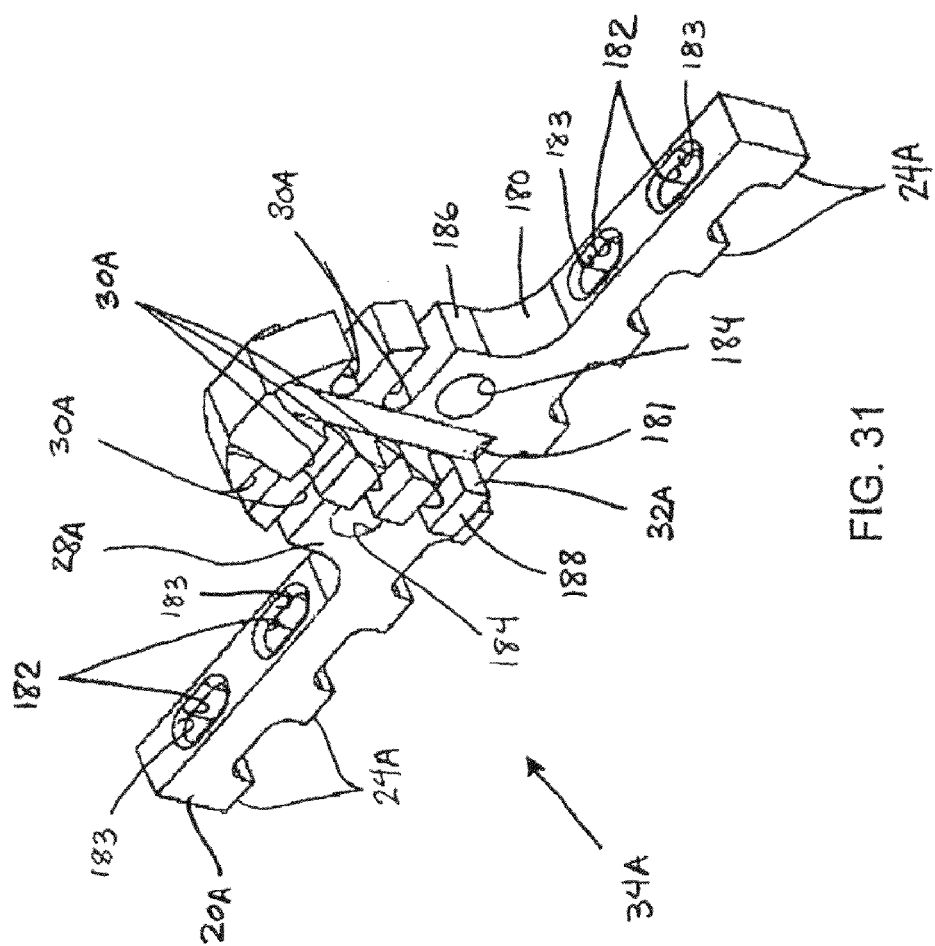
FIG. 31 is a bottom perspective view of the truss structure shown in FIG. 30.
Figure 36B:
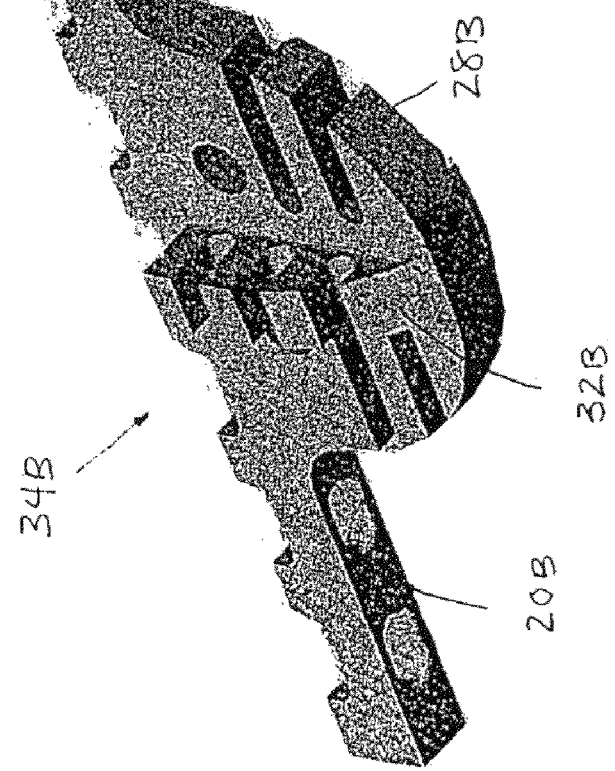
FIG. 36B is a bottom perspective view of the truss structure shown in FIG. 36A.

As shown in FIGS. 30-31 and 33, the projections 24A extend above the upper surface of the structural portion 20A in the occlusal direction, when the dental device is supported. The projections 24A may act as occlusal stops to protect the biting portion of bonded teeth from the wear that occurs through mastication and contact with the opposite set of teeth.

The reinforcing structure 34A defines (see FIG. 33) a radii surface 180 between the structural portion 20A and the substructure 28A and (see FIG. 34) a radii surface 181 between the structural portion 20A and the cross truss 32A. The radii surface(s) 180 are relatively large and may protrude from the sides of the pontic (not shown), which attaches to the substructure and is preferably a bicuspid, in a manner similar to that described above and illustrated in FIGS. 16 and 16a, and engage grooves on the sides of adjacent teeth (not shown) to provide the pontic with additional strength and resistance to twisting forces. It should be understood that the structural portion 20A may have any length and accordingly may include any number of projections 24A and any number of vertical apertures 182 (which will be described later). In operation, the structural portion 20A may be cut to a desired length in order to engage a desired number of adjacent teeth.

In the illustrated construction (see FIG. 32), the structural portion 20A includes a plurality of generally vertical apertures 182 extending therethrough between the upper and lower surfaces, transverse to the axis 178. FIG. 35 provides a cross-sectional view of a vertical aperture 182. Bonding resin can flow through the vertical apertures 182 which, when cured, may link tooth and structural portion 20A together in a strong mechanical/chemical bond. The vertical apertures 182 include chamfered, angled or radiused lead-in surfaces 183 to, for example, improve the flow of bonding resin, the bond between the bonding resin, tooth and structural portion 20A, etc.

In other constructions (not shown), the structural portion 20A may have a roughened surface in addition to or instead of the apertures 182. The roughened surface may provide improved bonding between the structural portion 20A and bonding resin and/or material of the pontic. The structural portion 20A may define one or more recesses formed in the surface(s) of but not completely through the structural portion 20A in addition to or instead of the apertures 182.

As shown in FIG. 33, the substructure 28A includes a plurality of apertures 184 transverse to the axis 178. The apertures 184 may be substantially horizontal. The substructure 28A also includes open slots 30A extending inwardly from a peripheral surface 186 of the substructure 28A, into which a bonding resin and/or material of the pontic can flow and may link the substructure and pontic in a strong mechanical/chemical bond. The slots 30A may be parallel to each other and/or to the axis 178.

As shown in FIG. 34, the cross truss 32A also has open slots 30A transverse to the axis 178 and extending inwardly from a peripheral surface 188, into which a bonding resin and/or material of the pontic can flow. These slots 30A may be parallel to each other and/or to the axis of the cross truss 32A.

In other constructions (not shown), the substructure 28A and/or the cross truss 32A may have a roughened surface in addition to or instead of the slots 30A (and/or the apertures 184). The roughened surface may provide improved bonding between the substructure 28A and/or the cross truss 32A and bonding resin and/or material of the pontic. The substructure 28A and/or the cross truss 32A may define one or more recesses formed in the surface(s) of but not completely through the substructure 28A and/or the cross truss 32A in addition to or instead of the slots 30A (and/or the apertures 184).

In some constructions and for some independent features, the dental device may include an insert. The insert may be similar to that described above and shown in FIGS. 21-26. In such constructions, the reinforcing portion 34A would not include the substructure 28A and the cross-truss 32A.

FIGS. 36-40 illustrate another construction of a dental device, such as a dental bridge. An element which is common to an element described above and/or shown in any of FIGS. 1-35 has the same reference number followed by the letter "B".

A reinforcing structure, or bridge framework, 34B extends along an axis 178B (shown in FIG. 37) and generally includes (see FIGS. 36A and 36B) a structural portion 20B, upstanding projections 24B, and a substructure 28B. In the illustrated construction, the reinforcing structure 34B includes a cross truss 32B transverse to the axis 178B. In some constructions (not shown), the cross-truss 32B may not be provided, and the substructure 28B may be adapted for supporting an anterior pontic, in a manner similar to that described in a previous construction and illustrated in FIG. 10.

The reinforcing structure 34B is similar to the reinforcing structure 34A shown in FIG. 30. In the illustrated construction, the reinforcing structure 34B is constructed as a single piece. The reinforcing structure 34B is strong and, in the illustrated construction, rests solidly on the centerline of the adjacent teeth, sitting squarely in easy-to-prepare square grooves in the adjacent teeth, as described in previous constructions above. Additionally, the illustrated construction is slightly larger than 34A (i.e., longer in the axial direction) because it is sized for a supporting a molar pontic.

As shown in FIGS. 36A and 38, the projections 24B extend above the upper surface of the structural portion 20B in the occlusal direction, when the dental device is supported. The projections 24B may act as occlusal stops to protect the biting portion of bonded teeth from the wear that occurs through mastication and contact with the opposite set of teeth.

The reinforcing structure 34B defines (see FIG. 38) a radii surface 180B between the structural portion 20B and the substructure 28B and (see FIG. 36B) a radii surface 181B between the structural portion 20B and the cross truss 32B. The radii surface(s) 180B is relatively large and may protrude from the sides of the pontic (not shown), which attaches to the substructure 28B and is preferably a molar, in a manner similar to that described above and illustrated in FIGS. 16 and 16a, and engage grooves on the sides of adjacent teeth (not shown) to provide the pontic with additional strength and resistance to twisting forces. It should be understood that the structural portion 20B may have any length and accordingly may include any number of projections 24B and any number of vertical apertures 182B (which will be described later). In operation, the structural portion 20B may be cut to a desired length in order to engage a desired number of adjacent teeth.

In the illustrated construction (see FIG. 37), the structural portion 20B includes a plurality of generally vertical apertures 182B extending therethrough between the upper and lower surfaces, transverse to the axis 178B. FIG. 40 provides a cross-sectional view of a vertical aperture 182B. Bonding resin can flow through the vertical apertures 182 which, when cured, may link tooth and structural portion 20A together in a strong mechanical/chemical bond. The vertical apertures 182B also include chamfered surfaces 183B.

In other constructions (not shown), the structural portion 20B may have a roughened surface in addition to or instead of the apertures 182B. The roughened surface may provide improved bonding between the structural portion 20B and bonding resin and/or material of the pontic. The structural portion 20B may define one or more recesses formed in the surface(s) of but not completely through the structural portion 20B in addition to or instead of the apertures 182B.

As shown in FIG. 38, the substructure 28B includes a plurality of horizontal apertures 184B transverse to the axis 178B, and open slots 30B extending inwardly from a peripheral surface 186B of the substructure 28B and parallel to the axis 178B, into which a bonding resin can flow and may link the substructure and pontic in a strong mechanical/chemical bond. As shown in FIG. 39, the cross truss 32B also has open slots 30B transverse to the axis 178B and extending inwardly from a peripheral surface 188B, into which a bonding resin can flow.

In other constructions (not shown), the substructure 28B and/or the cross truss 32B may have a roughened surface in addition to or instead of the slots 30B (and/or the apertures 184B). The roughened surface may provide improved bonding between the substructure 28B and/or the cross truss 32B and bonding resin and/or material of the pontic. The substructure 28B and/or the cross truss 32B may define one or more recesses formed in the surface(s) of but not completely through the substructure 28B and/or the cross truss 32B in addition to or instead of the slots 30B (and/or the apertures 184B).

FIGS. 41-44 illustrate another construction of a dental device, such as a dental bridge. An element which is common to an element described above and/or shown in any of FIGS. 1-40 has the same reference number followed by the letter "C".

A reinforcing structure, or bridge framework, 190 generally includes (see FIG. 41) a structural portion 20C that generally extends along a first axis 192 and a substructure 28C that generally extends along a second axis 194, which is substantially perpendicular to the first axis 192. The substructure 28C is adapted for supporting an anterior pontic, such as an incisor, in a manner similar to that described in a previous construction and illustrated in FIG. 10.

In the illustrated construction, the reinforcing structure 190 is constructed as a single piece. The reinforcing structure 190 includes a labial side 196 and a lingual side 198. The structural portion 20C sits squarely in easy-to-prepare grooves on the lingual side of adjacent teeth. A pontic, preferably an incisor, is formed around the substructure 28C and is disposed substantially towards the labial side 196.

The reinforcing structure 190 defines (see FIG. 43) a radii surface 180C between the structural portion 20C and the substructure 28C. The radii surface(s) 180C is relatively large and may protrude from the sides of the pontic (not shown), which attaches to the substructure 28B and is preferably an incisor, in a manner similar to that described above and illustrated in FIGS. 16 and 16a, and engage grooves on the sides of adjacent teeth (not shown) to provide the pontic with additional strength and resistance to twisting forces. It should be understood that the structural portion 20C may have any length and accordingly may include any number of generally horizontal apertures 200 (which will be described later). In operation, the structural portion 20C may be cut to a desired length in order to engage a desired number of adjacent teeth.

In the illustrated construction (see FIG. 43), the structural portion 20C includes a plurality of apertures 200 extending therethrough between the labial surface 196 and the lingual surface 198, transverse to the axis 192. The apertures 200 may be substantially horizontal. Bonding resin can flow through the horizontal apertures 200 which, when cured, may link tooth and structural portion 20C together in a strong mechanical/chemical bond. The apertures 200 also include chamfered, angled or radiused lead-in surfaces 183C.

As shown in FIG. 43, the substructure 28C includes a plurality of apertures 184C transverse to the axis 194 into which a bonding resin and/or material of the pontic can flow and may link the substructure and pontic in a strong mechanical/chemical bond. The apertures 184C may be generally horizontal. For improved strength, the reinforcing structure 190 has a generally trapezoidal shape as can be seen from the side view of FIG. 44.

In other constructions (not shown), the structural portion 20C and/or the substructure 28C may have a roughened surface in addition to or instead of the apertures 200 and/or the apertures 184C. The roughened surface may provide improved bonding between the structural portion 20C and/or the substructure 28C and bonding resin and/or material of the pontic. The structural portion 20C and/or the substructure 28C may define one or more recesses formed in the surface(s) of but not completely through the structural portion 20C and/or the substructure 28C in addition to or instead of the apertures 200 and/or the apertures 184C.

FIGS. 45-49 illustrate another construction of a dental device, and FIGS. 50-54 illustrate yet another construction of a dental device, such as a dental insert, or reinforcing spine. An element which is common to an element described above and/or shown in any of FIGS. 1-44 has the same reference number followed by the letter "D" or "E", respectively.

Figure 45:
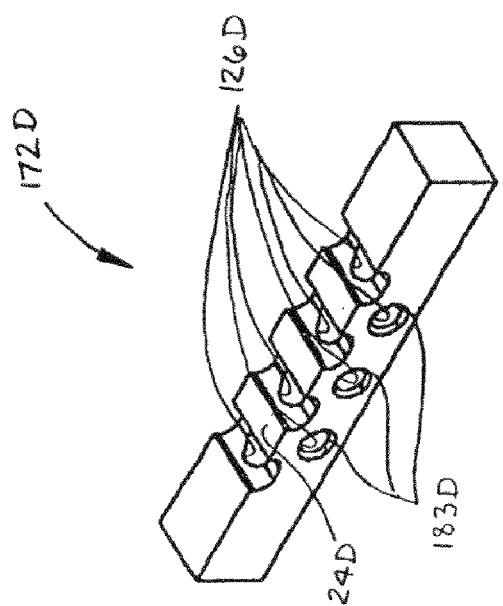
FIG. 45 is a perspective view of another construction of an insert for use in individual single composite restorations.

FIG. 45 illustrates an insert, or reinforcing spine, 172D for use in individual composite restorations, similar to the insert 172 described above and shown in FIGS. 25-26c. The insert 172D is sized for use with bicuspid teeth and can be made of an appropriate material, such as, for example, gold, titanium, laboratory processed composite, etc. The insert 172D is imbedded into unpolymerized composite resin and then the resin is tamped over and light-polymerized or cured. Thus, the insert 172D will form the contact points, the marginal ridges, and the occlusal stops 24D of a bonded composite restoration. Each axial end of the insert 172D may be engageable with and provide a contact surface for the surface of the adjacent tooth.

The insert 172D includes multiple apertures 126D to, for example, allow resin to flow through and around the insert 172D in creating the composite restoration. FIGS. 46-49 are multiple views of the insert 172D to illustrate the location of the apertures 126D. The apertures 126D may be generally vertical or generally horizontal, as illustrated. The apertures 126D also include chamfered, angled or radiused lead-in surfaces 183D. The location of the apertures 126D is not limited to the locations shown. More or fewer apertures 126D can be incorporated into the insert 172D at nearly any location on the insert 172D.

In another construction, the insert 172D may have a roughened surface in addition to or instead of the apertures 126D. The roughened surface may provide improved bonding between the insert 172D and bonding resin and/or material of the pontic. The insert 172D may define one or more recesses formed in the surface(s) of but not completely through the insert 172D in addition to or instead of the apertures 126D.

Figure 50:
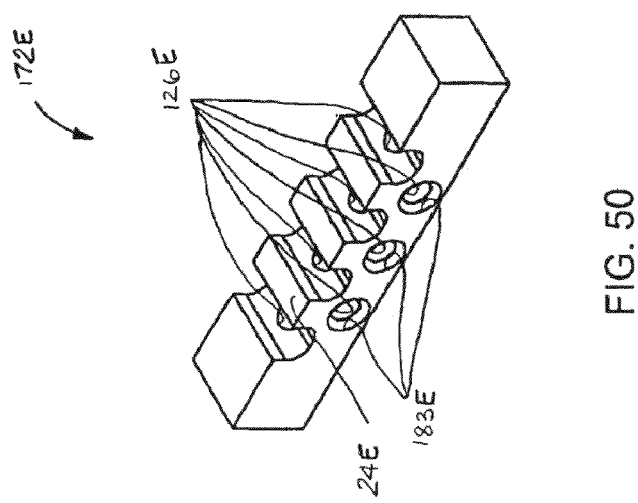
FIG. 50 is a perspective view of another construction of an insert for use in individual single composite restorations.
Figure 53:
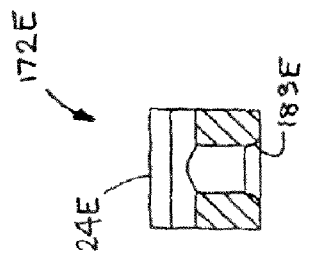
FIG. 53 is a partial cross-sectional view of a portion of the insert taken generally along line 53-53 in FIG. 52.
Figure 54:
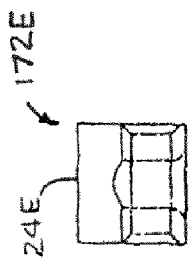
FIG. 54 is a right side view of the insert shown in FIG. 50.
Figure 51:
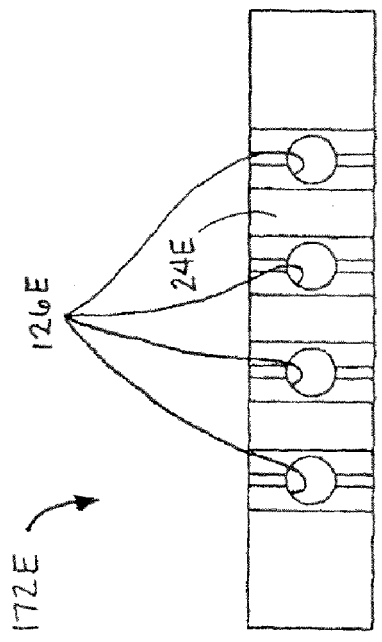
FIG. 51 is a top view of the insert shown in FIG. 50.
Figure 52:
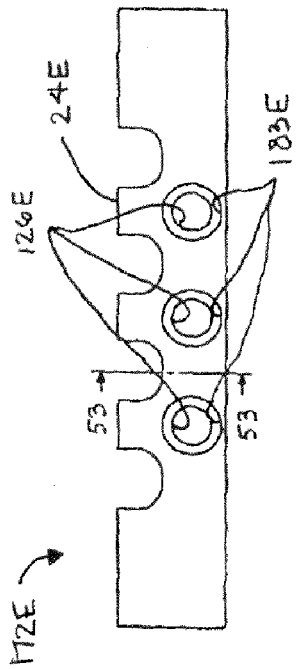
FIG. 52 is a front view of the insert shown in FIG. 50.

FIG. 50 illustrates an insert, or reinforcing spine, 172E for use in individual single composite restorations, similar to the insert 172D described above and shown in FIGS. 45-49. The insert 172E, however, is sized for use with molars. As can be seen in FIGS. 50-54, the insert 172E can be described similarly with respect to the occlusal stops 24E, apertures 126E and chamfered, angled, or radiused lead-in surfaces 183E as the insert 172D, above. However, the insert 172E is larger than the insert 172D. Each axial end of the insert 172E may be engageable with and provide a contact surface for the surface of the adjacent tooth.

In another construction, the insert 172E may have a roughened surface in addition to or instead of the apertures 126E. The roughened surface may provide improved bonding between the insert 172E and bonding resin and/or material of the pontic. The insert 172E may define one or more recesses formed in the surface(s) of but not completely through the insert 172E in addition to or instead of the apertures 126E.

FIGS. 55-63 illustrate another construction of a dental device, such as a dental bridge 35F (see FIG. 55) and a dental bridge framework 34F. An element which is common to an element described above and/or shown in any of FIGS. 1-54 has the same reference number followed by the letter "F".

Figure 55:
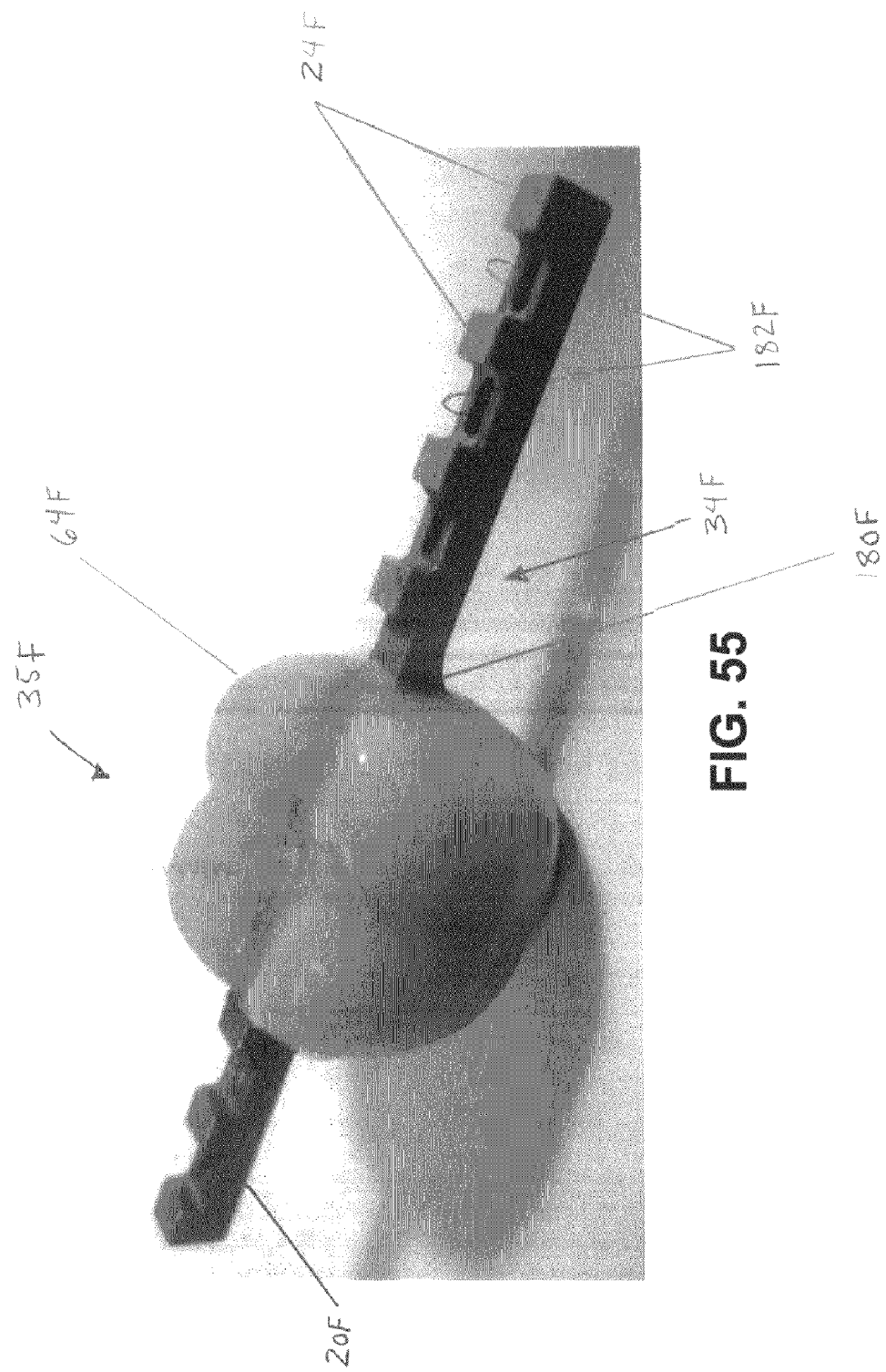
FIG. 55 is a top perspective view of an alternative construction of a dental bridge.
Figure 56:
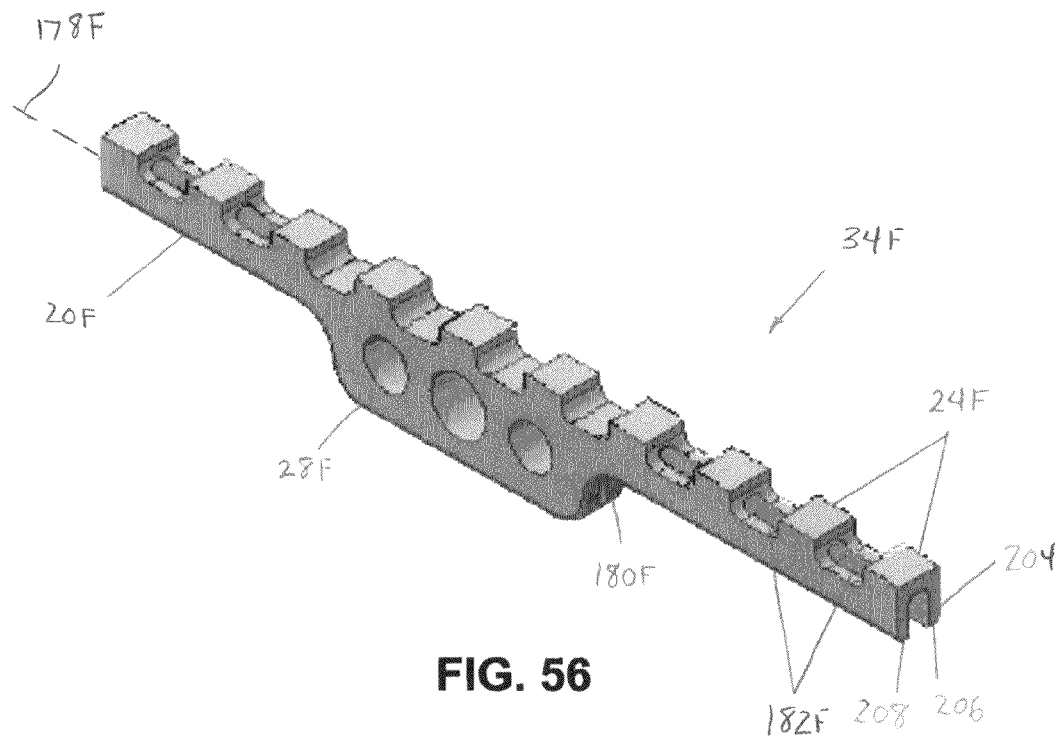
FIG. 56 is another top perspective view of a portion of a dental framework shown in FIG. 55.
Figure 57:
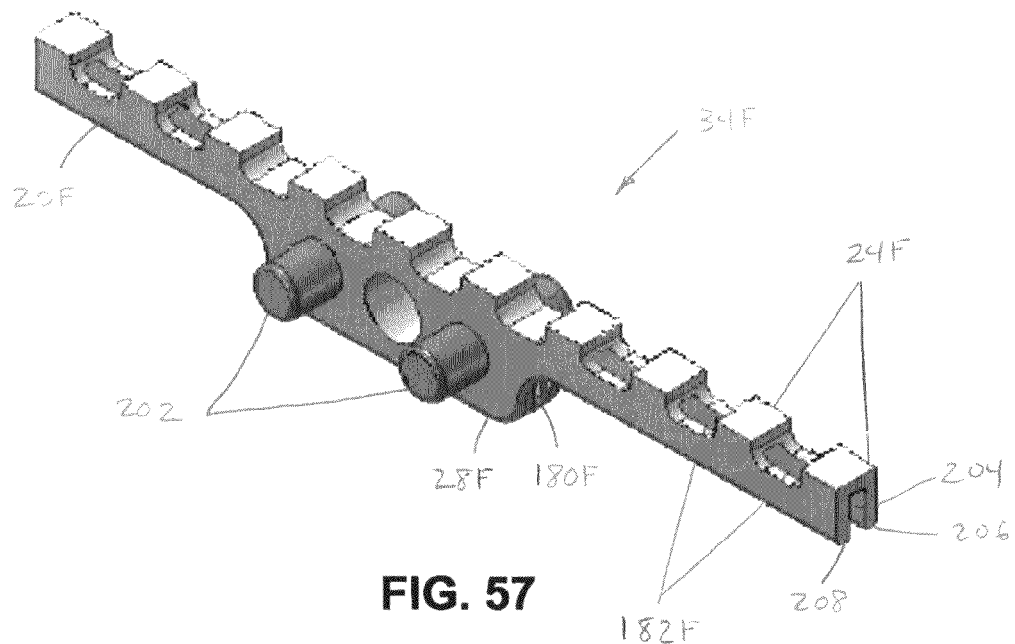
FIG. 57 is another top perspective view of the framework shown in FIG. 55.

As shown in FIG. 55, the bridge 35F includes the reinforcing structure or bridge framework 34F and a pontic 64F. In the illustrated bridge 35F, the framework 34F is longer on one side of the pontic 64F, and the longer side will be bonded to more than one abutment tooth (not shown). In other constructions (not shown), the bridge 35F may be bonded to one or more abutment teeth on either or both sides. During installation, the framework 34F may be cut to a desired length in order to engage a desired number of adjacent teeth.

The framework 34F extends along (see FIG. 56) an axis 178F and generally includes a structural portion 20F, upstanding projections 24F, and a substructure 28F. In the illustrated construction (see FIGS. 57-63), the framework 34F includes pins 202 extending transverse to the axis 178F. In the illustrated construction, the framework 34F is constructed as a single piece. The framework 34F is strong and, in the illustrated construction, rests solidly on the centerline of the adjacent teeth, sitting squarely in easy-to-prepare grooves in the adjacent abutment teeth, as described in previous constructions above.

In the illustrated construction, the projections 24F extend above the upper surface of the structural portion 20F in the occlusal direction, when the dental device is supported, to act as occlusal stops for the pontic 64F (see FIG. 55) and/or for the abutment teeth (not shown) and, for example, provide improved anti-wear properties for the pontic 6F and/or the abutment teeth. In the illustrated construction, the structural portion 20F includes a plurality of generally vertical apertures 182F extending therethrough between the upper and lower surfaces, transverse to the axis 178F. Bonding resin can flow through the vertical apertures 182F and around the structural portion 20F, and the bonding resin, when cured, may link the tooth and the structural portion 20F together in a strong mechanical/chemical bond. The structural portion 20F may have any length and accordingly may include any number of projections 24F and any number of vertical apertures 182F.

In the illustrated construction, slots 204 are formed in each end of the structural portion 20F. Each slot 204 has opposite side walls 206, 208 depending from the upper surface. On opposite sides of the substructure 28F, the structural portion 20F is provided by the side walls 206, 208 connected by the projections 24F.

In the illustrated construction, formation of the projections 24F and the slots 204 causes the apertures 182F to be formed. More specifically, the projections 24F are formed by removing material between adjacent projections 24F. The material is removed to provide a recess having a given depth (to a surface below the occlusal surface of the projections 24F) and length. The slots 204 are formed into the second surface of the structural portion 20F to at least the depth of the recesses such that an aperture 182F is formed in each recess. In other constructions, the apertures 182F may be formed in a different manner such as by forming the slots 204F before or concurrently with removing the material between the projections 24F or by milling.

In the illustrated construction, the recesses are formed with a length that is greater than the width of the structural portion 20F which, after formation of the slots 204 results in elongated apertures 182F. Also, the slots 204 are formed beyond the depth of the recesses such that each aperture 182F is short in the vertical direction. The elongated shape and short height of the apertures 182F may improve flow of bonding resin through the apertures 182F.

Figure 58:
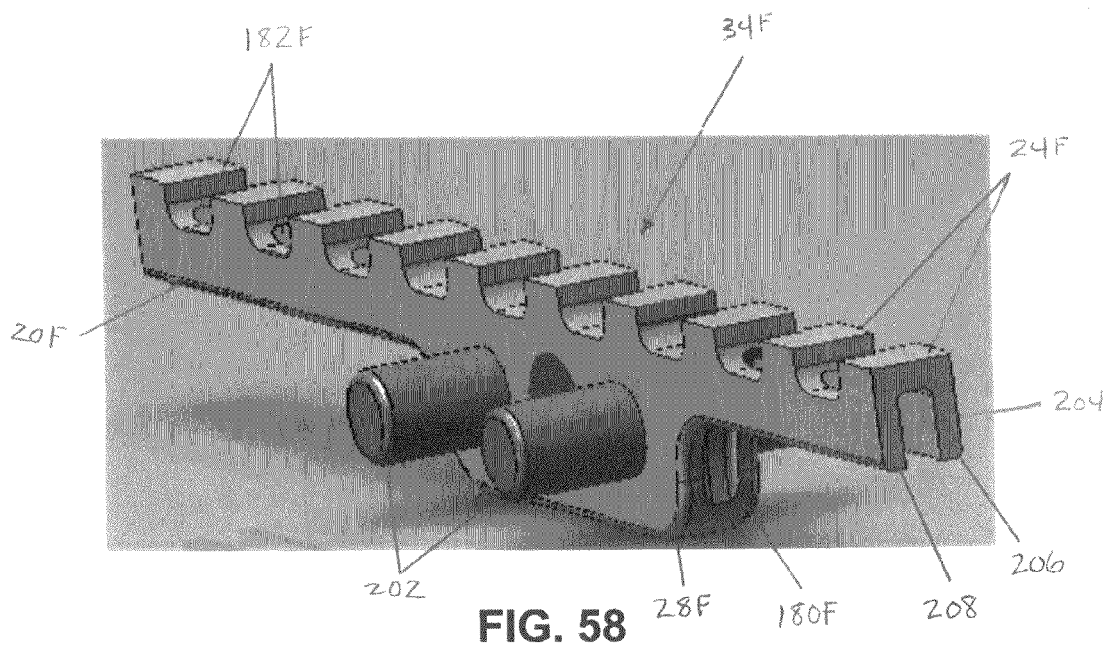
FIG. 58 is another top perspective view of the framework shown in FIG. 55.
Figure 59:
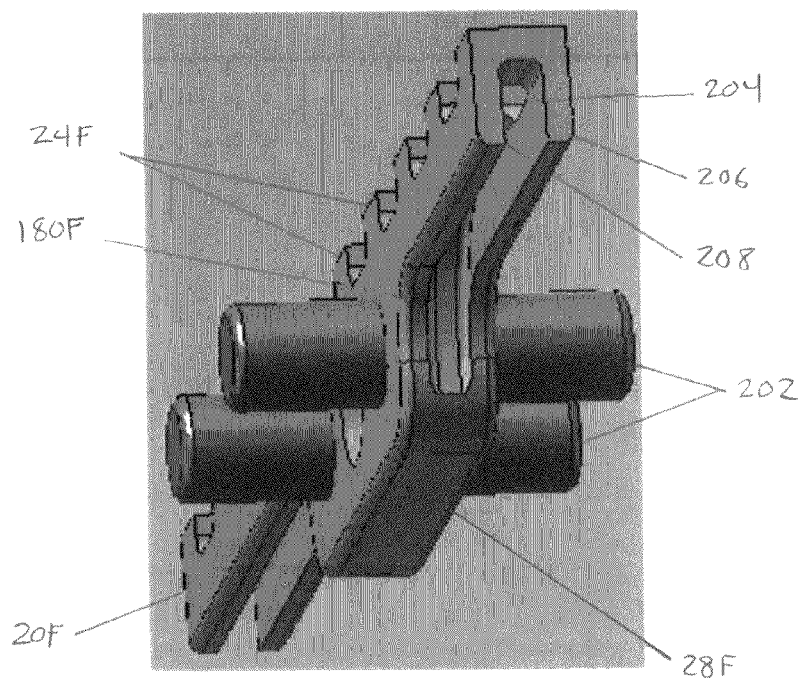
FIG. 59 is another bottom perspective view of the framework shown in FIG. 55.
Figure 60:
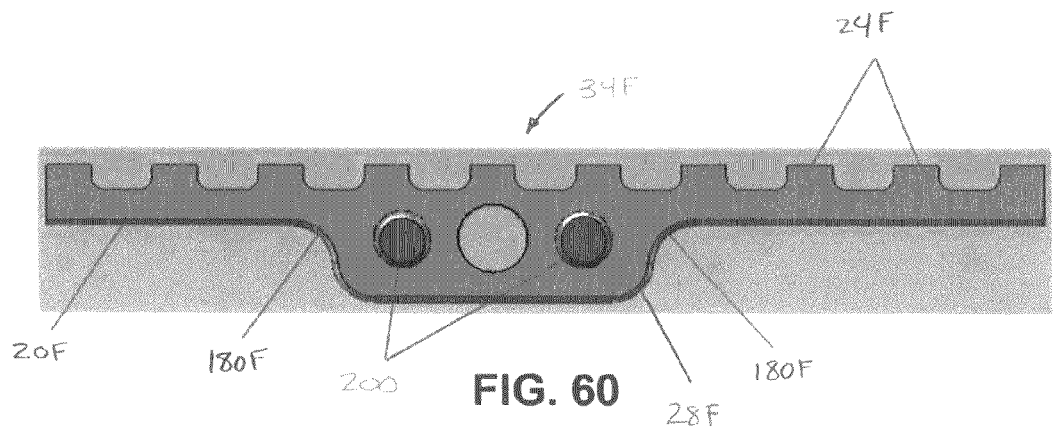
FIG. 60 is a front view of the framework shown in FIG. 55.
Figure 61:
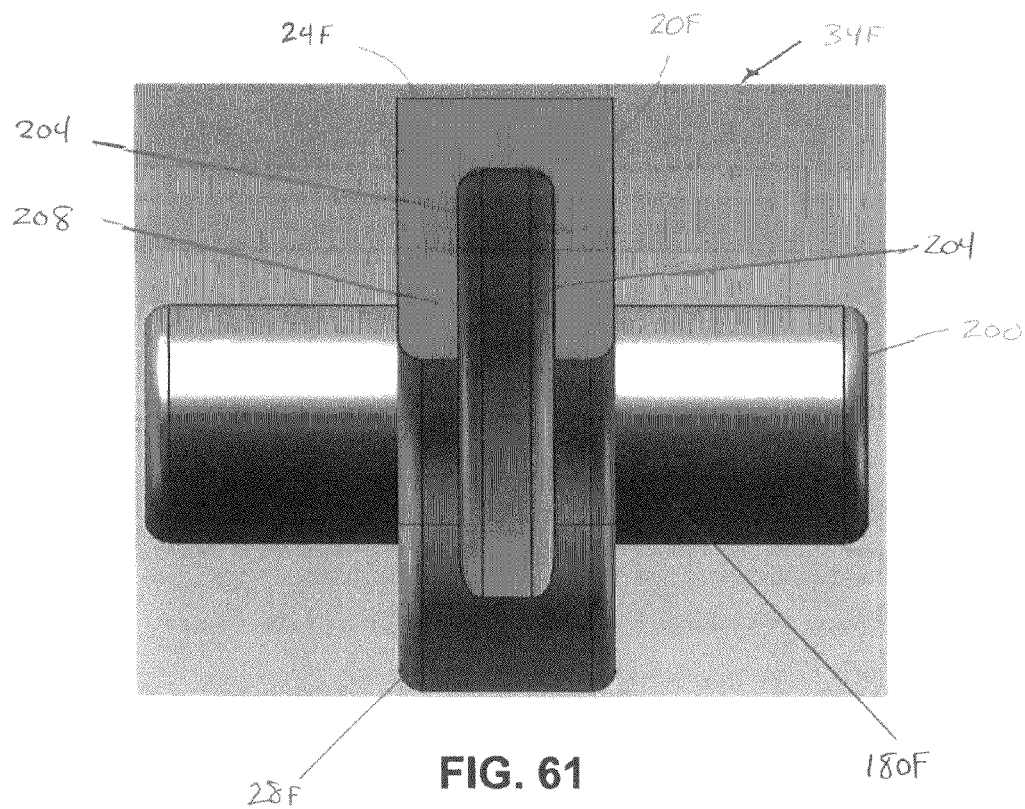
FIG. 61 is an end view of the framework shown in FIG. 55.
Figure 62:
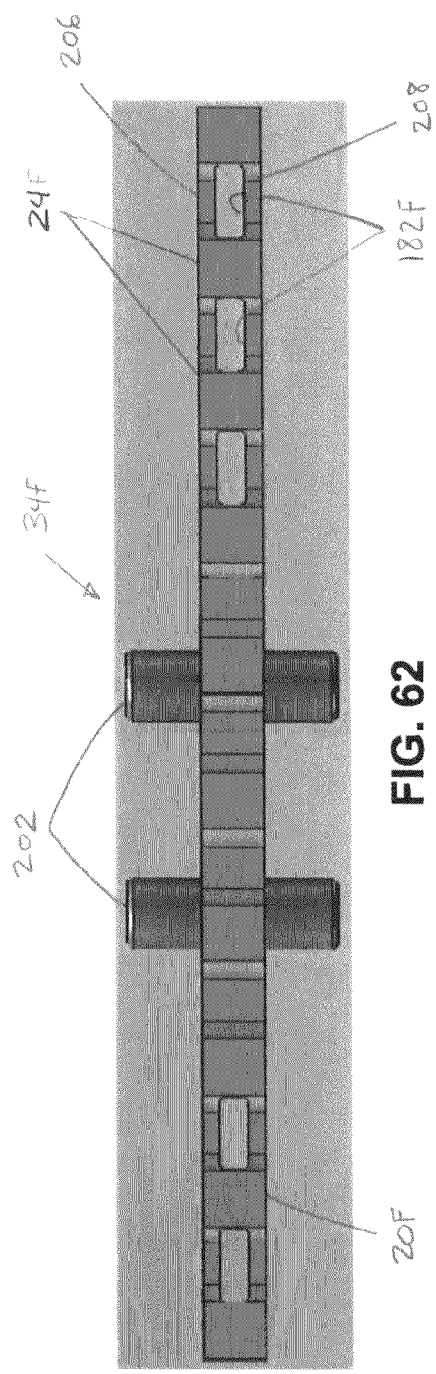
FIG. 62 is a top view of the framework shown in FIG. 55.
Figure 63:
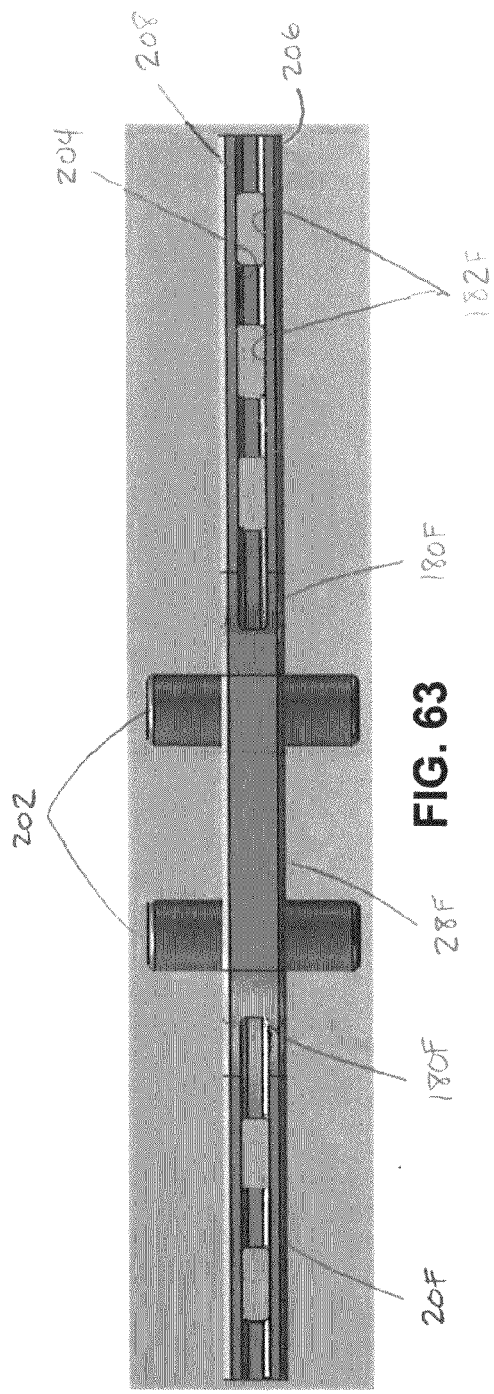
FIG. 63 is a bottom view of the framework shown in FIG. 55.

The framework 34F defines (see FIG. 60) a radius surface 180F between the structural portion 20F and the substructure 28F. The radii surface(s) 180F is relatively large and may protrude from the sides of the pontic 64F (see FIG. 55), which attaches to the substructure 28F, and may engage the grooves on the sides of adjacent teeth (not shown) to provide additional strength and/or resistance to twisting forces. As shown in FIGS. 58-59 and 61, a portion of each slot 204 may extend into the adjacent radius surface 180F. When material is removed from the pontic 64F, additional portions of the substructure 28F may protrude from the pontic 64F. The additional portion(s) of the substructure 28F may also engage in the grooves in the abutment teeth.

In the illustrated construction, the pontic 64F is generally formed in an over-sized tooth shape, and material is removed, as necessary, to fit the missing tooth space or endentulous space. The pontic 64F is formed generally symmetrical so that the bridge 35F may be used in any portion of the patient's mouth (top, bottom, left side, right side) and in either orientation of the framework 34F (longer end facing forward or to the rear). The symmetrical pontic 64F is trimmed and shaped to provide the desired replacement tooth. In other constructions (not shown), the pontic 64F may be formed so that the bridge 35F is used in only a given area of the mouth and/or in one orientation of the framework 34F.

The sides of the illustrated pontic 64F are formed contiguous with the transition between the radius surfaces 180F where the substructure 28F joins the structural portion 20F so that when pontic material is removed to provide a proper fit between the abutment teeth during installation, the radius surface 180F may be more exposed (and other portions of the substructure 20F may be exposed) to engage into the preps in the sides of the abutment teeth.

To install the above-described dental devices and dental bridges, a dentist determines how many abutment teeth will be utilized to support the dental device. In some cases, improved support and tooth stability may be achieved by utilizing two abutment teeth on one side of the edentulous space. The teeth and edentulous space are measured to determine the length to be bridged. The teeth are marked indicating the prep length and width. In the illustrated constructions, the maximum length will, for example, accommodate 25 mm for the bicuspid bridge and 35.8 mm for the molar bridge. The dental device can be used as the template to facilitate this marking.

Preparations are cut in the abutment teeth as marked using appropriate MO, DO or MOD preps in the two or three abutment teeth. In the illustrated constructions, the preps may be, for example, slightly more than 1.9 mm wide for a molar bridge and slightly more than 1.7 mm wide for a bicuspid bridge. The preps may have rounded corners to enhance mechanical bonding. Prep depth may be such that the occlusal surface of the occlusal stops of the dental device is contiguous with the surface of the central fossa of the abutment teeth.

The length of the framework is trimmed to fit the preps. The size of the pontic is adjusted to fit the edentulous space. The framework and pontic can be trimmed and shaped with standard dental burs, discs, wheels, etc. When adjusting the size of the pontic, the material of the framework and the radius curve at the pontic-framework junction on both sides of the pontic is maintained. The preps in the adjacent abutment teeth may be adjusted by extending them along the distal and/or mesial side of the abutment teeth to accommodate the radius curve of the framework which, when bonded, may provide improved torsional stability for the dental device.

The gum side of the pontic may be adjusted to fit the tissue of the edentulous space lightly. The pontic may also be fit and adjusted as a sanitary pontic. The gum side of the pontic is finished and polished into an appropriate modified ridge lap or bullet shape. If there is not enough material or if too much material has been removed from the pontic for the desired fit, material can be easily added. The surface of the pontic is roughened, and a thin coat of bonding resin followed by the desired amount of composite resin is applied, cured and shaped. When utilizing the (indirect method), the steps should be done on the model first.

Prior to bonding, the dental device should seat passively into the preps, and the occlusal surface of the occlusal stops should be at least even or slightly above the surface of the central fossa on each abutment tooth. If there is an MOD prep next to an unprepared tooth, an ultra thin matrix band may be placed to establish a non-bonded contact of the composite with the unprepared tooth. Where teeth are to be joined together, wooden wedges may be placed between the teeth to establish the gingival embrasure. Resin will not bond to the wooden wedges. When bonding the dental device into the preps, the directions for the composite resin system being used are followed.

The preps are filed with the composite resin. The framework is pressed into the composite resin so that the resin flows both around the framework and into and through the occlusal perforations. When the dental device is seated into what has been determined to be the desired position, the still uncured occlusal and interproximal composite resin is formed and adapted with instruments moistened with uncured bonding resin. When the position of the dental device and the shape and form of the composite resin are as desired, it is light cured occlusally, buccally and lingually.

The occlusal surfaces, both the composite and the occlusal stops, are adjusted as required for normal bite. The buccal and lingual surfaces are trimmed and adjusted. The embrasures are opened to allow a Proxabrush or Super-Floss to be inserted for easy cleaning. All surfaces of the pontic, truss and cured composite resin are polished, and installation is complete.

One or more independent features or independent advantages of the invention may be set forth in the following claims:

What is claimed is:

1. A method of manufacturing a prefabricated dental bridge, the method comprising:
    forming a unitary dental bridge framework connectable to at least two abutment teeth, each abutment tooth having a tooth occlusal surface, forming the unitary dental bridge framework including
        forming a structural portion extending along an axis and having a width transverse to the axis and a length along the axis, the length being greater than the width, the structural portion having a first end and an opposite, second end, the first end being connectable to one abutment tooth and the second end being connectable to another abutment tooth, the structural portion having a first surface oriented toward the tooth occlusal surface and an opposite, second surface,
        forming a truss portion integrally with the structural portion and depending from the second surface of the structural portion, the truss portion being positioned along the length of the structural portion spaced from the first end and from the second end, a first portion of the length of the structural portion being defined between the truss portion and the first end and a second portion of the length of the structural portion being defined between the truss portion and the second end,
        forming a first slot in the first portion of the length, the first slot extending along the axis and from the second surface toward the first surface, the first slot having opposite side walls,
        forming a second slot in the second portion of the length, the second slot extending along the axis and from the second surface toward the first surface, the second slot having opposite side walls, and
        forming a plurality of openings extending through the structural portion transverse to the axis and from the first surface toward the second surface, the plurality of openings being spaced from the truss portion along the length of the structural portion, at least one of the plurality of openings being formed in the first portion of the length of the structural portion, at least another of the plurality of openings being formed in the second portion of the length of the structural portion; and
    forming a pontic on the dental bridge framework.

2. The method of claim 1, wherein forming the first slot causes the at least one of the plurality of openings in the first portion of the length to be formed, and wherein forming the second slot causes the at least another of the plurality of openings in the second portion of the length to be formed.

3. The method of claim 1, wherein forming the truss portion includes forming a peripheral surface of the truss portion and a radius surface connecting the second surface of the structural portion and the peripheral surface of the truss portion.

4. The method of claim 3, wherein forming the first slot includes forming a first slot portion in a first peripheral surface portion of the truss portion adjacent to the first portion of the length of the structural portion, and wherein forming the second slot includes forming a second slot portion in a second peripheral surface portion of the truss portion adjacent to the second portion of the length of the structural portion.

5. The method of claim 1, wherein forming the truss portion includes
forming a first truss portion integrally with the structural portion, the first truss portion generally extending in a first plane substantially parallel to the axis, and
forming a second truss portion integrally with the structural portion, the second truss portion generally extending in a second plane substantially transverse to the axis and substantially transverse to the first plane.

6. The method of claim 1, wherein forming the unitary dental bridge framework further includes forming a plurality of projections integrally with the structural portion on the first surface of the structural portion, each of the projections having a projection occlusal surface spaced beyond the first surface toward the tooth occlusal surface, the projection occlusal surface providing a bridge occlusal surface for the dental bridge, the structural portion being connectable to the abutment teeth with the first surface oriented toward and positioned below the tooth occlusal surface and with the bridge occlusal surface positioned at or above the tooth occlusal surface.

7. The method of claim 6, wherein forming the plurality of projections includes removing material between adjacent ones of the projections.

8. The method of claim 7, wherein removing material between adjacent ones of the projections in the first length of the structural portion and forming the first slot causes the at least one of the plurality of openings in the first portion of the length to be formed, and wherein removing material between adjacent ones of the projections in the second length of the structural portion and forming the second slot causes the at least another of the plurality of openings in the second portion of the length to be formed.

9. A method of installing a prefabricated dental bridge, the method comprising:
prior to a dentist examining a patient, manufacturing the prefabricated dental bridge, manufacturing including
forming a unitary dental bridge framework including
forming a structural portion extending along an axis, and
forming a truss portion integrally with the structural portion, the truss portion depending from the structural portion, and
forming a tooth-shaped pontic on the dental bridge framework;
providing the prefabricated dental bridge to the dentist;
examining the patient;
preparing at least two abutment teeth of the patient;
positioning the dental bridge on the abutment teeth; and
bonding the dental bridge to the abutment teeth;
wherein each abutment tooth has a tooth occlusal surface, wherein forming a unitary dental bridge framework includes
forming a structural portion extending along an axis and having a width transverse to the axis and a length along the axis, the length being greater than the width, the structural portion having a first end and an opposite, second end, the first end being connectable to one abutment tooth and the second end being connectable to another abutment tooth, the structural portion having a first surface oriented toward the tooth occlusal surface and an opposite, second surface,
forming a truss portion integrally with the structural portion and depending from the second surface of the structural portion, the truss portion being positioned along the length of the structural portion spaced from the first end and from the second end, a first portion of the length of the structural portion being defined between the truss portion and the first end and a second portion of the length of the structural portion being defined between the truss portion and the second end,
forming a first slot in the first portion of the length, the first slot extending along the axis and from the second surface toward the first surface, the first slot having opposite side walls,
forming a second slot in the second portion of the length, the second slot extending along the axis and from the second surface toward the first surface, the second slot having opposite side walls, and
forming a plurality of openings extending through the structural portion transverse to the axis and from the first surface toward the second surface, the plurality of openings being spaced from the truss portion along the length of the structural portion, at least one of the plurality of openings being formed in the first portion of the length of the structural portion, at least another of the plurality of openings being formed in the second portion of the length of the structural portion; and
wherein positioning the dental bridge includes
positioning the first portion of the structural portion on one abutment tooth, and
positioning the second portion of the structural portion on another abutment tooth.

10. The method of claim 9, wherein forming the first slot causes the at least one of the plurality of openings in the first portion of the length to be formed, and wherein forming the second slot causes the at least another of the plurality of openings in the second portion of the length to be formed.

11. The method of claim 9, wherein forming the unitary dental bridge framework further includes forming a plurality of projections integrally with the structural portion on the first surface of the structural portion, each of the projections having a projection occlusal surface spaced beyond the first surface toward the tooth occlusal surface, the projection occlusal surface providing a bridge occlusal surface for the dental bridge, and wherein positioning includes positioning the structural portion on the abutment teeth with the first surface oriented toward and positioned below the tooth occlusal surface and with the bridge occlusal surface positioned at or above the tooth occlusal surface.

12. The method of claim 11, wherein forming the plurality of projections includes removing material between adjacent ones of the projections.

13. The method of claim 12, wherein removing material between adjacent ones of the projections in the first length of the structural portion and forming the first slot causes the at least one of the plurality of openings in the first portion of the length to be formed, and wherein removing material between adjacent ones of the projections in the second length of the structural portion and forming the second slot causes the at least another of the plurality of openings in the second portion of the length to be formed.

14. The method of claim 9, wherein preparing at least two abutment teeth includes forming a groove in each abutment tooth, wherein positioning the dental bridge includes positioning the first portion of the structural portion in the groove in one abutment tooth and the second portion of the structural portion in the groove in another abutment tooth, and wherein bonding the dental bridge includes applying bonding resin to the abutment teeth, the bonding resin flowing through the openings in the structural portion.

15. The method of claim 9, wherein forming the truss portion includes forming a peripheral surface of the truss portion and a radius surface connecting the second surface of the structural portion and the peripheral surface of the truss portion, and wherein positioning the dental bridge includes engaging the radius surface with at least one abutment tooth to resist twisting forces on the dental bridge after installation.

16. The method of claim 15, wherein forming the first slot includes forming a first slot portion in a first peripheral surface portion of the truss portion adjacent to the first portion of the length of the structural portion, and wherein forming the second slot includes forming a second slot portion in a second peripheral surface portion of the truss portion adjacent to the second portion of the length of the structural portion.

17. A prefabricated dental bridge comprising:
a unitary dental bridge framework connectable to at least two abutment teeth, the unitary dental bridge framework including
a structural portion extending along an axis, and
a truss portion integrally formed with the structural portion and depending from the structural portion; and
a tooth-shaped pontic formed on the dental bridge framework;
wherein each abutment tooth has a tooth occlusal surface, wherein the structural portion extends along an axis and has a width transverse to the axis and a length along the axis, the length being greater than the width, the structural portion having a first end and an opposite, second end, the first end being connectable to one abutment tooth and the second end being connectable to another abutment tooth, the structural portion having a first surface oriented toward the tooth occlusal surface and an opposite, second surface, wherein the truss portion depends from the second surface of the structural portion, the truss portion being positioned along the length of the structural portion spaced from the first end and from the second end, a first portion of the length of the structural portion being defined between the truss portion and the first end and a second portion of the length of the structural portion being defined between the truss portion and the second end, wherein a first slot is formed in the first portion of the length, the first slot extending along the axis and from the second surface toward the first surface, the first slot having opposite side walls, wherein a second slot is formed in the second portion of the length, the second slot extending along the axis and from the second surface toward the first surface, the second slot having opposite side walls, and wherein a plurality of openings extend through the structural portion transverse to the axis and from the first surface toward the second surface, the plurality of openings being spaced from the truss portion along the length of the structural portion, at least one of the plurality of openings being formed in the first portion of the length of the structural portion, at least another of the plurality of openings being formed in the second portion of the length of the structural portion.

18. The dental bridge of claim 17, wherein the truss portion has a peripheral surface, and wherein a radius surface connects the second surface of the structural portion and the peripheral surface of the truss portion.

19. The dental bridge of claim 18, wherein a first slot portion is formed in a first peripheral surface portion of the truss portion adjacent to the first portion of the length of the structural portion, and wherein a second slot portion is formed in a second peripheral surface portion of the truss portion adjacent to the second portion of the length of the structural portion.

20. The dental bridge of claim 17, wherein the structural portion includes a plurality of projections integrally formed on the first surface, each of the projections having a projection occlusal surface spaced beyond the first surface toward the tooth occlusal surface, the projection occlusal surface providing a bridge occlusal surface for the dental bridge, the structural portion being connectable to the abutment teeth with the first surface oriented toward and positioned below the tooth occlusal surface and with the bridge occlusal surface positioned at or above the tooth occlusal surface.

21. The dental bridge of claim 20, wherein the plurality of projections are formed by removing material between adjacent ones of the projections.

22. The dental bridge of claim 17, wherein the truss portion includes
a first truss portion formed integrally with the structural portion, the first truss portion generally extending in a first plane substantially parallel to the axis, and
a second truss portion formed integrally with the structural portion, the second truss portion generally extending in a second plane substantially transverse to the axis and substantially transverse to the first plane.

* * * * *